(12) United States Patent
Radeke et al.

(10) Patent No.: US 6,762,177 B2
(45) Date of Patent: Jul. 13, 2004

(54) SPIROCYCLIC LIGANDS FOR SIGMA RECEPTORS, AND LIBRARIES AND METHODS OF USE THEREOF

(75) Inventors: Heike Radeke, Dedham, MA (US); Paul E. Persons, Westborough, MA (US); James R. Hauske, Concord, MA (US)

(73) Assignee: Sepracor, Inc., Marlborough, MA (US)

( * ) Notice: Subject to any disclaimer, the term of this patent is extended or adjusted under 35 U.S.C. 154(b) by 0 days.

(21) Appl. No.: 10/289,119

(22) Filed: Nov. 5, 2002

(65) Prior Publication Data

US 2003/0171355 A1 Sep. 11, 2003

Related U.S. Application Data

(63) Continuation of application No. 09/633,411, filed on Aug. 7, 2000, now Pat. No. 6,476,019.
(60) Provisional application No. 60/148,918, filed on Aug. 13, 1999.

(51) Int. Cl.$^7$ .................. C07D 471/10; C07D 221/00; C07D 223/00; A61K 31/438; A61K 31/55
(52) U.S. Cl. .................. 514/212.08; 514/278; 540/522; 540/543; 546/16; 546/18
(58) Field of Search .............................. 540/522, 543; 546/16, 18; 514/212.08, 278

(56) References Cited

U.S. PATENT DOCUMENTS

| | | | |
|---|---|---|---|
| 5,434,158 A | 7/1995 | Shah | 514/278 |
| 5,763,471 A | 6/1998 | Fourtillan et al. | 514/409 |

FOREIGN PATENT DOCUMENTS

| | | |
|---|---|---|
| WO | WO 96/05203 | 2/1996 |

OTHER PUBLICATIONS

Brown et al.;"The Synthesis of Antioxidants Showing Selective Affinity for Low Density Lipoproteins", J. Chem. Soc. Perkin Trans., 1: 2329–2336 (1997).

Cossy et al.; "Synthesis of Spiro[Quinoline–2,4'–Piperidines]", Tetrahedron Letters 39:2965–2968 (1998).

Cossy et al.; "Synthesis of Spiro[benzazepine–2,4'–piperidine]", J. Org. Chem. 63: 4554–4557 (1998).

Cossy et al.; Heck Reaction versus Free Radical Reaction for the Synthesis of Spiro[indoline–2,4'–piperidines], Synlett, pp. 251–252 (Mar. 1998).

Ganapathy et al.; "Molecular and Ligand –Binding Characterization of the σ–Receptor in the Jurkat Human T Lymphocyte Cell Line[1]", The Journal of Pharmacology and Experimental Therapeutics, 289(1): 251–260 (1999).

Quaglia, W. et al., "1'–Benzyl–3,4–dihydrospiro[2H–1–benzothiopyran–2,4'–piperidine] (Spipethiane), a Potent and Highly Selective $\sigma_1$ Ligand", Journal of Medicinal chemistry 41(10): 1557–1560 (May 7, 1998).

Sulsky et al.;"Conformational Switching and the Synthesis of Spiro[2H–indol]–3(1H)–ones by Radical Cyclization", J. Org. Chem. 64: 5504–5510 (1999).

Primary Examiner—Bruck Kifle
(74) Attorney, Agent, or Firm—Dana M. Gordon; Foley & Hoag LLP

(57) ABSTRACT

One aspect of the present invention relates to spirocyclic compounds. Another aspect of the present invention relates to the use of the spirocyclic compounds as ligands for mammalian G-protein-coupled receptors or sigma receptors. The present invention also relates to methods of modulating the activity of a G-protein-coupled receptor or a sigma receptor in a mammal using the spirocyclic compounds of the present invention. The present invention also relates to methods of treating various diseases in a mammal using the spirocyclic compounds of the present invention.

48 Claims, No Drawings

SPIROCYCLIC LIGANDS FOR SIGMA RECEPTORS, AND LIBRARIES AND METHODS OF USE THEREOF

RELATED APPLICATIONS

This application is a continuation of U.S. patent application Ser. No. 09/633,411, filed Aug. 7, 2000, now U.S. Pat. No. 6,476,019; which claims the benefit of priority to U.S. Provisional Patent Application Serial No. 60/148,918, filed Aug. 13, 1999.

BACKGROUND OF THE INVENTION

In 1976, Martin et al. (*J. Pharmacol. Exp. Ther.* 1976, 197, 517–32) postulated that sigma receptors account for the actions of (+/−)-SKF 10,047 (N-allyl-normetazocine) and related racemic benzomorphans. These compounds produce a spectrum of behaviors in the dog referred to as canine delirium and have psychotomimetic effects in humans. Great interest in the hypothesis of Martin et al. concerning sigma receptors led to intense scrutiny of (+/−)-SKF 10,047. Ten years of additional research revealed that (+/−)-SKF 10,047 binds to three types of receptors: (−)-SKF 10,047 binds primarily to mu and kappa opiate receptors; (+)-SKF 10,047 binds to PCP receptors and to a unique site that retains the designation sigma receptor (See Quirion et al. *Trends Neurosci.* 1987, 10, 444–46). Sigma receptors have also been called haloperidol-sensitive sigma receptors, etorphine-inaccessible sigma receptors, and naloxone-inaccessible sigma receptors (See Walker et al. *Neurology* 1988, 38, 961–65).

Sigma receptors were originally thought to be a type of opiate receptor, but two subsequent findings convincingly demonstrated that this characterization was incorrect: (a) whereas opiate receptors are enantioselective for the (−)-isomers of opium-derived narcotics, narcotic antagonists, and their congeners, sigma receptors are enantioselective for the (+)-isomers; and (b) naloxone is ineffective against both the in vivo and in vitro effects of sigma ligands. Therefore, it became clear that the sigma receptor is not a type of opiate receptor.

Initially, investigators asserted that sigma receptors were identical with PCP receptors, based on the displacement of [³H]PCP binding by the prototypic sigma ligand (+/−)-SKF 10,047. For this reason, sigma receptors were sometimes called "sigma opiate/PCP receptors". However, the drug selectivity pattern of [³H](+)-SKF 10,047 differs from that of [³H]PCP, showing that these substances bind to different receptors. For example, antipsychotic drugs (such as haloperidol) potently displace [³H](+)-SKF 10,047 binding, but they are weak or inactive against [³H]PCP binding. Conversely, PCP is weak antagonist of [³H]haloperidol binding.

Sigma and PCP receptors may also be differentiated by their distinct anatomical distributions, because [³H](+)-SKF 10,047 and [³H]PCP-binding sites are concentrated in different brain areas. Tam pointed out additional differences between [³H]PCP binding and [³H](+)-SKF 10,047 binding: the sensitivity of [³H]PCP binding to sodium ions; and the low affinity and small stereoselectivity shown by PCP receptors toward (+)-SKF 10,047 and (+)-ethylketocyclazocine. These findings showed that [³H](+)-SKF 10,047 binds to two distinct sites: a haloperidol-sensitive site (subsequently called the sigma receptor) and a PCP-sensitive site, subsequently called the PCP receptor.

Radioligand-binding studies revealed that many antipsychotic drugs bind to sigma receptors with high affinity. Haloperidol is among the most potent inhibitors of [³H](+)-SKF 10,047 binding, having a $K_i$ of 4 nM (Itzhak, Y. *Life Sci.* 1988, 42, 745–52). Other antipsychotic drugs that possess moderate ($K_i$<1000 nM) to high potency include perphenazine, (−)-butaclamol, acetophenazine, trifluoperazine, molindone, pimozide, thioridazine, and chlorpromazine (Tam and Cook *Proc. Natl. Acad. Sci. USA* 1984, 81, 5618–21). The connection between sigma receptors and antipsychotic drugs was further strengthened by the finding that [³H]haloperidol binding is strongly reduced by the sigma ligands (+)-SKF 10,047 (+)-pentazocine, and (+)-cyclazocine. In fact, the sigma ligand (+)-pentazocine displaces [³H]haloperidol from its binding sites in guinea pig brain about 10 times more potently than the dopamine ligand spiperone.

Furthermore, sigma receptors and kappa receptors have been shown to bind the same opiates. However, kappa receptors prefer one stereoisomer, and sigma receptors prefer the other. Whereas kappa opiate receptors bind (−)-benzomorphans, sigma receptors bind (+)-benzomorphans. Examples are (−)-SKF 10,047, (−)-pentazocine, and (−)-SKF 10,047, (−)-pentazocine, (−)-cyclazocine, and (−)-ethylketocyclazoine, which bind to kappa opiate receptors; their (+)-enantiomers bind to sigma receptors. Another example of this distiction is found with cis and trans isomers of U50,488. Whereas the trans isomers show preference for kappa opiate receptors, the cis isomers show preference for sigma receptors. Thus, in two chemically unrelated classes of compounds, different isomers show preference for kappa or sigma receptors. These results suggest a complimentarily between the topography of the binding sites of the kappa opiate and the sigma receptor.

Haloperidol exhibits its highest affinity to the sigma site, which is distinct from the classical opiate or phencyclidine sites. See Bartoszyk, G. D. et al. *CNS Drug Reviews* 1996, 2, 175–94. Functional connections between sigma receptors and dopaminergic neurons in mesolimbic and cortical areas have been identified, and the involvement of sigma sites in the action of antipsychotic drugs has been shown in animal experiments. Further evidence for the significance of sigma sites in schizophrenia comes from investigations showing that benzomorphans cause symptoms that resemble schizophrenia in humans. Finally, several post-mortem studies have shown that the number of sigma binding sites in cortical and cerebellar regions is reduced in schizophrenic patients. Some attempts have been made to develop novel antipsychotic drugs with selective affinity for the sigma receptor that would not have the extrapyramidal side effects (EPS) common to the classic neuroleptics. Among these drugs, rimcazole initially has been shown to have some efficacy in humans. However, such drugs retain EPS potential, and selective sigma ligands have ultimately not shown convincing antipsychotic efficacy in clinical trials. Drugs with greater selectivity for sigma receptors, or subtypes thereof, or drugs with higher intrinsic activity hold promise, e.g., as antipsychotics.

Following the discovery that sigma receptors bind antipsychotic drugs came the expected interest in the possible clinical significance of sigma ligands. Here the question of which effects of antipsychotic drugs may be mediated by sigma receptors becomes the central focus. The high concentration of sigma receptors in the motor system immediately raised the issue of the motor side effects of antipsychotic drugs. Simultaneously, the antipsychotic activity of sigma-active drugs such as haloperidol, coupled with the sigma-activity of rimcazole (a putative antipsychotic), raised the important question of the possiblity of novel sigma-binding antipsychotic drugs.

Several attempts have been made to formulate models of the sigma receptor that can explain the SAR data for various classes of sigma ligands. Largent et al. (*Mol. Pharmacol.* 1987, 32, 772–84) performed conformational calculations on a total of 10 compounds, which included phenothiazines and other structures, in an attempt to determine the interatomic distances between the N-(aromatic plane) and N-(polar function). The calculated energy-minimized conformations of (−)-cyclazocine, cis- and trans-clopenthixol, haloperidol, and (+)-dexclamol were found to match their X-ray crystal structure conformations. This study indicated several structural requirements for sigma binding. First, the primary pharmacophore at sigma sites appears to be the 3- or 4-phenylpiperidine moiety, which is present in most compounds showing high affinity for sigma receptors. Second, affinity is greatly influenced by large hydrophobic N-alkyl substituents. Third, compounds from many different structural classes exhibit substantial affinity for sigma receptors, indicating that certain interatomic distances are not subject to rigid constraint (e.g., N to aromatic ring).

In a markedly different approach to modeling the sigma receptor, Bowen et al. (*Eur. J. Pharmacol.* 1989, 163, 309–18) found evidence supporting a model of distinct, allosterically-coupled binding domains for non-benzomorphan sigma ligands and sigma-related (+)-benzomorphans. Studies of the sensitivity of rat brain sigma receptors to UV irradiation revealed unusual binding interactions of the various radiolabeled sigma probes. This study suggested that benzomorphan and non-benzomorphan sigma ligands interact with different sites on the receptor macromolecule that can be distinguished by differences in their sensitivities to UV light.

A model consistent with all the results cited above, and others not explicitly discussed, is one in which benzomorphans bind to a domain on the receptor macromolecule that is resistant to the effects of UV light. Furthermore, this domain is allosterically coupled to a binding domain for non-benzomorphans. The non-benzomorphan domain is sensitive to UV irradiation, perhaps because of the presence of a UV-sensitive residue such as tryptophan.

At the present time, there does not appear to be a unifying hypothesis capable of reconciling the different topographic and structural models of the sigma receptor. However, the evidence clearly points to interaction of sigma ligands with a heterogeneous population of sites. It is also important to note that one model does not necessarily preclude another. For example, it is conceivable that there are at least two sigma receptor macromolecules, one of which consists of distinct allosterically coupled binding sites, while the other consists of a single ligand binding domain. Additionally, superimposed on these general schemes might be subtle species or tissue differences in the structure of receptor proteins that might affect the ligand-binding profiles.

Sigma receptors are concentrated in (a) brainstem areas that primarily subserve motor functions, (b) certain limbic structures, (c) some predominantly sensory areas, and (d) brain areas associated with endocrine function. See McLean and Weber *Neuroscience* 1988, 25, 259–69. Sigma receptors are more concentrated in motor areas than in limbic areas. The distribution in the motor system is marked by the high densities found in brainstem motor circuits. For example, the cerebellum and its closely associated circuits, the red nucleus, inferior olive and locus coeruleus, are all rich in sigma receptors. Furthermore, sigma binding is found in cranial nerve nuclei that are rich in motor neurons (facial, motor trigeminal, hypoglossal, and oculomotor, as well as in the anterior horn of the spinal cord. These data form one of several lines of evidence for a function of the sigma receptor in motor function.

Several limbic structures are labeled by sigma radioligands. These areas include the cingulate cortex, lateral and medial septum, hippocampus, hypothalamus, parts of the limbic thalamus, habenula, and anterodorsal nucleus. The presence of sigma receptors in limbic systems might suggest a rule of sigma receptors in emotion and memory. Sigma receptors are found in certain areas that are clearly related to sensory processing. Most notable among these is the heavy labeling of dorsal root ganglia by [$^3$H](+)-3-PPP. See Gundlach et al. *J. Neurosci.* 1986, 6, 1757–70. The dorsal lateral geniculate and anterior pretectal areas (associated with visual information processing) are also heavily labeled by [$^3$H]DTG.

Although the brain distribution of sigma receptors is unique, some associations with the distribution of cholinergic neurons are notable. See Sofroniew et al. In *The Rat Nervous System*, vol. 1, pp. 471–85, Academic Press, NY, 1985. For example, sigma receptors are rich in cranial nerve motor nuclei, spinal ventral horns, dorsal diagonal band of Broca, and septal region, all of which possess cholinergic neurons. These two receptor systems do not overlap completely, however, because the caudate, which is rich in acetylcholine, has low levels of sigma receptors.

Sigma receptors are found in many areas of the brain associated with endorcrine function. The heavy labeling over the supraoptic and paraventricular nuclei within the hypothalamus suggests that sigma receptors participate in the regulation of vasopressin (and/or dynorphin) secretion. Dense labeling was also found in the adenohypophysis, suggesting regulation of anterior pituitary hormones. Using [$^3$H](+)-3-PPP, Jansen et al. (*Brain Res.* 1990, 507, 158–60) demonstrated high levels of sigma receptors in the rat pineal gland, again linking sigma receptors to endocrine function. The relation of sigma receptors to endorcrine function is further supported by the presence of sigma receptors in many peripheral endocrine tissues.

Cell surface proteins permit intracellular transduction of extracellular signals. Cell surface proteins provide eukaryotic, as well as prokaryotic, cells a means to detect extracellular signals and transduce such signals intracellularly in a manner that ultimately results in a cellular response or a concerted tissue or organ response. Cell surface proteins, by intracellularly transmitting information regarding the extracellular environment via specific intracellular pathways induce an appropriate response to a particular stimulus. The response may be immediate and transient, slow and sustained, or some mixture thereof. By virtue of an array of varied membrane surface proteins, eukaryotic cells are exquisitely sensitive to their environment.

Extracellular signal molecules, such as ligands for the sigma receptor, vasodilators and neurotransmitters, exert their effects, at least in part, via interaction with cell surface proteins. For example, some extracellular signal molecules cause changes in transcription of target gene via changes in the levels of secondary messengers, such as cAMP. Other signals, indirectly alter gene expression by activating the expression of genes, such as immediate-early genes that encode regulatory proteins, which in turn activate expression of other genes that encode transcriptional regulatory proteins. For example, neuron gene expression is modulated by numerous extracellular signals, including neurotransmitters and membrane electrical activity. Transsynaptic signals cause rapid responses in neurons that occur over a period of time ranging from milliseconds, such as the opening of ligand-gated channels, to seconds and minutes, such as second messenger-mediated events. Genes in neural cells that are responsive to transsynaptic stimulation and membrane electrical activity, include genes, called immediate early genes, whose transcription is activated rapidly, within minutes, and transiently (See, e.g., Sheng et al. (1990) Neuron 4: 477–485), and genes whose expression requires protein synthesis and whose expression is induced or altered over the course of hours.

Cell surface-localized receptors are membrane spanning proteins that bind extracellular signalling molecules or changes in the extracellular environment and transmit the signal via signal transduction pathways to effect a cellular response. Cell surface receptors bind circulating signal polypeptides, such as growth factors and hormones, as the initiating step in the induction of numerous intracellular pathways. Receptors are classified on the basis of the particular type of pathway that is induced. Included among these classes of receptors are those that bind growth factors and have intrinsic tyrosine kinase activity, such as the heparin binding growth factor (HBGF) receptors, and those that couple to effector proteins through guanine nucleotide binding regulatory proteins, which are referred to as G protein coupled receptors and G proteins, respectively.

G proteins play a central role in several types of signaling mechanisms (See Gilman, A. G. *Annu. Rev. Biochem.* 1987, 56, 615–49). In some systems, the first step in the cascade of biochemical events, from the formation of a transmitter-receptor complex to membrane conductance changes, is the coupling of the receptor to a G protein. G proteins play a role in cyclic adenosine monophosphate-related systems, PPI turnover, direct coupling to some ion channels, arachidonic acid-derived systems, and protein translocation (See Casey and Gilman, *J. Biol. Chem.* 1988, 263, 2577–80).

The G protein transmembrane signaling pathways consist of three proteins: receptors, G proteins and effectors. G proteins, which are the intermediaries in transmembrane signaling pathways, are heterodimers and consist of alpha, beta and gamma subunits. Among the members of a family of G proteins the alpha subunits differ. Functions of G proteins are regulated by the cyclic association of GTP with the alpha subunit followed by hydrolysis of GTP to GDP and dissociation of GDP.

G protein coupled receptors are a diverse class of receptors that mediate signal transduction by binding to G proteins. Signal transduction is initiated via ligand binding to the cell membrane receptor, which stimulates binding of the receptor to the G protein. The receptor G protein interaction releases GDP, which is specifically bound to the G protein, and permits the binding of GTP, which activates the G protein. Activated G protein dissociates from the receptor and activates the effector protein, which regulates the intracellular levels of specific second messengers. Examples of such effector proteins include adenyl cyclase, guanyl cyclase, phospholipase C, and others.

G protein-coupled receptors are known to be inducible. This inducibility was originally described in lower eukaryotes. For example, the cAMP receptor of the cellular slime mold, Dictyostelium, is induced during differentiation (Klein et al., Science 241: 1467–1472 (1988). During the Dictyostelium discoideum differentiation pathway, cAMP, induces high level expression of its G protein-coupled receptor. This receptor transduces the signal to induce the expression of the other genes involved in chemotaxis, which permits multicellular aggregates to align, organize and form stalks (see, Firtel, R. A., et al. Cell 58: 235–239 (1989) and Devreotes, P., Science 245: 1054–1058 (1989)).

Itzhak (See *Mol. Pharmacol.* 1989, 36, 512–17) reported evidence that sigma receptors interact with G proteins. As observed with other G protein-coupled receptors, guanosine triphosphate and Gpp(NY)p inhibited the binding of [$^3$H](+)-3-PPP to rat brain membranes. Binding of [$^3$H](+)-SKF 19 m946 was also inhibited but was less affected than [$^3$H](+)-3-PPP binding. Guanosine monophosphate and adenosine triphosphate had no effect on [$^3$H](+)-3-PPP binding, demonstrating specificity for G protein-active guanine nucleotides. Other agents known to affect receptor-G protein coupling also inhibited [$^3$H](+)-3-PPP binding. Treatment of rat brain membranes with either N-ethylmaleimide (a nonselective agent) or pertussis toxin (which selectively alters G proteins) significantly decreased [$^3$H](+)-3-PPP binding. These reagents also eliminated the effect of Gpp(NH)p on [$^3$H](+)-3-PPP binding. These results are similar to those obtained with other G protein-coupled receptors where these reagents are believed to cause uncoupling of the receptor from the G-protein unit.

Taken together, these results strongly suggest that the sigma receptor labeled by [$^3$H](+)-3-PPP can exist in a high and low affinity state, with the high affinity state coupled to a G protein. This suggestion has important implications for the function of sigma sites, because it suggests that sigma receptors are involved in signal transduction.

SUMMARY OF THE INVENTION

One aspect of the present invention relates to spirocyclic compounds. A second aspect of the present invention relates to the use of the spirocyclic compounds as ligands for various cellular receptors, including sigma receptors and G-protein-coupled receptors. Additional aspects of the present invention relate to the synthesis of combinatorial libraries of the spirocyclic compounds, and the screening of the libraries for biological activity, e.g., in assays based on sigma receptors or G-protein-coupled receptors.

DETAILED DESCRIPTION OF THE INVENTION

The present invention provides novel spirocyclic compounds, and combinatorial libraries thereof. Furthermore, the present invention provides spirocyclic compounds that are ligands for sigma receptors, and methods of use thereof in the treatment of conditions and diseases, wherein modulation of the activity of sigma receptors is likely to be beneficial to a subject. The present invention also relates to pharmaceutical compositions of the spirocycles.

The sigma ligands of the present invention represent new therapeutic entities in many conditions and diseases, including, but not limited to, inflammatory pain, neuropathic pain, multiple sclerosis, anxiety, depression, psychosis, stroke, motor neuron diseases, diseases associated with intraocular pressure, and glaucoma.

The ligands for sigma receptors of the present invention, in accord with eliprodil, are expected to enhance myelination in vitro. Therefore, the ligands may prove to be of therapeutic interest in demyelinating diseases like MS.

Additionally, compounds of the present invention can be tested in sigma receptor assays. Ligands for the sigma receptor can be useful as antipsychotic agents, as described in Abou-Gharbia et al., Annual Reports in Medicinal Chemistry, 28:1–10 (1993). The compounds of the invention show an especially advantageous affinity in vitro for sigma receptors, which is indicative of their usefulness in the prevention or treatment of neurological disorders and/or psychotic states The sigma receptor ligands of the present invention will be useful in the treatment of psychosis and movement disorders, such as dystonia and tardive dyskinesia, and motor disturbances associated with Huntington's chorea or Tourette's syndrome and in Parkinson's disease (Walker, J. M. et al, Pharmacological Reviews, 1990, 42, 355). It has been reported that the known sigma receptor ligand rimcazole clinically shows effects in the treatment of psychosis (Snyder, S. H., Largent, B. L. J. Neuro-psychiatry 1989, 1. 7) and that a group of sigma receptor ligands show antihallucinogenic activity in animal models (International Patent Publication No WO 9103243).

Furthermore, the ligands for sigma receptors of the present invention will be useful as therapeutic agents for cerebral neural function disorders such as dementia, depression, schizophrenia and anxiety neurosis, diseases accompanying abnormal immune response and cryptorrhea, digestive ulcer, etc. (Journal of Neuropsychiatry, 1, 7–15 (1989); Eur. J. Biochem., 200, 633–642 (1991); J. Pharmacol. Exp. Ther., 255, 1354–1359 (1990)).

The ligands for sigma receptors of the present invention will be useful as therapeutic agents for diseases in which sigma receptors are concerned, for example, cerebral neural function disorders such as dementia, depression, schizophrenia and anxiety neurosis, diseases accompanying abnormal immune response and cryptorrhea, digestive ulcer, etc.

The ligands for sigma receptors of the present invention will modulate the effects produced by the intervention of the NMDA receptor and act as antiischemic agents in vivo (Rao, T. S. et al., Molecular Pharmacology, 1990, 37, 978), with the possibility of use as neuroprotectors and in the treatment of epilepsy and of convulsion (Kaiser C., Neurotransmissions VII, 1991). It has been said that ligands for sigma receptors exhibit antiamnesic effects in animal models (Early et al., Brain Research, 1991, 546, 281). Additionally, sigma ligands, e.g., the compounds of the present invention, influence the levels of acetylcholine in animal models (Matsun et al., Brain Research 1992, 575, 315) and can consequently be used in the treatment of senile dementia, for example of Alzheimer type.

Definitions

For convenience, certain terms employed in the specification, examples, and appended claims are collected here.

The term "cell surface proteins" includes molecules that occur on the surface of cells, interact with the extracellular environment, and transmit or transduce information regarding the environment intracellularly.

The term "extracellular signals" includes a molecule or a change in the environment that is transduced intracellularly via cell surface proteins that interact, directly or indirectly, with the signal. An extracellular signal is any compound or substance that in some manner specifically alters the activity of a cell surface protein. Examples of such signals include, but are not limited to, molecules such as acetylcholine, growth factors, hormones and other mitogenic substances, such as phorbol mistric acetate (PMA), that bind to cell surface receptors and ion channels and modulate the activity of such receptors and channels. Extracellular signals also includes as yet unidentified substances that modulate the activity of a cell surface protein and thereby affect intracellular functions and that are potential pharmacological agents that may be used to treat specific diseases by modulating the activity of specific cell surface receptors.

The term "$ED_{50}$" means the dose of a drug which produces 50% of its maximum response or effect. Alternatively, the dose which produces a pre-determined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

The term "structure-activity relationship (SAR)" refers to the way in which altering the molecular structure of drugs alters their interaction with a receptor, enzyme, etc.

The term "agonist" refers to a compound that mimics the action of natural transmitter or, when the natural transmitter is not known, causes changes at the receptor complex in the absence of other receptor ligands.

The term "antagonist" refers to a compound that binds to a receptor site, but does not cause any physiological changes unless another receptor ligand is present.

The term "competitive antagonist" refers to a compound that binds to a receptor site; its effects can be overcome by increased concentration of the agonist.

The term "partial agonist" refers to a compound that binds to a receptor site but does not produce the maximal effect regardless of its concentration.

The term "ligand" refers to a compound that binds at the receptor site.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, anido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "spirocycle" and "spirocyclic" refer to compounds or moieties wherein two rings have in common only a single carbon or silicon atom.

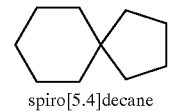

spiro[5.4]decane

The term "carbocycle", as used herein, refers to an aromatic or non-aromatic ring in which each atom of the ring is carbon.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

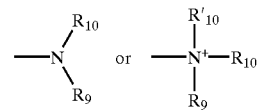

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

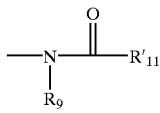

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

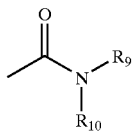

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

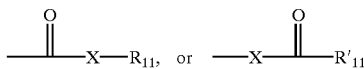

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

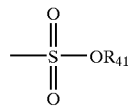

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutane-sulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

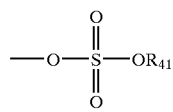

in which $R_{41}$ is as defined above.

The term "sulfonamido" is art recognized and includes a moiety that can be represented by the general formula:

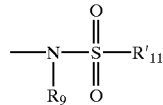

in which $R_9$ and $R'_{11}$ are as defined above.

The term "sulfamoyl" is art-recognized and includes a moiety that can be represented by the general formula:

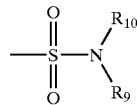

in which $R_9$ and $R_{10}$ are as defined above.

The term "sulfonyl", as used herein, refers to a moiety that can be represented by the general formula:

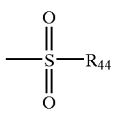

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

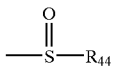

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

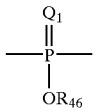

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

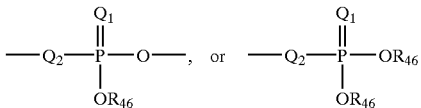

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, 2nd* ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to sigma receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Compounds of the Invention.

In certain embodiments, the compounds of the present invention are represented by structure 1:

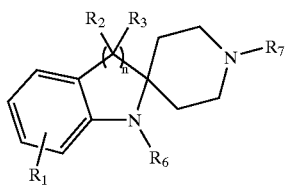

wherein
- R represents independently for each occurrence hydrogen, alkyl, aryl, heteroaryl, aralkyl, or heteroaralkyl;
- $R_1$ is absent, or present between 1 and 4 times;
- $R_1$ represents independently for each occurrence halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, aralkyl, heteroaralkyl, azide, aziridine, carbamate, epoxide, hydroxamic acid, imide, oxime, sulfonamide, thioamide, thiocarbamate, urea, thiourea, or —$(CH_2)_m$—$R_{80}$;
- $R_2$ and $R_3$ represent independently for each occurrence hydrogen, alkyl, aryl, heteroaryl, aralkyl, heteroaralkyl, OR, $N(R)_2$, $CO_2R$, $C(O)N(R)_2$, $OC(O)R$, or $N(R)C(O)R$; or two geminal instances of $R_2$ and $R_3$ taken together may represent O or $C(R)_2$;
- $R_6$ represents hydrogen, alkyl, aryl, heteroaryl, aralkyl, heteroaralkyl, acyl, C(O)OR, $C(O)N(R)_2$, or $SO_2R$;
- $R_7$ represents hydrogen, alkyl, alkenyl, aryl, heteroaryl, aralkyl, heteroaralkyl, acyl, C(O)OR, $C(O)N(R)_2$, or $SO_2R$;
- $R_{80}$ represents an aryl, cycloalkyl, cycloalkenyl, heterocyclyl, or polycyclyl group;
- m is an integer in the range 0 to 8 inclusive; and
- n is 1, 2, or 3;
- provided that when n is 3 and a pair of geminal instances of $R_2$ and $R_3$ taken together represent O, $R_7$ is not acetyl;
- further provided that when n is 2, $R_2$ and $R_3$ are not both methyl; or when n is 2, $R_6$ and $R_7$ are not both acetyl.

In certain embodiments, the compounds of the present invention are represented by structure 1 and the attendant definitions, wherein $R_1$ represents independently for each occurrence OR, $N(R)_2$, halogen, $CO_2R$, $CON(R)_2$, $OCF_3$, CN, or $CF_3$.

In certain embodiments, the compounds of the present invention are represented by structure 1 and the attendant definitions, wherein $R_1$ represents independently for each occurrence OR, halogen, or $CF_3$.

In certain embodiments, the compounds of the present invention are represented by structure 1 and the attendant definitions, wherein $R_2$ and $R_3$ represent independently for each occurrence H, OR, or $N(R)_2$.

In certain embodiments, the compounds of the present invention are represented by structure 1 and the attendant definitions, wherein at least one pair of geminal instances of $R_2$ and $R_3$ taken together represent O.

In certain embodiments, the compounds of the present invention are represented by structure 1 and the attendant definitions, wherein $R_6$ represents H, alkyl or acyl.

In certain embodiments, the compounds of the present invention are represented by structure 1 and the attendant definitions, wherein $R_7$ represents H, alkyl or aralkyl.

In certain embodiments, the compounds of the present invention are represented by structure 1 and the attendant definitions, wherein $R_1$ represents independently for each occurrence OR, $N(R)_2$, halogen, $CO_2R$, $CON(R)_2$, $OCF_3$, CN, or $CF_3$; and $R_2$ and $R_3$ represent independently for each occurrence H, OR, or $N(R)_2$.

In certain embodiments, the compounds of the present invention are represented by structure 1 and the attendant definitions, wherein $R_1$ represents independently for each occurrence OR, $N(R)_2$, halogen, $CO_2R$, $CON(R)_2$, $OCF_3$, CN, or $CF_3$; and at least one pair of geminal instances of $R_2$ and $R_3$ taken together represent O.

In certain embodiments, the compounds of the present invention are represented by structure 1 and the attendant definitions, wherein $R_1$ represents independently for each occurrence OR, $N(R)_2$, halogen, $CO_2R$, $CON(R)_2$, $OCF_3$, CN, or $CF_3$; $R_2$ and $R_3$ represent independently for each occurrence H, OR, or $N(R)_2$; and $R_6$ represents H, alkyl or acyl.

In certain embodiments, the compounds of the present invention are represented by structure 1 and the attendant definitions, wherein $R_1$ represents independently for each occurrence OR, $N(R)_2$, halogen, $CO_2R$, $CON(R)_2$, $OCF_3$, CN, or $CF_3$; at least one pair of geminal instances of $R_2$ and $R_3$ taken together represent O; and $R_6$ represents H, alkyl or acyl.

In certain embodiments, the compounds of the present invention are represented by structure 1 and the attendant definitions, wherein $R_1$ represents independently for each occurrence OR, halogen, or $CF_3$; and $R_2$ and $R_3$ represent independently for each occurrence H, OR, or $N(R)_2$.

In certain embodiments, the compounds of the present invention are represented by structure 1 and the attendant definitions, wherein $R_1$ represents independently for each occurrence OR, halogen, or $CF_3$; and at least one pair of geminal instances of $R_2$ and $R_3$ taken together represent O.

In certain embodiments, the compounds of the present invention are represented by structure 1 and the attendant definitions, wherein $R_1$ represents independently for each occurrence OR, halogen, or $CF_3$; $R_2$ and $R_3$ represent independently for each occurrence H, OR, or $N(R)_2$; and $R_6$ represents H, alkyl or acyl.

In certain embodiments, the compounds of the present invention are represented by structure 1 and the attendant definitions, wherein $R_1$ represents independently for each occurrence OR, halogen, or $CF_3$; at least one pair of geminal instances of $R_2$ and $R_3$ taken together represent O; and $R_6$ represents H, alkyl or acyl.

In certain assays based on mammalian G-protein-coupled receptors or sigma receptors, certain compounds according to general structure 1 have $IC_{50}$ values less than 10 μM, more preferably less than 1 μM, and most preferably less than 0.1 μM.

In certain embodiments, the compounds of the present invention are represented by structure 2:

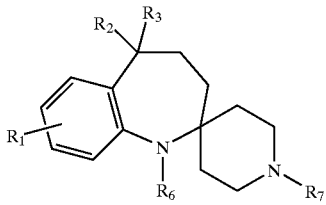

wherein
R represents independently for each occurrence hydrogen, alkyl, aryl, heteroaryl, aralkyl, or heteroaralkyl;
$R_1$ is absent, or present between 1 and 4 times;
$R_1$ represents independently for each occurrence halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, aralkyl, heteroaralkyl, azide, aziridine, carbamate, epoxide, hydroxamic acid, imide, oxime, sulfonamide, thioamide, thiocarbamate, urea, thiourea, or $-(CH_2)_m-R_{80}$;
$R_2$ and $R_3$ represent independently for each occurrence hydrogen, alkyl, aryl, heteroaryl, aralkyl, heteroaralkyl, OR, $N(R)_2$, $CO_2R$, $C(O)N(R)_2$, $OC(O)R$, or $N(R)C(O)R$; or the geminal instances of $R_2$ and $R_3$ taken together may represent O or $C(R)_2$;
$R_6$ represents hydrogen, alkyl, aryl, heteroaryl, aralkyl, heteroaralkyl, acyl, $C(O)OR$, $C(O)N(R)_2$, or $SO_2R$;
$R_7$ represents hydrogen, alkyl, alkenyl, aryl, heteroaryl, aralkyl, heteroaralkyl, acyl, $C(O)OR$, $C(O)N(R)_2$, or $SO_2R$;
$R_{80}$ represents an aryl, cycloalkyl, cycloalkenyl, heterocyclyl, or polycyclyl group; and
m is an integer in the range 0 to 8 inclusive;
provided that when the geminal instances of $R_2$ and $R_3$ taken together represent O, $R_7$ is not acetyl.

In certain embodiments, the compounds of the present invention are represented by structure 2 and the attendant definitions, wherein $R_1$ represents independently for each occurrence OR, $N(R)_2$, halogen, $CO_2R$, $CON(R)_2$, $OCF_3$, CN, or $CF_3$.

In certain embodiments, the compounds of the present invention are represented by structure 2 and the attendant definitions, wherein $R_1$ represents independently for each occurrence OR, halogen, or $CF_3$.

In certain embodiments, the compounds of the present invention are represented by structure 2 and the attendant definitions, wherein $R_2$ and $R_3$ represent independently for each occurrence H, OR, or $N(R)_2$.

In certain embodiments, the compounds of the present invention are represented by structure 2 and the attendant definitions, wherein the geminal instances of $R_2$ and $R_3$ taken together represent O.

In certain embodiments, the compounds of the present invention are represented by structure 2 and the attendant definitions, wherein $R_6$ represents H, alkyl or acyl.

In certain embodiments, the compounds of the present invention are represented by structure 2 and the attendant definitions, wherein $R_7$ represents H, alkyl or aralkyl.

In certain embodiments, the compounds of the present invention are represented by structure 2 and the attendant definitions, wherein $R_1$ represents independently for each occurrence OR, $N(R)_2$, halogen, $CO_2R$, $CON(R)_2$, $OCF_3$, CN, or $CF_3$; and $R_2$ and $R_3$ represent independently for each occurrence H, OR, or $N(R)_2$.

In certain embodiments, the compounds of the present invention are represented by structure 2 and the attendant definitions, wherein $R_1$ represents independently for each occurrence OR, $N(R)_2$, halogen, $CO_2R$, $CON(R)_2$, $OCF_3$, CN, or $CF_3$; and the geminal instances of $R_2$ and $R_3$ taken together represent O.

In certain embodiments, the compounds of the present invention are represented by structure 2 and the attendant definitions, wherein $R_1$ represents independently for each occurrence OR, $N(R)_2$, halogen, $CO_2R$, $CON(R)_2$, $OCF_3$, CN, or $CF_3$; $R_2$ and $R_3$ represent independently for each occurrence H, OR, or $N(R)_2$; and $R_6$ represents H, alkyl or acyl.

In certain embodiments, the compounds of the present invention are represented by structure 2 and the attendant definitions, wherein $R_1$ represents independently for each occurrence OR, $N(R)_2$, halogen, $CO_2R$, $CON(R)_2$, $OCF_3$, CN, or $CF_3$; the geminal instances of $R_2$ and $R_3$ taken together represent O; and $R_6$ represents H, alkyl or acyl.

In certain embodiments, the compounds of the present invention are represented by structure 2 and the attendant definitions, wherein $R_1$ represents independently for each occurrence OR, halogen, or $CF_3$; and $R_2$ and $R_3$ represent independently for each occurrence H, OR, or $N(R)_2$.

In certain embodiments, the compounds of the present invention are represented by structure 2 and the attendant definitions, wherein $R_1$ represents independently for each occurrence OR, halogen, or $CF_3$; and the geminal instances of $R_2$ and $R_3$ taken together represent O.

In certain embodiments, the compounds of the present invention are represented by structure 2 and the attendant definitions, wherein $R_1$ represents independently for each occurrence OR, halogen, or $CF_3$; $R_2$ and $R_3$ represent independently for each occurrence H, OR, or $N(R)_2$; and $R_6$ represents H, alkyl or acyl.

In certain embodiments, the compounds of the present invention are represented by structure 2 and the attendant definitions, wherein $R_1$ represents independently for each occurrence OR, halogen, or $CF_3$; the geminal instances of $R_2$ and $R_3$ taken together represent O; and $R_6$ represents H, alkyl or acyl.

In certain assays based on mammalian G-protein-coupled receptors or sigma receptors, certain compounds according to general structure 2 have $IC_{50}$ values less than 10 $\mu$M, more preferably less than 1 $\mu$M, and most preferably less than 0.1 $\mu$M.

In certain embodiments, the compounds of the present invention are represented by structure 3:

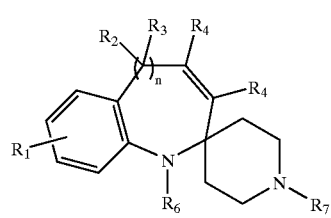

wherein
R represents independently for each occurrence hydrogen, alkyl, aryl, heteroaryl, aralkyl, or heteroaralkyl;
$R_1$ is absent, or present between 1 and 4 times;

$R_1$ represents independently for each occurrence halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, aralkyl, heteroaralkyl, azide, aziridine, carbamate, epoxide, hydroxamic acid, imide, oxime, sulfonamide, thioamide, thiocarbamate, urea, thiourea, or —$(CH_2)_m$—$R_{80}$;

$R_2$ and $R_3$ represent independently for each occurrence hydrogen, alkyl, aryl, heteroaryl, aralkyl, heteroaralkyl, OR, $N(R)_2$, $CO_2R$, $C(O)N(R)_2$, $OC(O)R$, or $N(R)C(O)R$; or the geminal instances of $R_2$ and $R_3$ taken together may represent O or $C(R)_2$;

$R_4$ represents independently for each occurrence H or alkyl;

$R_6$ represents hydrogen, alkyl, aryl, heteroaryl, aralkyl, heteroaralkyl, acyl, C(O)OR, $C(O)N(R)_2$, or $SO_2R$;

$R_7$ represents hydrogen, alkyl, alkenyl, aryl, heteroaryl, aralkyl, heteroaralkyl, acyl, C(O)OR, $C(O)N(R)_2$, or $SO_2R$;

$R_{80}$ represents an aryl, cycloalkyl, cycloalkenyl, heterocyclyl, or polycyclyl group;

m is an integer in the range 0 to 8 inclusive; and n is 0 or 1;

provided that when the geminal instances of $R_2$ and $R_3$ taken together represent O, $R_7$ is not acetyl.

In certain embodiments, the compounds of the present invention are represented by structure 3 and the attendant definitions, wherein $R_1$ represents independently for each occurrence OR, $N(R)_2$, halogen, $CO_2R$, $CON(R)_2$, $OCF_3$, CN, or $CF_3$.

In certain embodiments, the compounds of the present invention are represented by structure 3 and the attendant definitions, wherein $R_1$ represents independently for each occurrence OR, halogen, or $CF_3$.

In certain embodiments, the compounds of the present invention are represented by structure 3 and the attendant definitions, wherein $R_2$ and $R_3$ represent independently for each occurrence H, OR, or $N(R)_2$.

In certain embodiments, the compounds of the present invention are represented by structure 3 and the attendant definitions, wherein the geminal instances of $R_2$ and $R_3$ taken together represent O.

In certain embodiments, the compounds of the present invention are represented by structure 3 and the attendant definitions, wherein $R_4$ represents independently for each occurrence H.

In certain embodiments, the compounds of the present invention are represented by structure 3 and the attendant definitions, wherein $R_6$ represents H, alkyl or acyl.

In certain embodiments, the compounds of the present invention are represented by structure 3 and the attendant definitions, wherein $R_7$ represents H, alkyl or aralkyl.

In certain embodiments, the compounds of the present invention are represented by structure 3 and the attendant definitions, wherein $R_1$ represents independently for each occurrence OR, $N(R)_2$, halogen, $CO_2R$, $CON(R)_2$, $OCF_3$, CN, or $CF_3$; and $R_2$ and $R_3$ represent independently for each occurrence H, OR, or $N(R)_2$.

In certain embodiments, the compounds of the present invention are represented by structure 3 and the attendant definitions, wherein $R_1$ represents independently for each occurrence OR, $N(R)_2$, halogen, $CO_2R$, $CON(R)_2$, $OCF_3$, CN, or $CF_3$; and the geminal instances of $R_2$ and $R_3$ taken together represent O.

In certain embodiments, the compounds of the present invention are represented by structure 3 and the attendant definitions, wherein $R_1$ represents independently for each occurrence OR, $N(R)_2$, halogen, $CO_2R$, $CON(R)_2$, $OCF_3$, CN, or $CF_3$; $R_2$ and $R_3$ represent independently for each occurrence H, OR, or $N(R)_2$; and $R_6$ represents H, alkyl or acyl.

In certain embodiments, the compounds of the present invention are represented by structure 3 and the attendant definitions, wherein $R_1$ represents independently for each occurrence OR, $N(R)_2$, halogen, $CO_2R$, $CON(R)_2$, $OCF_3$, CN, or $CF_3$; the geminal instances of $R_2$ and $R_3$ taken together represent O; and $R_6$ represents H, alkyl or acyl.

In certain embodiments, the compounds of the present invention are represented by structure 3 and the attendant definitions, wherein $R_1$ represents independently for each occurrence OR, $N(R)_2$, halogen, $CO_2R$, $CON(R)_2$, $OCF_3$, CN, or $CF_3$; $R_2$ and $R_3$ represent independently for each occurrence H, OR, or $N(R)_2$; $R_6$ represents H, alkyl or acyl; and $R_7$ represents H, alkyl or aralkyl.

In certain embodiments, the compounds of the present invention are represented by structure 3 and the attendant definitions, wherein $R_1$ represents independently for each occurrence OR, $N(R)_2$, halogen, $CO_2R$, $CON(R)_2$, $OCF_3$, CN, or $CF_3$; the geminal instances of $R_2$ and $R_3$ taken together represent O; $R_6$ represents H, alkyl or acyl; and $R_7$ represents H, alkyl or aralkyl.

In certain embodiments, the compounds of the present invention are represented by structure 3 and the attendant definitions, wherein $R_1$ represents independently for each occurrence OR, halogen, or $CF_3$; and $R_2$ and $R_3$ represent independently for each occurrence H, OR, or $N(R)_2$.

In certain embodiments, the compounds of the present invention are represented by structure 3 and the attendant definitions, wherein $R_1$ represents independently for each occurrence OR, halogen, or $CF_3$; and the geminal instances of $R_2$ and $R_3$ taken together represent O.

In certain embodiments, the compounds of the present invention are represented by structure 3 and the attendant definitions, wherein $R_1$ represents independently for each occurrence OR, halogen, or $CF_3$; $R_2$ and $R_3$ represent independently for each occurrence H, OR, or $N(R)_2$; and $R_6$ represents H, alkyl or acyl.

In certain embodiments, the compounds of the present invention are represented by structure 3 and the attendant definitions, wherein $R_1$ represents independently for each occurrence OR, halogen, or $CF_3$; the geminal instances of $R_2$ and $R_3$ taken together represent O; and $R_6$ represents H, alkyl or acyl.

In certain embodiments, the compounds of the present invention are represented by structure 3 and the attendant definitions, wherein $R_1$ represents independently for each occurrence OR, halogen, or $CF_3$; $R_2$ and $R_3$ represent independently for each occurrence H, OR, or $N(R)_2$; $R_6$ represents H, alkyl or acyl; and $R_7$ represents H, alkyl or aralkyl.

In certain embodiments, the compounds of the present invention are represented by structure 3 and the attendant definitions, wherein $R_1$ represents independently for each occurrence OR, halogen, or $CF_3$; the geminal instances of $R_2$ and $R_3$ taken together represent O; $R_6$ represents H, alkyl or acyl; and $R_7$ represents H, alkyl or aralkyl.

In certain assays based on mammalian G-protein-coupled receptors or sigma receptors, certain compounds according to general structure 3 have IC$_{50}$ values less than 10 μM, more preferably less than 1 μM, and most preferably less than 0.1 μM.

In certain embodiments, the compounds of the present invention are represented by structure 4:

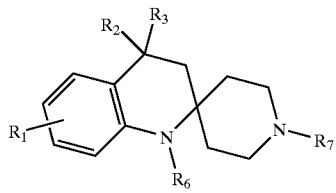

4 wherein
- R represents independently for each occurrence hydrogen, alkyl, aryl, heteroaryl, aralkyl, or heteroaralkyl;
- R$_1$ is absent, or present between 1 and 4 times;
- R$_1$ represents independently for each occurrence halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, aralkyl, heteroaralkyl, azide, aziridine, carbamate, epoxide, hydroxamic acid, imide, oxime, sulfonamide, thioamide, thiocarbamate, urea, thiourea, or —(CH$_2$)$_m$—R$_{80}$;
- R$_2$ and R$_3$ represent independently for each occurrence hydrogen, alkyl, aryl, heteroaryl, aralkyl, heteroaralkyl, OR, N(R)$_2$, CO$_2$R, C(O)N(R)$_2$, OC(O)R, or N(R)C(O)R; or the geminal instances of R$_2$ and R$_3$ taken together may represent O or C(R)$_2$;
- R$_6$ represents hydrogen, alkyl, aryl, heteroaryl, aralkyl, heteroaralkyl, acyl, C(O)OR, C(O)N(R)$_2$, or SO$_2$R;
- R$_7$ represents hydrogen, alkyl, alkenyl, aryl, heteroaryl, aralkyl, heteroaralkyl, acyl, C(O)OR, C(O)N(R)$_2$, or SO$_2$R;
- R$_{80}$ represents an aryl, cycloalkyl, cycloalkenyl, heterocyclyl, or polycyclyl group; and
- m is an integer in the range 0 to 8 inclusive;
- provided that R$_2$ and R$_3$ are not both methyl; or R$_6$ and R$_7$ are not both acetyl.

In certain embodiments, the compounds of the present invention are represented by structure 4 and the attendant definitions, wherein R$_1$ represents independently for each occurrence OR, N(R)$_2$, halogen, CO$_2$R, CON(R)$_2$, OCF$_3$, CN, or CF$_3$.

In certain embodiments, the compounds of the present invention are represented by structure 4 and the attendant definitions, wherein R$_1$ represents independently for each occurrence OR, halogen, or CF$_3$.

In certain embodiments, the compounds of the present invention are represented by structure 4 and the attendant definitions, wherein R$_2$ and R$_3$ represent independently for each occurrence H, OR, or N(R)$_2$.

In certain embodiments, the compounds of the present invention are represented by structure 4 and the attendant definitions, wherein the geminal instances of R$_2$ and R$_3$ taken together represent O.

In certain embodiments, the compounds of the present invention are represented by structure 4 and the attendant definitions, wherein R$_6$ represents H, alkyl or acyl.

In certain embodiments, the compounds of the present invention are represented by structure 4 and the attendant definitions, wherein R$_7$ represents H, alkyl or aralkyl.

In certain embodiments, the compounds of the present invention are represented by structure 4 and the attendant definitions, wherein R$_1$ represents independently for each occurrence OR, N(R)$_2$, halogen, CO$_2$R, CON(R)$_2$, OCF$_3$, CN, or CF$_3$; and R$_2$ and R$_3$ represent independently for each occurrence H, OR, or N(R)$_2$.

In certain embodiments, the compounds of the present invention are represented by structure 4 and the attendant definitions, wherein R$_1$ represents independently for each occurrence OR, N(R)$_2$, halogen, CO$_2$R, CON(R)$_2$, OCF$_3$, CN, or CF$_3$; and the geminal instances of R$_2$ and R$_3$ taken together represent O.

In certain embodiments, the compounds of the present invention are represented by structure 4 and the attendant definitions, wherein R$_1$ represents independently for each occurrence OR, N(R)$_2$, halogen, CO$_2$R, CON(R)$_2$, OCF$_3$, CN, or CF$_3$; R$_2$ and R$_3$ represent independently for each occurrence H, OR, or N(R)$_2$; and R$_6$ represents H, alkyl or acyl.

In certain embodiments, the compounds of the present invention are represented by structure 4 and the attendant definitions, wherein R$_1$ represents independently for each occurrence OR, N(R)$_2$, halogen, CO$_2$R, CON(R)$_2$, OCF$_3$, CN, or CF$_3$; the geminal instances of R$_2$ and R$_3$ taken together represent O; and R$_6$ represents H, alkyl or acyl.

In certain embodiments, the compounds of the present invention are represented by structure 4 and the attendant definitions, wherein R$_1$ represents independently for each occurrence OR, N(R)$_2$, halogen, CO$_2$R, CON(R)$_2$, OCF$_3$, CN, or CF$_3$; R$_2$ and R$_3$ represent independently for each occurrence H, OR, or N(R)$_2$; R$_6$ represents H, alkyl or acyl; and R$_7$ represents H, alkyl or aralkyl.

In certain embodiments, the compounds of the present invention are represented by structure 4 and the attendant definitions, wherein R$_1$ represents independently for each occurrence OR, N(R)$_2$, halogen, CO$_2$R, CON(R)$_2$, OCF$_3$, CN, or CF$_3$; the geminal instances of R$_2$ and R$_3$ taken together represent O; R$_6$ represents H, alkyl or acyl; and R$_7$ represents H, alkyl or aralkyl.

In certain embodiments, the compounds of the present invention are represented by structure 4 and the attendant definitions, wherein R$_1$ represents independently for each occurrence OR, halogen, or CF$_3$; and R$_2$ and R$_3$ represent independently for each occurrence H, OR, or N(R)$_2$.

In certain embodiments, the compounds of the present invention are represented by structure 4 and the attendant definitions, wherein R$_1$ represents independently for each occurrence OR, halogen, or CF$_3$; and the geminal instances of R$_2$ and R$_3$ taken together represent O.

In certain embodiments, the compounds of the present invention are represented by structure 4 and the attendant definitions, wherein R$_1$ represents independently for each occurrence OR, halogen, or CF$_3$; R$_2$ and R$_3$ represent independently for each occurrence H, OR, or N(R)$_2$; and R$_6$ represents H, alkyl or acyl.

In certain embodiments, the compounds of the present invention are represented by structure 4 and the attendant definitions, wherein R$_1$ represents independently for each occurrence OR, halogen, or CF$_3$; the geminal instances of R$_2$ and R$_3$ taken together represent O; and R$_6$ represents H, alkyl or acyl.

In certain embodiments, the compounds of the present invention are represented by structure 4 and the attendant definitions, wherein R$_1$ represents independently for each occurrence OR, halogen, or $CF_3$; $R_2$ and $R_3$ represent independently for each occurrence H, OR, or $N(R)_2$; $R_6$ represents H, alkyl or acyl; and $R_7$ represents H, alkyl or aralkyl.

In certain embodiments, the compounds of the present invention are represented by structure 4 and the attendant definitions, wherein $R_1$ represents independently for each occurrence OR, halogen, or $CF_3$; the geminal instances of $R_2$ and $R_3$ taken together represent O; $R_6$ represents H, alkyl or acyl; and $R_7$ represents H, alkyl or aralkyl.

In certain assays based on mammalian G-protein-coupled receptors or sigma receptors, certain compounds according to general structure 4 have $IC_{50}$ values less than 10 μM, more preferably less than 1 μM, and most preferably less than 0.1 μM.

In certain embodiments, the compounds of the present invention are represented by structure 5:

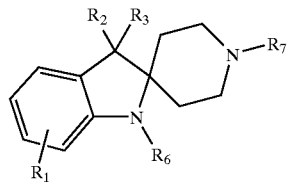

5 wherein

R represents independently for each occurrence hydrogen, alkyl, aryl, heteroaryl, aralkyl, or heteroaralkyl;

$R_1$ is absent, or present between 1 and 4 times;

$R_1$ represents independently for each occurrence halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, aralkyl, heteroaralkyl, azide, aziridine, carbamate, epoxide, hydroxamic acid, imide, oxime, sulfonamide, thioamide, thiocarbamate, urea, thiourea, or $-(CH_2)_m-R_{80}$;

$R_2$ and $R_3$ represent independently for each occurrence hydrogen, alkyl, aryl, heteroaryl, aralkyl, heteroaralkyl, OR, $N(R)_2$, $CO_2R$, $C(O)N(R)_2$, $OC(O)R$, or $N(R)C(O)R$; or the geminal instances of $R_2$ and $R_3$ taken together may represent O or $C(R)_2$;

$R_6$ represents hydrogen, alkyl, aryl, heteroaryl, aralkyl, heteroaralkyl, acyl, $C(O)OR$, $C(O)N(R)_2$, or $SO_2R$;

$R_7$ represents hydrogen, alkyl, alkenyl, aryl, heteroaryl, aralkyl, heteroaralkyl, acyl, $C(O)OR$, $C(O)N(R)_2$, or $SO_2R$;

$R_{80}$ represents an aryl, cycloalkyl, cycloalkenyl, heterocyclyl, or polycyclyl group; and m is an integer in the range 0 to 8 inclusive.

In certain embodiments, the compounds of the present invention are represented by structure 5 and the attendant definitions, wherein $R_1$ represents independently for each occurrence OR, $N(R)_2$, halogen, $CO_2R$, $CON(R)_2$, $OCF_3$, CN, or $CF_3$.

In certain embodiments, the compounds of the present invention are represented by structure 5 and the attendant definitions, wherein $R_1$ represents independently for each occurrence OR, halogen, or $CF_3$.

In certain embodiments, the compounds of the present invention are represented by structure 5 and the attendant definitions, wherein $R_2$ and $R_3$ represent independently for each occurrence H, OR, or $N(R)_2$.

In certain embodiments, the compounds of the present invention are represented by structure 5 and the attendant definitions, wherein the geminal instances of $R_2$ and $R_3$ taken together represent O.

In certain embodiments, the compounds of the present invention are represented by structure 5 and the attendant definitions, wherein $R_6$ represents H, alkyl or acyl.

In certain embodiments, the compounds of the present invention are represented by structure 5 and the attendant definitions, wherein $R_7$ represents H, alkyl or aralkyl.

In certain embodiments, the compounds of the present invention are represented by structure 5 and the attendant definitions, wherein $R_1$ represents independently for each occurrence OR, $N(R)_2$, halogen, $CO_2R$, $CON(R)_2$, $OCF_3$, CN, or $CF_3$; and $R_2$ and $R_3$ represent independently for each occurrence H, OR, or $N(R)_2$.

In certain embodiments, the compounds of the present invention are represented by structure 5 and the attendant definitions, wherein $R_1$ represents independently for each occurrence OR, $N(R)_2$, halogen, $CO_2R$, $CON(R)_2$, $OCF_3$, CN, or $CF_3$; and the geminal instances of $R_2$ and $R_3$ taken together represent O.

In certain embodiments, the compounds of the present invention are represented by structure 5 and the attendant definitions, wherein $R_1$ represents independently for each occurrence OR, $N(R)_2$, halogen, $CO_2R$, $CON(R)_2$, $OCF_3$, CN, or $CF_3$; $R_2$ and $R_3$ represent independently for each occurrence H, OR, or $N(R)_2$; and $R_6$ represents H, alkyl or acyl.

In certain embodiments, the compounds of the present invention are represented by structure 5 and the attendant definitions, wherein $R_1$ represents independently for each occurrence OR, $N(R)_2$, halogen, $CO_2R$, $CON(R)_2$, $OCF_3$, CN, or $CF_3$; the geminal instances of $R_2$ and $R_3$ taken together represent O; and $R_6$ represents H, alkyl or acyl.

In certain embodiments, the compounds of the present invention are represented by structure 5 and the attendant definitions, wherein $R_1$ represents independently for each occurrence OR, $N(R)_2$, halogen, $CO_2R$, $CON(R)_2$, $OCF_3$, CN, or $CF_3$; $R_2$ and $R_3$ represent independently for each occurrence H, OR, or $N(R)_2$; $R_6$ represents H, alkyl or acyl; and $R_7$ represents H, alkyl or aralkyl.

In certain embodiments, the compounds of the present invention are represented by structure 5 and the attendant definitions, wherein $R_1$ represents independently for each occurrence OR, $N(R)_2$, halogen, $CO_2R$, $CON(R)_2$, $OCF_3$, CN, or $CF_3$; the geminal instances of $R_2$ and $R_3$ taken together represent O; $R_6$ represents H, alkyl or acyl; and $R_7$ represents H, alkyl or aralkyl.

In certain embodiments, the compounds of the present invention are represented by structure 5 and the attendant definitions, wherein $R_1$ represents independently for each occurrence OR, halogen, or $CF_3$; and $R_2$ and $R_3$ represent independently for each occurrence H, OR, or $N(R)_2$.

In certain embodiments, the compounds of the present invention are represented by structure 5 and the attendant definitions, wherein $R_1$ represents independently for each occurrence OR, halogen, or $CF_3$; and the geminal instances of $R_2$ and $R_3$ taken together represent O.

In certain embodiments, the compounds of the present invention are represented by structure 5 and the attendant definitions, wherein $R_1$ represents independently for each occurrence OR, halogen, or $CF_3$; $R_2$ and $R_3$ represent independently for each occurrence H, OR, or $N(R)_2$; and $R_6$ represents H, alkyl or acyl.

In certain embodiments, the compounds of the present invention are represented by structure 5 and the attendant definitions, wherein $R_1$ represents independently for each occurrence OR, halogen, or $CF_3$; the geminal instances of $R_2$ and $R_3$ taken together represent O; and $R_6$ represents H, alkyl or acyl.

In certain embodiments, the compounds of the present invention are represented by structure 5 and the attendant definitions, wherein $R_1$ represents independently for each occurrence OR, halogen, or $CF_3$; $R_2$ and $R_3$ represent independently for each occurrence H, OR, or $N(R)_2$; $R_6$ represents H, alkyl or acyl; and $R_7$ represents H, alkyl or aralkyl.

In certain embodiments, the compounds of the present invention are represented by structure 5 and the attendant definitions, wherein $R_1$ represents independently for each occurrence OR, halogen, or $CF_3$; the geminal instances of $R_2$ and $R_3$ taken together represent O; $R_6$ represents H, alkyl or acyl; and $R_7$ represents H, alkyl or aralkyl.

In certain assays based on mammalian G-protein-coupled receptors or sigma receptors, certain compounds according to general structure 5 have $IC_{50}$ values less than 10 $\mu$M, more preferably less than 1 $\mu$M, and most preferably less than 0.1 $\mu$M.

In certain embodiments, the present invention relates to ligands for G-protein-coupled or sigma receptors, wherein the ligands are represented by any of generalized structures outlined above, and any of the sets of definitions associated with one of those structures. Preferably, the ligands of the present invention are antagonists or agonists of G-protein-coupled or sigma receptors. In any event, the ligands of the present invention preferably exert their effect on the receptors at a concentration less than about 10 micromolar, more preferably at a concentration less than about 1 micromolar, and most preferably at a concentration less than 100 nanomolar. In certain embodiments, the ligands of the present invention bind selectively to a single family of G-protein-coupled or sigma receptors. In other embodiments, the ligands of the present invention bind selectively to a subtype of receptor within a family of G-protein-coupled or sigma receptors.

In certain embodiments, the selectivity of a ligand for a specific family or subtype of receptor renders that ligand an effective therapeutic agent for an acute or chronic ailment, disease or malady. In certain embodiments, the selectivity of a ligand for a specific family or subtype of receptor consists of a binding affinity for that family or subtype of receptor at least a factor of ten greater than its binding affinity for other families or subtypes of G-protein-coupled or sigma receptors. In preferred embodiments, the selectivity of a ligand for a specific family or subtype of receptor consists of a binding affinity for that family or subtype of receptor at least a factor of one hundred greater than its binding affinity for other families or subtypes of G-protein-coupled or sigma receptors. In certain embodiments, the selectivity of a ligand for a specific family or subtype of receptor consists of a binding affinity for that family or subtype of receptor at least a factor of one thousand greater than its binding affinity for other families or subtypes of G-protein-coupled or sigma receptors.

The present invention contemplates pharmaceutical formulations (see below) of the ligands of the present invention. In certain embodiments, the pharmaceutical formulations will comprise ligands of the present invention that effect only a specific family or subtype of G-protein-coupled or sigma receptor, and thereby have a therapeutic effect on an acute or chronic ailment, disease or malady that is at least in part due to biochemical or physiological processes associated with the receptor(s). In preferred embodiments, the pharmaceutical formulations will comprise ligands of the present invention that effect only a subtype of receptor, and thereby have a therapeutic effect on an acute or chronic ailment, disease or malady that is at least in part due to biochemical or physiological processes associated with the specific subtype of receptor. The Background of the Invention (see above) teaches examples of acute or chronic ailments, diseases or maladies that are caused or exacerbated by biochemical or physiological processes associated with specific G-protein-coupled or sigma receptors. One of ordinary skill in the art will be able to accumulate, by reference to the scientific literature, a more comprehensive list of acute or chronic ailments, diseases or maladies that are caused or exacerbated by biochemical or physiological processes associated with specific G-protein-coupled or sigma receptors. The present invention contemplates pharmaceutical formulations of ligands of the present invention that will be of medicinal value against the aforementioned acute or chronic ailments, diseases or maladies.

Biochemical Activity at Cellular Receptors, and Assays to Detect it

Assaying processes are well known in the art in which a reagent is added to a sample, and measurements of the sample and reagent are made to identify sample attributes stimulated by the reagent. For example, one such assay process concerns determining in a chromogenic assay the amount of an enzyme present in a biological sample or solution. Such assays are based on the development of a colored product in the reaction solution. The reaction develops as the enzyme catalyzes the conversion of a colorless chromogenic substrate to a colored product.

Assays useful in the present invention concern determining the activity of receptors the activation of which initiates subsequent intracellular events in which intracellular stores of calcium ions are released for use as a second messenger. Activation of some G-protein-coupled receptors stimulates the formation of inositol triphosphate (IP3, a G-protein-coupled receptor second messenger) through phospholipase C-mediated hydrolysis of phosphatidylinositol, Berridge and Irvine (1984). Nature 312:315–21. IP3 in turn stimulates the release of intracellular calcium ion stores.

A change in cytoplasmic calcium ion levels caused by release of calcium ions from intracellular stores is used to determine G-protein-coupled receptor function. This is another type of indirect assay. Among G-protein-coupled receptors are muscarinic acetylcholine receptors (mAChR), adrenergic receptors, serotonin receptors, dopamine receptors, angiotensin receptors, adenosine receptors, bradykinin receptors, metabotropic excitatory amino acid receptors and the like. Cells expressing such G-protein-coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores. Another type of indirect assay involves determining the activity of receptors which, when activated, result in a change in the level of intracellular cyclic nucleotides, e.g., cAMP, cGMP. For example, activation of some dopamine, serotonin, metabotropic glutamate receptors and muscarinic acetylcholine receptors results in a decrease in the cAMP or cGMP levels of the cytoplasm.

Furthermore, there are cyclic nucleotide-gated ion channels, e.g., rod photoreceptor cell channels and olfactory neuron channels [see, Altenhofen, W. et al. (1991) Proc. Natl. Acad. Sci U.S.A. 88:9868–9872 and Dhallan et al. (1990) Nature 347:184–187] that are permeable to cations upon activation by binding of cAMP or cGMP. A change in cytoplasmic ion levels caused by a change in the amount of cyclic nucleotide activation of photo-receptor or olfactory neuron channels is used to determine function of receptors that cause a change in cAMP or cGMP levels when activated. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cell for this type of assay can be made by co-transfection of a host cell with DNA encoding a cyclic nucleotide-gated ion channel and a DNA encoding a receptor (e.g., certain metabotropic glutamate receptors, muscarinic acetylcholine receptors, dopamine receptors, serotonin receptors and the like, which, when activated, causes a change in cyclic nucleotide levels in the cytoplasm.

Any cell expressing a receptor protein which is capable, upon activation, of directly increasing the intracellular concentration of calcium, such as by opening gated calcium channels, or indirectly affecting the concentration of intracellular calcium as by causing initiation of a reaction which utilizes Ca<2+> as a second messenger (e.g., G-protein-coupled receptors), may form the basis of an assay. Cells endogenously expressing such receptors or ion channels and cells which may be transfected with a suitable vector encoding one or more such cell surface proteins are known to those of skill in the art or may be identified by those of skill in the art. Although essentially any cell which expresses endogenous ion channel and/or receptor activity may be used, it is preferred to use cells transformed or transfected with heterologous DNAs encoding such ion channels and/or receptors so as to express predominantly a single type of ion channel or receptor. Many cells that may be genetically engineered to express a heterologous cell surface protein are known. Such cells include, but are not limited to, baby hamster kidney (BHK) cells (ATCC No. CCL10), mouse L cells (ATCC No. CCLI.3), DG44 cells [see, Chasin (1986) Cell. Molec. Genet. 12:555] human embryonic kidney (HEK) cells (ATCC No. CRL1573), Chinese hamster ovary (CHO) cells (ATCC Nos. CRL9618, CCL61, CRL9096), PC12 cells (ATCC No. CRL1721) and COS-7 cells (ATCC No. CRL1651). Preferred cells for heterologous cell surface protein expression are those that can be readily and efficiently transfected. Preferred cells include HEK 293 cells, such as those described in U.S. Pat. No. 5,024,939.

Any compound which is known to activate ion channels or receptors of interest may be used to initiate an assay. Choosing an appropriate ion channel- or receptor-activating reagent depending on the ion channel or receptor of interest is within the skill of the art. Direct depolarization of the cell membrane to determine calcium channel activity may be accomplished by adding a potassium salt solution having a concentration of potassium ions such that the final concentration of potassium ions in the cell-containing well is in the range of about 50–150 mM (e.g., 50 mM KCl). With respect to ligand-gated receptors and ligand-gated ion channels, ligands are known which have affinity for and activate such receptors. For example, nicotinic acetyloholine receptors are known to be activated by nicotine or acetylcholine; similarly, muscarinic acetylcholine receptors may be activated by addition of muscarine or carbamylcholine.

Agonist assays may be carried out on cells known to possess ion channels and/or receptors to determine what effect, if any, a compound has on activation or potentiation of ion channels or receptors of interest. Agonist assays also may be carried out using a reagent known to possess ion channel- or receptor-activating capacity to determine whether a cell expresses the respective functional ion channel or receptor of interest.

Contacting a functional receptor or ion channel with agonist typically activates a transient reaction; and prolonged exposure to an agonist may desensitize the receptor or ion channel to subsequent activation. Thus, in general, assays for determining ion channel or receptor function should be initiated by addition of agonist (i.e., in a reagent solution used to initiate the reaction). The potency of a compound having agonist activity is determined by the detected change in some observable in the cells (typically an increase, although activation of certain receptors causes a decrease) as compared to the level of the observable in either the same cell, or substantially identical cell, which is treated substantially identically except that reagent lacking the agonist (i.e., control) is added to the well. Where an agonist assay is performed to test whether or not a cell expresses the functional receptor or ion channel of interest, known agonist is added to test-cell-containing wells and to wells containing control cells (substantially identical cell that lacks the specific receptors or ion channels) and the levels of observable are compared. Depending on the assay, cells lacking the ion channel and/or receptor of interest should exhibit substantially no increase in observable in response to the known agonist. A substantially identical cell may be derived from the same cells from which recombinant cells are prepared but which have not been modified by introduction of heterologous DNA. Alternatively, it may be a cell in which the specific receptors or ion channels are removed. Any statistically or otherwise significant difference in the level of observable indicates that the test compound has in some manner altered the activity of the specific receptor or ion channel or that the test cell possesses the specific functional receptor or ion channel.

In an example of drug screening assays for identifying compounds which have the ability to modulate ion channels or receptors of interest, individual wells (or duplicate wells, etc.) contain a distinct cell type, or distinct recombinant cell line expressing a homogeneous population of a receptor or ion channel of interest, so that the compound having unidentified activity may be screened to determine whether it possesses modulatory activity with respect to one or more of a variety of functional ion channels or receptors. It is also contemplated that each of the individual wells may contain the same cell type so that multiple compounds (obtained from different reagent sources in the apparatus or contained within different wells) can be screened and compared for modulating activity with respect to one particular receptor or ion channel type.

Antagonist assays, including drug screening assays, may be carried out by incubating cells having functional ion channels and/or receptors in the presence and absence of one or more compounds, added to the solution bathing the cells in the respective wells of the microtiter plate for an amount of time sufficient (to the extent that the compound has affinity for the ion channel and/or receptor of interest) for the compound(s) to bind to the receptors and/or ion channels, then activating the ion channels or receptors by addition of known agonist, and measuring the level of observable in the cells as compared to the level of observable in either the same cell, or substantially identical cell, in the absence of the putative antagonist.

The assays are thus useful for rapidly screening compounds to identify those that modulate any receptor or ion channel in a cell. In particular, assays can be used to test functional ligand-receptor or ligand-ion channel interactions for cell receptors including ligand-gated ion channels, voltage-gated ion channels, G-protein-coupled receptors and growth factor receptors.

Those of ordinary skill in the art will recognize that assays may encompass measuring a detectable change of a solution as a consequence of a cellular event which allows a compound, capable of differential characteristics, to change its characteristics in response to the cellular event. By selecting a particular compound which is capable of differential characteristics upon the occurrence of a cellular event, various assays may be performed. For example, assays for determining the capacity of a compound to induce cell injury or cell death may be carried out by loading the cells with a pH-sensitive fluorescent indicator such as BCECF Molecular Probes, Inc., Eugene, Oreg. 97402, Catalog #B1150) and measuring cell injury or cell death as a function of changing fluorescence over time.

Sigma receptor binding assays using guinea pig brain membrane homogenates and the radioligand [<3>H]DTG may be conducted as described by Weber et al., Proc. Natl. Acad. Sci. USA 83:8784–8788 (1986). Furthermore, assays for binding to sigma receptors which rely on a guinea pig brain (less the cerebellum) homogenate may be used, in a modification of the process of L. Radesca et al., J. Med. Chem., 34, 3058–3065 (1991). In this system, [$^3$H]-(+)-3-PPP is used as radioligand and haloperidol is used for measuring the non-specific binding. The inhibition constants ($K_i$, nM) may be calculated by non-linear regression analysis by using the EBDA/LIGAND program (Munson and Rodbard, Analytical Biochemistry, 107, 220 (1980)).

In a further example of useful assays, the function of receptors whose activation results in a change in the cyclic nucleotide levels of the cytoplasm may be directly determined in assays of cells that express such receptors and that have been injected with a fluorescent compound that changes fluorescence upon binding cAMP. The fluorescent compound comprises cAMP-dependent-protein kinase in which the catalytic and regulatory subunits are each labelled with a different fluorescent-dye [Adams et al. (1991) Nature 349:694–697]. When cAMP binds to the regulatory subunits, the fluorescence emission spectrum changes; this change can be used as an indication of a change in cAMP concentration.

The function of certain neurotransmitter transporters which are present at the synaptic cleft at the junction between two neurons may be determined by the development of fluorescence in the cytoplasm of such neurons when conjugates of an amine acid and fluorescent indicator (wherein the fluorescent indicator of the conjugate is an acetoxymethyl ester derivative e.g., 5-(aminoacetamido) fluorescein; Molecular Probes, Catalog #A1363) are transported by the neurotransmitter transporter into the cytoplasm of the cell where the ester group is cleaved by esterase activity and the conjugate becomes fluorescent.

In practicing an assay of this type, a reporter gene construct is inserted into an eukaryotic cell to produce a recombinant cell which has present on its surface a cell surface protein of a specific type. The cell surface receptor may be endogenously expressed or it may be expressed from a heterologous gene that has been introduced into the cell. Methods for introducing heterologous DNA into eukaryotic cells are-well known in the art and any such method may be used. In addition, DNA encoding various cell surface proteins is known to those of skill in the art or it may be cloned by any method known to those of skill in the art.

The recombinant cell is contacted with a test compound and the level of reporter gene expression is measured. The contacting may be effected in any vehicle and the testing may be by any means using any protocols, such as serial dilution, for assessing specific molecular interactions known to those of skill in the art. After contacting the recombinant cell for a sufficient time to effect any interactions, the level of gene expression is measured. The amount of time to effect such interactions may be empirically determined, such as by running a time course and measuring the level of transcription as a function of time. The amount of transcription may be measured using any method known to those of skill in the art to be suitable. For example, specific mRNA expression may be detected using Northern blots or specific protein product may be identified by a characteristic stain. The amount of transcription is then compared to the amount of transcription in either the same cell in the absence of the test compound or it may be compared with the amount of transcription in a substantially identical cell that lacks the specific receptors. A substantially identical cell may be derived from the same cells from which the recombinant cell was prepared but which had not been modified by introduction of heterologous DNA. Alternatively, it may be a cell in which the specific receptors are removed. Any statistically or otherwise significant difference in the amount of transcription indicates that the test compound has in some manner altered the activity of the specific receptor.

If the test compound does not appear to enhance, activate or induce the activity of the cell surface protein, the assay may be repeated and modified by the introduction of a step in which the recombinant cell is first tested for the ability of a known agonist or activator of the specific receptor to activate transcription if the transcription is induced, the test compound is then assayed for its ability to inhibit, block or otherwise affect the activity of the agonist.

The transcription based assay is useful for identifying compounds that interact with any cell surface protein whose activity ultimately alters gene expression. In particular, the assays can be used to test functional ligand-receptor or ligand-ion channel interactions for a number of categories of cell surface-localized receptors, including: ligand-gated ion channels and voltage-gated ion channels, and G protein-coupled receptors.

Any transfectable cell that can express the desired cell surface protein in a manner such the protein functions to intracellularly transduce an extracellular signal may be used. The cells may be selected such that they endogenously express the cell surface protein or may be genetically engineered to do so. Many such cells are known to those of skill in the art. Such cells include, but are not limited to Ltk<–> cells, PC12 cells and COS-7 cells.

The preparation of cells which express a receptor or ion channel and a reporter gene expression construct, and which are useful for testing compounds to assess their activities, is exemplified in the Examples provided herewith by reference to mammalian Ltk<–> and COS-7 cell lines, which express the Type I human muscarinic (HM1) receptor and which are transformed with either a c-fos promoter-CAT reporter gene expression construct or a c-fos promoter-luciferase reporter gene expression construct.

Any cell surface protein that is known to those of skill in the art or that may be identified by those of skill in the art may used in the assay. The cell surface protein may endogenously expressed on the selected cell or it may be expressed from cloned DNA. Exemplary cell surface proteins include, but are not limited to, cell surface receptors and ion channels. Cell surface receptors include, but are not limited to, muscarinic receptors (e.g., human M2 (GenBank accession #M16404); rat M3 (GenBank accession #M16407); human M4 (GenBank accession #M16405); human M5 (Bonner et al. (1988) Neuron 1:403–410); and the like); neuronal nicotinic acetylcholine receptors (e.g., the alpha 2, alpha 3 and beta 2 subtypes disclosed in U.S. Ser. No. 504,455 (filed Apr. 3, 1990), hereby expressly incorporated by reference herein in its entirety); the rat alpha 2 subunit (Wada et al. (1988) Science 240:330–334); the rat alpha 3 subunit (Boulter et al. (1986) Nature 319:368–374); the rat alpha 4 subunit (Goldman et al. (1987) cell 48:965–973); the rat alpha 5 subunit (Boulter et al. (1990) J. Biol. Chem. 265:4472–4482); the rat beta 2 subunit (Deneris et al. (1988) Neuron 1:45–54); the rat beta 3 subunit (Deneris et al. (1989) J. Biol. Chem. 264: 6268–6272); the rat beta 4 subunit (Duvoisin et al. (1989) Neuron 3:487–496); combinations of the rat alpha subunits, beta subunits and alpha and beta subunits; GABA receptors (e.g., the bovine alpha 1 and beta 1 subunits (Schofield et al. (1987) Nature 328:221–227); the bovine alpha 2 and alpha 3 subunits (Levitan et al. (1988) Nature 335:76–79); the gamma-subunit (Pritchett et al. (1989) Nature 338:582–585); the beta 2 and beta 3 subunits (Ymer et alo (1989) EMBO J. 8:1665–1670); the delta subunit (Shivers, B. D. (1989) Neuron 3:327–337); and the like); glutamate receptors (e.g., receptor isolated from rat brain (Hollmann et al. (1989) Nature 342:643–648); and the like); adrenergic receptors (e.g., human beta 1 (Frielle et al. (1987) Proc. Natl. Acad. Sci. 84:7920–7924); human alpha 2 (Kobilka et al. (1987) Science 238:650–656); hamster beta 2 (Dixon et al. (1986) Nature 321:75–79); and the like); dopamine receptors (e.g., human D2 (Stormann et al. (1990) Molec. Pharm. 37:1–6); rat (Bunzow et al. (1988) Nature 336:783–787); and the like); NGF receptors (e.g., human NGF receptors (Johnson et al. (1986) Cell 47:545–554); and the like); serotonin receptors (e.g., human 5HT1a (Kobilka et al. (1987) Nature 329:75–79); rat 5HT2 (Julius et al. (1990) PNAS 87:928–932); rat 5HT1c (Julius et al. (1988) Science 241:558–564); and the like).

Reporter gene constructs are prepared by operatively linking a reporter gene with at least one transcriptional regulatory element. If only one transcriptional regulatory element is included it must be a regulatable promoter, At least one of the selected transcriptional regulatory elements must be indirectly or directly regulated by the activity of the selected cell-surface receptor whereby activity of the receptor can be monitored via transcription of the reporter genes.

The construct may contain additional transcriptional regulatory elements, such as a FIRE sequence, or other sequence, that is not necessarily regulated by the cell surface protein, but is selected for its ability to reduce background level transcription or to amplify the transduced signal and to thereby increase the sensitivity and reliability of the assay.

Many reporter genes and transcriptional regulatory elements are known to those of skill in the art and others may be identified or synthesized by methods known to those of skill in the art.

A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties.

Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101).

Transcriptional control elements include, but are not limited to, promoters, enhancers, and repressor and activator binding sites, Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al. (1990) Neuron 4: 477–485), such as c-fos, Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts", refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1–19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar—agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intravectally, for example, as a pessary, cream or foam.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., San Francisco, U.S.A., 1969 or "Livestock Feeds and Feeding" 0 and B books, Corvallis, Oreg., U.S.A., 1977).

Combinatorial Libraries

The subject reactions readily lend themselves to the creation of combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A. Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811–5814; Valerio et al. (1991) *Anal Biochem* 197:168–177; Bray et al. (1991) *Tetrahedron Lett* 32:6163–6166).

C) Divide-Couple-Recombine

In yet another embodiment, a variegated library of compounds can be provided on a set of beads utilizing the strategy of divide-couple-recombine (see, e.g., Houghten (1985) *PNAS* 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271–280; Fodor, S. P. A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-Oligomers

The principle of using oligonucleotides to encode combinatorial synthetic libraries was described in 1992 (Brenner et al. (1992) *PNAS* 89:5381–5383), and an example of such a library appeared the following year (Needles et al. (1993) *PNAS* 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529–2531), orthogonality in synthesis is achieved by employing acid-labile protection for the coding strand and base-labile protection for the compound strand.

In an alternative approach (Nikolaiev et al. (1993) *Pept Res* 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-Sequenceable Tagging: Binary Encoding

An alternative form of encoding the test compound library employs a set of non-sequencable electrophoric tagging molecules that are used as a binary code (Ohlmeyer et al. (1993) *PNAS* 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXEMPLIFICATION

The invention now being generally described, it will be more readily understood by reference to the following examples, which are included merely for purposes of illustration of certain aspects and embodiments of the present invention, and are not intended to limit the invention.

Example 1

Synthesis of 3,4-Dihydrospiro[5H-1-benzazepine-2(1H),4'-piperidin]-5-one (11)

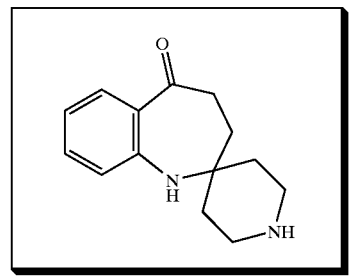

11

1. Synthesis of 1-tert-Butoxycarbonyl-4-allyl-4-(2-bromophenylamino)piperidine (4).

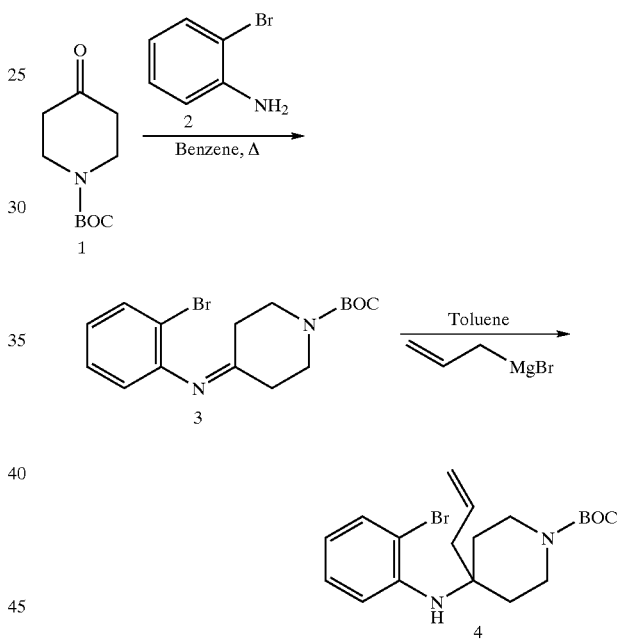

A solution of N-tert-butoxycarbonyl-4-piperidone (1) (18.2 g, 91.4 mmol) and 2-bromoaniline (2) (16.4 g, 95.4 mmol) in anhydrous benzene (24 mL) was heated at reflux, with the azeotropic removal of water. After 3 days, the reaction was allowed to cool to room temperature, and concentrated to obtain 3 as an orange oil.

To a solution of 3 in anhydrous toluene (200 mL) was added dropwise a solution of allylmagnesium bromide (91 mL, 1 M in diethyl ether, 1 equiv.). After the addition was completed, the reaction was stirred at room temperature for 19 h and was then quenched with sat. aqueous $NH_4Cl$ (100 mL). The aqueous layer was extracted with ether (3×200 mL). The combined organic layers were washed with sat. aqueous NaCl and concentrated to yield a crude oil. Silica gel chromatography (95:5 hexanes:EtOAc) afforded 4 as a yellow oil (14.11 g, 35.5 mmol, 38%). TLC: $R_f$ (hexanes)= 1.9. LRMS: M+=337.

2. Synthesis of 1-Acetyl-4-allyl-4-(2-bromophenylamino) piperidine (5).

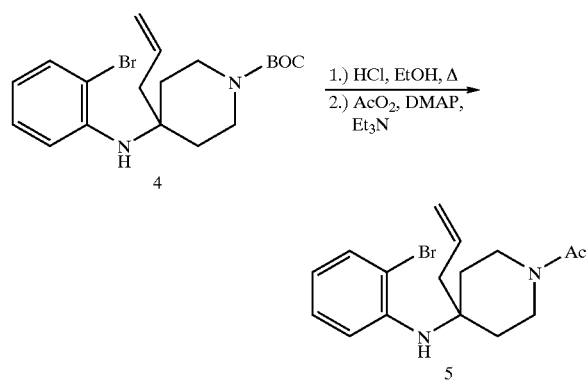

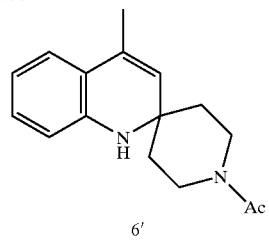

To a solution of 4 (14.11 g, 35.5 mmol) in absolute ethanol (27 mL) was added a 2.5 N ethanolic HCl solution (18 mL). The reaction was heated at reflux. After 20 h, the reaction was allowed to cool to room temperature and the solvent was evaporated to yield a crude yellow oil. The crude material was taken up in CH$_2$Cl$_2$, neutralized to pH ~10 with 1 N NaOH, followed by extraction of the aqueous layer with CH$_2$Cl$_2$ (3×100 mL). The combined organic layer was dried over Na$_2$SO$_4$ and concentrated to afford the crude diamine as a brown oil (10.46 g, 31.1 mmol, 88%)

A solution of the diamine (10.46 g, 40 mmol) in CH$_2$Cl$_2$ (53 mL) containing DMAP (3.24 g, 26.6 mmol), Ac$_2$O (3.7 mL, 39.1 mmol) and Et$_3$N (5.4 mL, 38.7 mmol) was stirred at room temperature for 20 h. After removal of the solvent, the remaining solid was purified by silica gel chromatography (75:15:10 EtOAc:hexanes:MeOH) to yield 5 as a yellow oil (8.61 g, 30 mmol, 72%). TLC: R$_f$ (80:20 EtOAc:hexanes) 0.33. $^1$H NMR (CDCl$_3$) δ 7.44 (1H, dd, J=1.6, 7.8 Hz), 7.16 (1H, m), 7.01 (1H, dd, J=1.8, 7.7 Hz), 6.60 (1H, ddd, J=1.8, 4.7, 4.9 Hz), 5.74 (1H, m), 5.08 (2H, m), 4.19 (1H, m), 3.70 (1H, m), 3.42 (1H, m), 3.17 (1H, m), 2.67 (2H, m), 2.19–2.05 (5H, m), 1.76–1.56 (2H, m).

3. Synthesis of 1-Acetyl-4'methylidene-3',4'-dihydrospiro[piperidine-4,2'(1'H)-quinoline] (6) and 1-acetyl-4'-methylspiro[piperidine-4,2'(1'H)-quinoline (6').

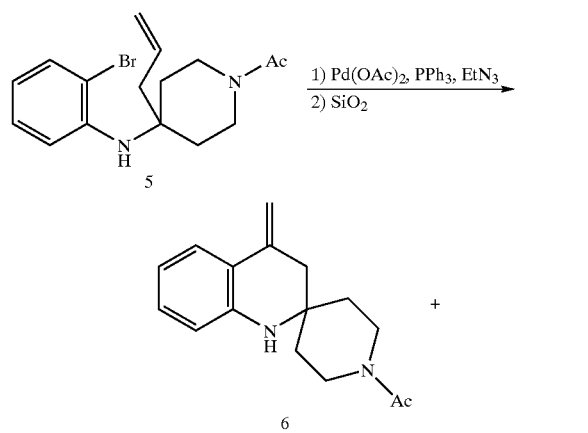

To a solution of 5 (8.61 g, 30 mmol) in anhydrous acetonitrile (196 mL) was added triphenylphosphine (1.47 g, 5.6 mmol), triethylamine (7.83 mL, 56 mmol), and palladium acetate (0.63 g, 2.8 mmol). The reaction mixture was heated at 80° C. for 72 h. After cooling to room temperature, the catalyst was filtered off and the filtrate was concentrated to yield a crude dark orange residue, which was purified by flash chromatography (silica gel, 75:15:10 EtOAc, hexanes:MeOH) to yield a mixture of 6 and 6'(7.14 g, 0.3 mmol, 71%) in a 1:9 ratio. 6: $^1$H NMR (CDCl$_3$) δ 7.12 (1H, m), 7.05 (1H, dd, J=1.4, 7.5 Hz), 6.71 (1H, ddd, J=1.1, 7.4, 8.3 Hz), 6.58 (1H, ddd, J=1.0, 8.1, 9.1 Hz), 5.45 (1H, s), 4.33 (1H, s), 3.80–3.45 (4H, m), 2.11 (3H, s), 2.05 (3H, s) 1.76–1.40 (4H, m). 6': $^1$H NMR (CDCl$_3$) δ 7.67–7.45 (4H, m), 5.45 (1H, s), 4.85 (1H, s), 4.33 (1H, s), 3.80–3.45 (4H, m), 2.49 (2H, s), 2.09 (3H, s) 1.76–1.40 (4H, m).

4. Synthesis of 1,1'Diacetyl-4'methylspiro[piperidine-4,2'(1'H)-quinoline] (7).

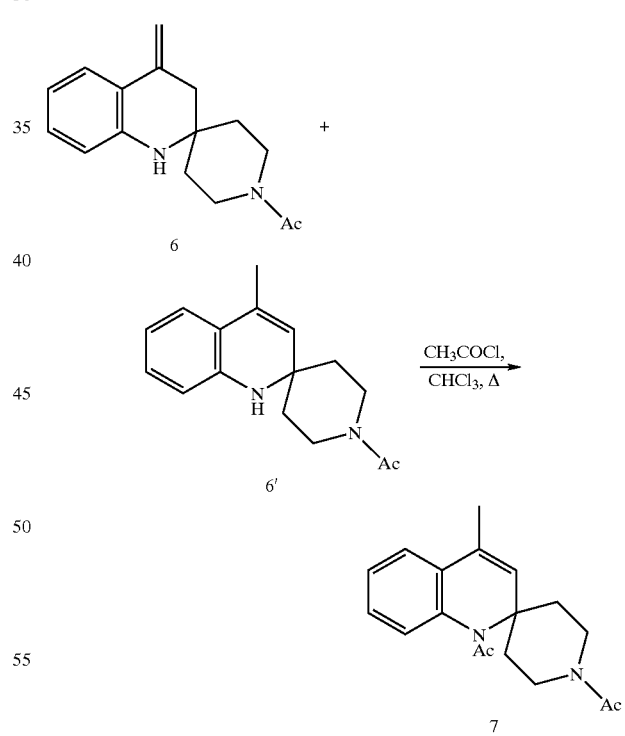

To a solution of 6 and 6' (7.68 g, 30 mmol) in anhydrous CHCl$_3$ (77 mL) was added dropwise acetyl chloride (17.28 mL, 243 mmol) and the reaction was heated at 70° C. for 72 h. After cooling to room temperature, the reaction was quenched with H$_2$O (200 mL). The aqueous layer was extracted with EtOAc (3×100 mL). The combined organic layers were dried over Na$_2$SO$_4$ and concentrated to afford an oil, which was purified by flash chromatography on silica gel (75:15:10 EtOAc:hexanes:MeOH) to give 7 (7.29 g, 20 mmol, 81%). ¹H NMR (CDCl₃) δ 7.30–7.12 (4H, m), 5.84 (1H, s), 3.95–3.88 (1H, m), 3.63–3.29 (3H, m), 2.81 (1H, s), 2.25–2.04 (4H, m), 2.03 (3H, s), 1.95 (3H, s), 1.67–1.32 (2H, m); LRMS: M+=298.

5. Synthesis of N-(1-Acetyl-4-formylpiperidin-4-yl)-N-(2-acetylphenyl)-acetamide (8).

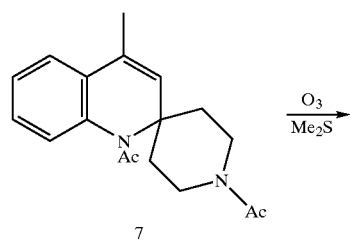

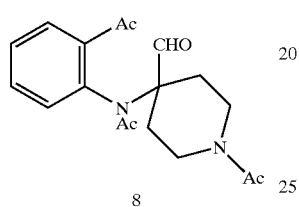

A solution of 7 (7.29 g, 20 mmol) in absolute ethanol (177 mL) was treated with ozone at −78° C. After 2 h, Me₂S (59 mL, 70 mmol) was added. The reaction mixture was warmed to RT, and then concentrated. The resulting crude oil was purified by flash column chromatography on silica gel (75:15:10 EtOAc:hexanes:MeOH) to give 8 (7.84 g, 20 mmol, 71%) as an oil. ¹H NMR (CDCl₃) δ 9.60 (1H, m), 7.90 (1H, m), 7.75–7.50 (2H, m), 7.34–7.27 (1H, m), 4.30 (1H, m), 3.89–3.54 (2H, m), 3.30–3.15 (1H, m), 2.85–2.39 (4H, m), 2.05–1.47 (3H, m), 1.26 (3H, s) 1.24–1.07 (1H, m).

6. Synthesis of 1'-Acetylspiro[5-1-benzazepine-2(1H), 4'-piperidin]-5-one (9).

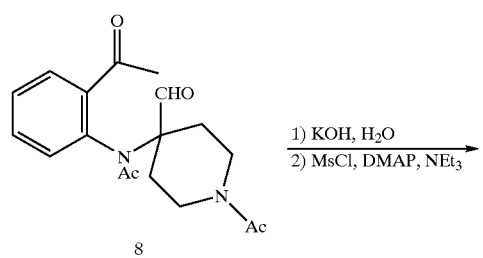

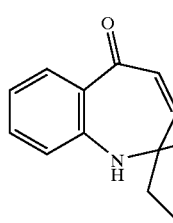

A solution of 8 (7.84 g, 23.8 mmol) in THF (8 mL) was added to KOH (2.66 g, 47.5 mmol) in water (7.8 mL) at 0° C. After 1 h, the reaction was diluted with CH₂Cl₂ (10 mL) and the aqueous layer was extracted with CH₂Cl₂ (3×50 mL). The combined organic layers were dried over Na₂SO₄ and concentrated to yield a crude oil. The crude material was purified by silica gel chromatography (75:15:10 EtOAc:hexanesMeOH) to yield 9 (2.99 g, 11 mmol, 69%) as a yellow solid. ¹H NMR (CDCl₃) δ 8.07 (1H, dd, J=1.6, 7.2 Hz), 7.35 (1H, m), 6.95 (1H, m), 6.79 (1H, d, J=7.8 Hz), 6.37 (2H, m), 3.33 (1H, s), 3.80–3.61 (2H, m), 3.45–3.11 (2H, m), 2.09 (3H, s) 1.97–1.64 (4H, m); LRMS: M+=270.

7. Synthesis of 1'-Acetyl-3,4-dihydrospiro[5H-1-benzazepine-2(1H), 4'-piperidin]-5-one (10)

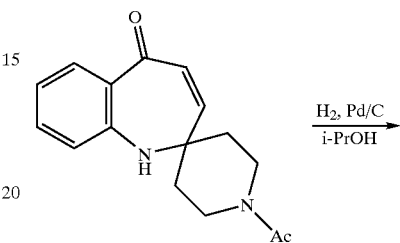

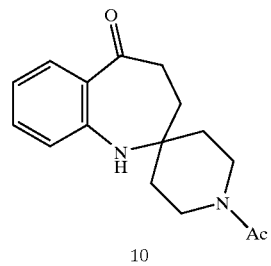

A slurry of the α,β-unsaturated ketone 9 (150 mg, 0.56 mmol) in i-PrOH was hydrogenated over palladium on charchoal (5%, 15 mg) at 1 atm. After completion of the reaction the catalyst was filtered off and the filtrate was concentrated to yield 10 (140 mg, 0.51 mmol, 93%) as a light yellow oil. ¹H NMR (CDCl₃) δ 7.87 (1H, dd, J=1.6, 7.9 Hz), 7.34 (1H, m), 6.97 (1H, m), 6.79 (1H, d, J=8.0 Hz), 3.9 (1H, s), 3.63 (2H, t, J=5.5 Hz), 3.43 (2H, m), 2.86 (2H, m), 2.08 (3H, s), 1.99 (2H, m), 1.69 (4H, m); lit. ¹H NMR (CDCl₃) δ 7.72 (1H, d, J=8.1 Hz), 7.21 (1H, dd, J=7.7, 7.7 Hz), 6.84 (1H, dd, J=7.7, 7.7 Hz), 6.78 (1H, d, J=7.7 Hz), 4.28 (1H, s), 3.63–3.21 (4H, m), 2.82–2.60 (2H, m), 1.98 (3H, s), 1.95–1.8 (2H, m), 1.69–1.50 (4H, m); LRMS: M+=272.

8. Synthesis of 3,4-Dihydrospiro[5H-1-benzazepine-2(1H), 4'-piperidin]-5-one (11)

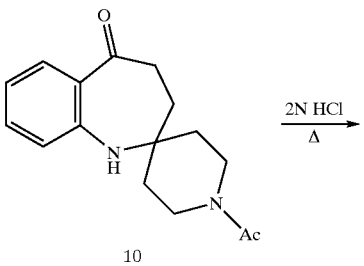

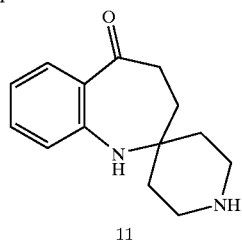

11

Acetate 10 (20 mg, 0.072 mmoles) was dissolved in 2 N HCl (0.31 mL) and heated to 85° C. After 3 h, the reaction mixture was diluted with 5 N NaOH to a pH~11 and extracted with CH$_2$Cl$_2$ (3×3 mL). The combined organic layers were dried over Na$_2$SO$_4$ and concentrated to afford 11(16.2 mg, 0.071 mmoles, 96%) as a colorless oil. $^1$H NMR (CDCl$_3$) δ 7.83 (1H, dd, J=1.7, 7.6 Hz), 7.32 (1H, ddd, J=2.2, 8.1, 9.1 Hz), 6.93 (1H, m), 6.77 (1H, d, J=7.9 Hz), 3.76 (1H, d, J=7.9 Hz), 3.98 (1H, s), 2.83 (6H, m), 1.31 (2H, m), 1.64 (5H, m); IR (thin film, NaCl) 3290, 2964, 1716, 1664, 1422 cm$^{-1}$; LRMS: M+=230.

Example 2
Synthesis of 1'-(3,4-Dichlorobenzoyl)-3,4-dihydrospiro[5H-1-benzazepine-2(1H)-4'-piperidin]-5-one (12)

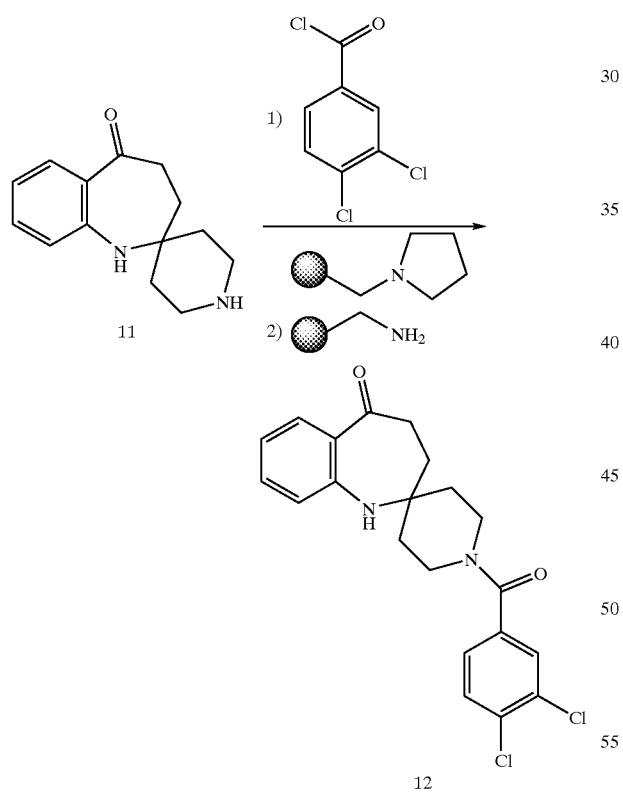

12

To a solution of diamine 11 (20 mg, 0.087 mmol) in anhydrous CH$_2$Cl$_2$ (0.5 mL) was added 3,4-dichlorobenzoyl chloride (22 mg, 0.104 mmol) and piperidinomethyl polystyrene (3.5 mmol/g resin, 25 mg). The reaction mixture was agitated at room temperature for 4 h, and the reaction mixture was then filtered. To the filtrate was added AM resin (3.21 mmol/g resin, 32 mg) and the reaction mixture was agitated for 8 h. The reaction was filtered, and the filtrate was concentrated to yield 12 (15.8 mg, 0.039 mmol, 45%) as a yellow oil. $^1$H NMR (CDCl$_3$) δ 7.85 (1H, m), 7.50 (1H, m), 7.35 (2H, m), 7.23 (1H, m), 7.01 (1H, m), 6.80 (1H, m), 3.91 (1H, s), 2.85 (6H, m), 2.02 (2H, m), 1.74 (4H, m); LRMS: M+=403.

Example 3
Synthesis of 1'-(4-morpholine Carbonyl)-3,4-dihydrospiro[5H-1-benzazepine-2(1H)-4'-piperidin]-5-one (13)

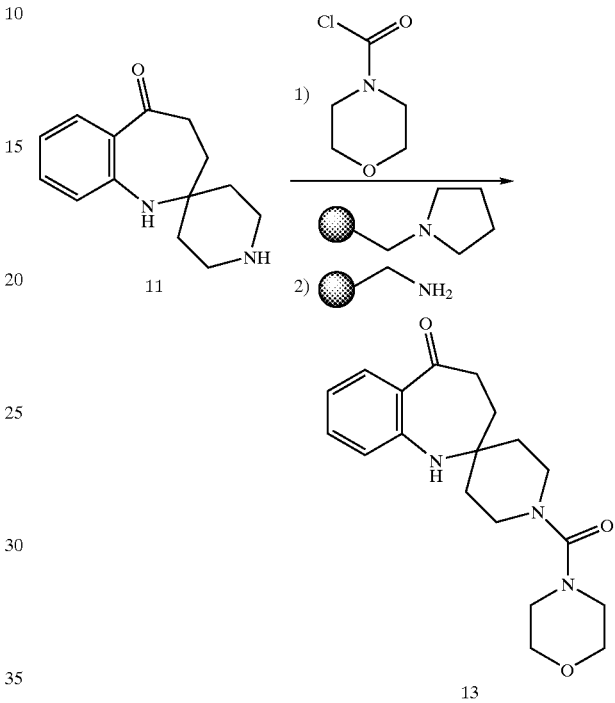

13

To a solution of diamine 11 (10 mg, 0.043 mmol) in anhydrous CH$_2$Cl$_2$ (0.5 mL) was added 4-morpholine carbonyl chloride (8.1 mg, 0.052 mmol) and piperidinomethyl polystyrene (3.5 mmol/g resin, 13 mg). The reaction mixture was agitated at room temperature for 4 h, and the reaction mixture was then filtered. To the filtrate was added AM resin (3.21 mmol/g resin, 16 mg) and the reaction mixture was agitated for 8 h at room temperature. The reaction was filtered and the filtrate was concentrated to yield 13 (13 mg, 0.038 mmol, 88%) as an oil. LRMS: M+=343.

Example 4
Synthesis of 1'-(4-tert-Butylbenzoyl)-3,4-dihydrospiro[5H-1-benzazepine-2(1H)-4'-piperidin]-5-one (14)

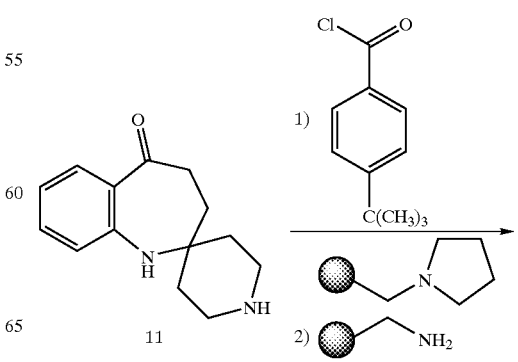

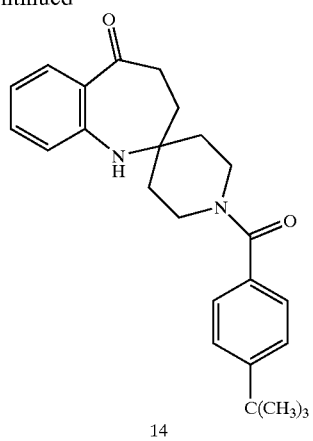

14

To a solution of diamine 11 (10 mg, 0.043 mmol) in anhydrous CH₂Cl₂ (0.5 mL) was added 4-tert-butylbenzoyl chloride (10 mg, 0.052 mmol) and piperidinomethyl polystyrene (3.5 mmol/g resin, 13 mg). The reaction was agitated at RT for 4 h, and the reaction mixture was then filtered. To the filtrate was added AM resin (3.21 mmol/g resin, 16 mg) and the reaction mixture was agitated for 8 h at room temperature. The reaction was filtered and the filtrate was concentrated to yield 14 (12 mg, 0.031 mmol, 72%) as an oil. LRMS: M+=389.

Example 5
Synthesis of 1'-(Diethylcarbamyl)-3,4-dihydrospiro[5H-1-benzazepine-2(1H)-4'-piperidin]-5-one (15)

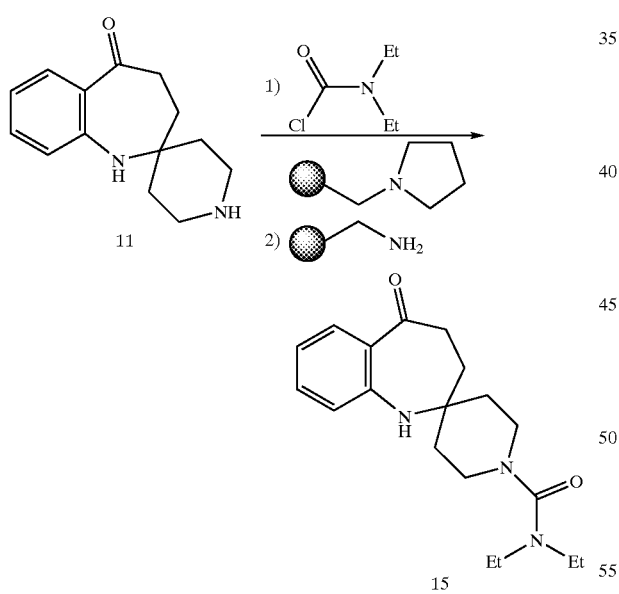

To a solution of diamine 11 (10 mg, 0.043 mmol) in anhydrous CH₂Cl₂ (0.5 mL) was added diethyl carbamyl chloride (11 mg, 0.052 mmol) and piperidinomethyl polystyrene (3.5 mmol/g resin, 13 mg). The reaction was agitated at room temperature for 4 h, and the reaction mixture was then filtered. To the filtrate was added AM resin (3.21 mmol/g resin, 16 mg) and the reaction mixture was agitated for 8 h. The reaction was filtered and the filtrate was concentrated to yield 15 (7 mg, 0.021 mmol, 49%) as an oil. LRMS: M+=329.

Example 6

Synthesis of 1'-(2-Naphthoyl)-3,4-dihydrospiro[5H-1-benzazepine-2(1H)-4'-piperidin]-5-one (16)

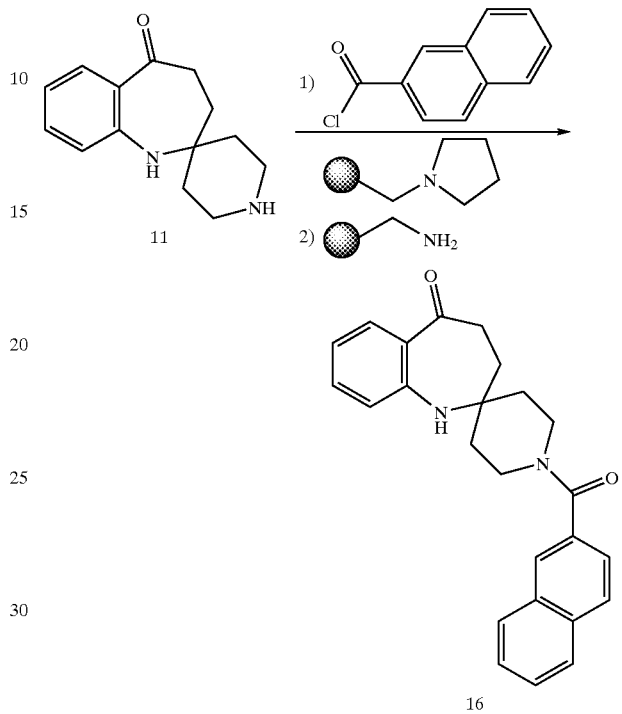

To a solution of diamine 11 (10 mg, 0.043 mmol) in anhydrous CH₂Cl₂ (0.5 mL) was added 2-naphthoyl chloride (10 mg, 0.052 mmol) and piperidinomethyl polystyrene (3.5 mmol/g resin, 13 mg). The reaction was agitated at room temperature for 4 h, and the reaction mixture was then filtered. To the filtrate was added AM resin (3.21 mmol/g resin, 16 mg) and the reaction mixture was agitated for 8 h. The reaction was filtered and the filtrate was concentrated to yield 16 (11 mg, 0.027 mmol, 67%) as an oil. LRMS: M+=384.

Example 7

Synthesis of 1'-(Benzenesulfonyl)-3,4-dihydrospiro[5H-1-benzazepine-2(1H)-4'-piperidin]-5-one (17)

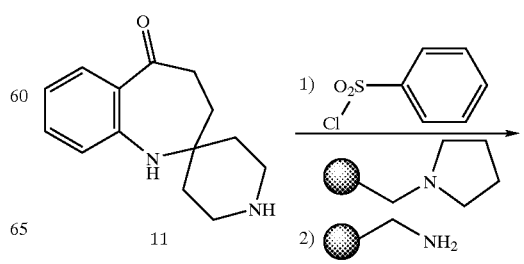

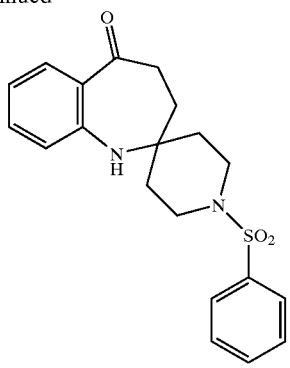

17

To a solution of diamine 11 (10 mg, 0.043 mmol) in anhydrous $CH_2Cl_2$ (0.5 mL) was added benzenesulfonyl chloride (10 mg, 0.052 mmol) and piperidinomethyl polystyrene (3.5 mmol/g resin, 13 mg). The reaction was agitated at room temperature for 4 h, and the reaction mixture was then filtered. To the filtrate was added AM resin (3,21 mmol/g resin, 16 mg) and the reaction mixture was agitated for 8 h. The reaction was filtered and the filtrate was concentrated to yield 17 (12 mg, 0.031 mmol, 73%) as an oil. LRMS: M+=369.

Example 8
Synthesis of 1'-(4-Trifluoromethoxybenzyl)-3,4-dihydrospiro[5H-1-benzazepine-2(1H),4'-piperidin]-5-one (18)

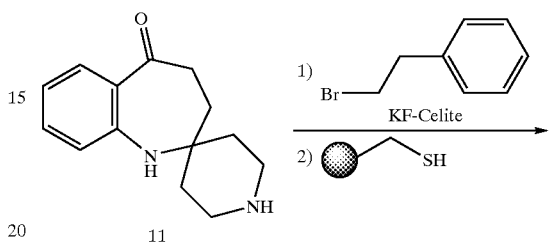

11

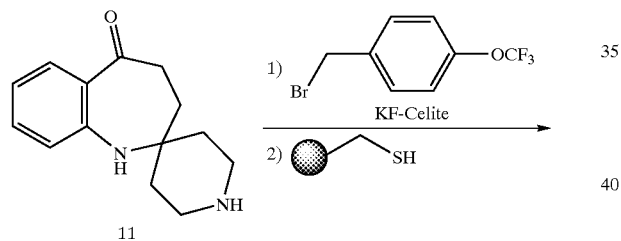

18

A solution of diamine 11 (5 mg, 0.022 mmol) in anhydrous THF (0.2 mL), KF-Celite (12.6 mg, 0.109 mmol), and 4-trifluoromethoxybenzyl bromide (5.22 μL, 0.033 mmol) was agitated at RT for 16 h. The reaction was filtered and piperidinomethyl polystyrene N-2-(mercaptoethyl) aminoethyl polystyrene (26 mg, 0.033 mmol) was added to the filtrate. The reaction was agitated for another 12 h and then filtered. The filtrate was concentrated to yield 18 (6 mg, 0.015 mmol, 68%) as an oil. LRMS: M+=403.

Example 9

Synthesis of 1'-(ethylbenzyl)-3,4-dihydrospiro[5H-1-benzazepine-2(1H)-4'-piperidin]-5-one (19)

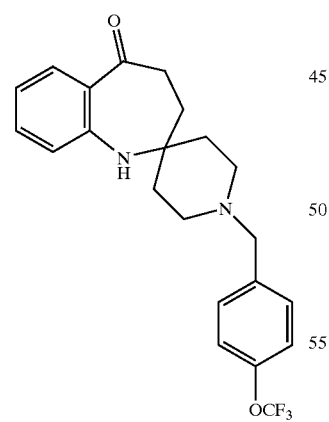

19

A solution of diamine 11 (20 mg, 0.087 mmol) in anhydrous THF (0.8 mL), KF-Celite (50 mg, 0.432 mmol), and 2-phenethyl bromide (17.8 μL, 0.130 mmol) was agitated at RT for 16 h. The reaction was filtered and piperidinomethyl polystyrene N-2-(mercaptoethyl)aminoethyl polystyrene (113 mg, 0.099 mmol) was added to the filtrate. The reaction was agitated for another 12 h and then filtered. The filtrate was concentrated to yield 19 (33.1 mg, 0.098 mmol, 100%) as an oil. LRMS: M+=334.

Example 10

Synthesis of 1'-(iso-nicotinyl)-3,4-dihydrospiro[5H-1-benzazepine-2(1H)-4'-piperidin]-5-one (20)

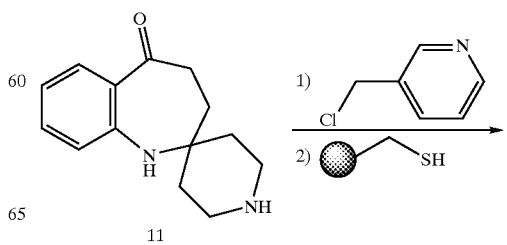

11

-continued

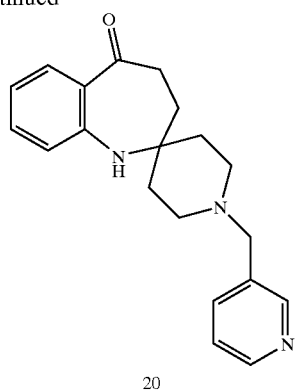
20

A solution of diamine 11 (5 mg, 0.022 mmol) in anhydrous THF and iso-nicotinyl chloride (3.3 mg, 0.026 mmol) was agitated at room temperature for 16 h, and piperidinomethyl polystyrene N-2-(mercaptoethyl)aminoethyl polystyrene (26 mg, 0.033 mmol) was then added. The reaction was agitated for another 12 h and then filtered. The filtrate was concentrated to yield 20 (5 mg, 0.016 mmol, 71%) as an oil. LRMS: M+=321.

Example 11

Synthesis of 1'-(2-methylbenzimidazole)-3,4-dihydrospiro[5H-1-benzazepine-2(1)H-4'-piperidin]-5-one (21)

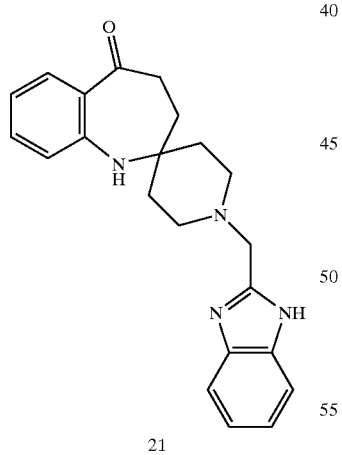

A solution of diamine 11 (5 mg, 0.022 mmol) in anhydrous THF and 2-chloromethylbenzimidazole (4.7 mg, 0.026 mmol) was agitated at room temperature for 16 h, and piperidinomethyl polystyrene N-2-(mercaptoethyl)aminoethyl polystyrene (26 mg, 0.033 mmol) was then added. The reaction was agitated for another 12 h and then filtered. The filtrate was concentrated and the crude oil was purified via reverse phase HPLC (1:1 CH$_3$CN:H$_2$O) to yield 21 (9 mg, 0.024 mmol, 100%). LRMS: M+=360.

Example 12

Synthesis of 1'-(Methyl-(4-methylbenzoate))-3,4-dihydrospiro[5H-1-benzazepine-2(1H),4'-piperidin]-5-one (22)

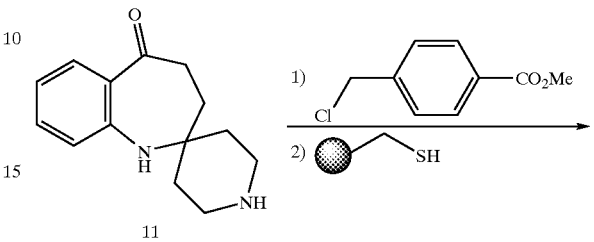

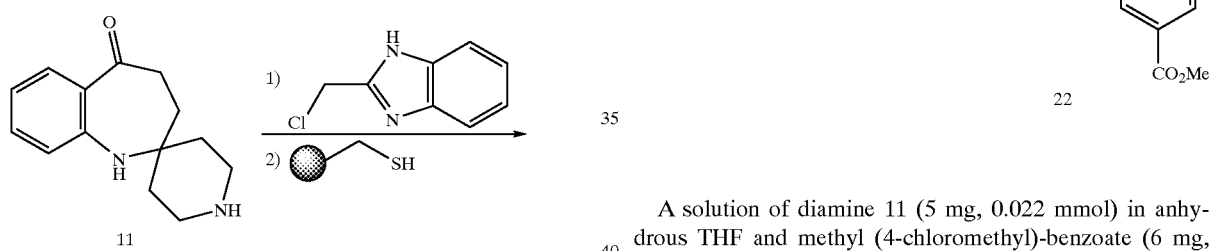

A solution of diamine 11 (5 mg, 0.022 mmol) in anhydrous THF and methyl (4-chloromethyl)-benzoate (6 mg, 0.026 mmol) was agitated at room temperature for 16 h, and piperidinomethyl polystyrene N-2-(mercaptoethyl)aminoethyl polystyrene (26 mg, 0.033 mmol) was then added. The reaction was agitated for another 12 h and then filtered. The filtrate was concentrated and the crude oil was purified using reverse phase HPLC (1:1 CH$_3$CN:H$_2$O) to yield 22 (6 mg, 0.016 mmol, 72%). LRMS: M+=378.

Example 13

Synthesis of 1'-(3-methyl-3-butene)-3,4-dihydrospiro[5H-1-benzazepine-2(1H)-4'-piperidin]-5-one (23)

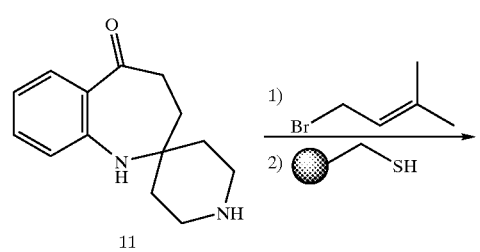

-continued

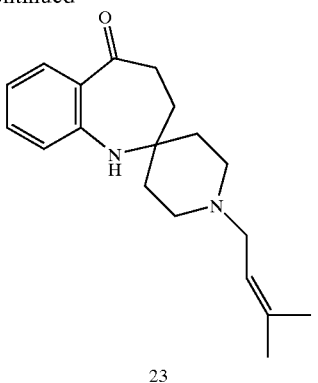

23

A solution of diamine 11 (5 mg, 0.022 mmol) in anhydrous THF and 1-bromo-3-methyl-3-butene (4 mg, 0.026 mmol) was agitated at room temperature for 16 h, and piperidinomethyl polystyrene N-2-(mercaptoethyl)aminoethyl polystyrene (26 mg, 0.033 mmol) was then added. The reaction was agitated for another 12 h and then filtered. The filtrate was concentrated to yield 23 (6 mg, 0.020 mmol, 91%) as an oil. LRMS: M+=298.

Example 14

Synthesis of 1'-(4-cyanobenzyl)-3,4-dihydrospiro[5H-1-benzazepine-2(1H),4'-piperidin]-5-one (24)

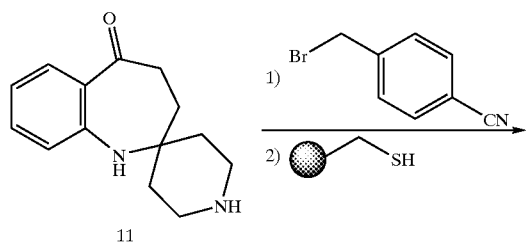

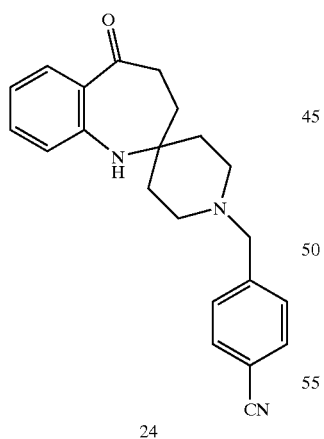

24

A solution of diamine 11 (5 mg, 0.022 mmol) in anhydrous THF and 4-cyanobenzyl bromide (5 mg, 0.026 mmol) was agitated at room temperature for 16 h, and piperidinomethyl polystyrene N-2-(mercaptoethyl)aminoethyl polystyrene (26 mg, 0.033 mmol) was then added. The reaction was agitated for another 12 h and then filtered. The filtrate was concentrated to yield 24 (5 mg, 0.014 mmol, 66%) as an oil. LRMS: M+=345.

Example 15

Synthesis of 1'-(ethylhexane-3,4-dihydrospiro[5H-1-benzazepine-2(1H)-4'-piperidin]-5-one (25)

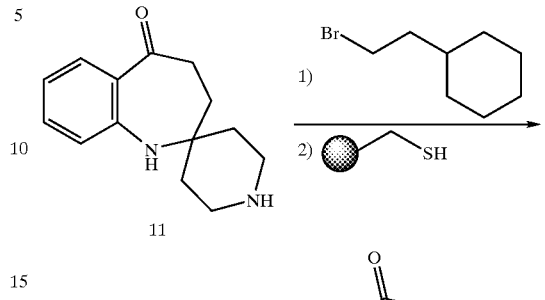

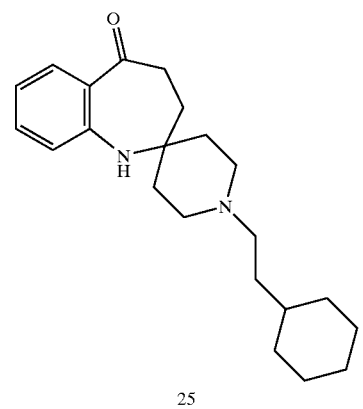

25

A solution of diamine 11 (5 mg, 0.022 mmol) in anhydrous THF and (2-bromoethyl)cyclohexane (5 mg, 0.026 mmol) was agitated at room temperature for 16 h, and piperidinomethyl polystyrene N-2-(mercaptoethyl)aminoethyl polystyrene (26 mg, 0.033 mmol) was then added. The reaction was agitated for another 12 h and then filtered. The filtrate was concentrated to yield 25 (5 mg, 0.015 mmol, 66%) as an oil. LRMS: M+=340.

Example 16

Synthesis of 1'-(allyl)-3,4-dihydrospiro[5H-1-benzazepine-2(1H)-4'-piperidin]-5-one (26)

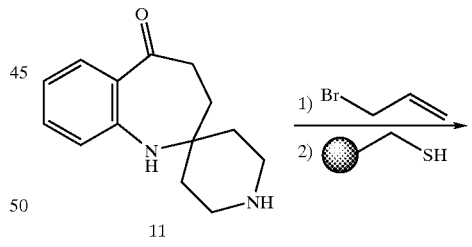

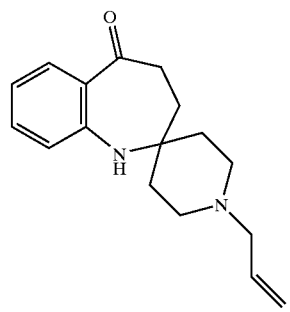

26

A solution of diamine 11 (5 mg, 0.022 mmol) in anhydrous THF and allyl bromide (3.1 mg, 0.026 mmol) was agitated at room temperature for 16 h, and piperidinomethyl polystyrene N-2-(mercaptoethyl)aminoethyl polystyrene (26 mg, 0.033 mmol) was then added. The reaction was agitated for another 12 h and then filtered. The filtrate was concentrated to yield 26 (5 mg, 0.019 mmol, 84%) as an oil. LRMS: M+=270.

Example 17

Synthesis of 1'-(3,3-dimethylbutane)-3.4-dihydrospiro[5H-1-benzazepine-2(1H)-4'-piperidin]-5-one (27)

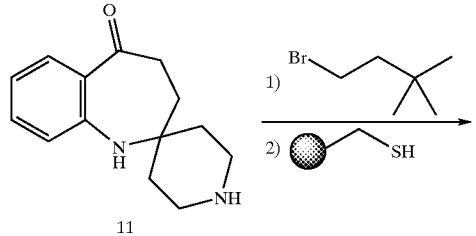

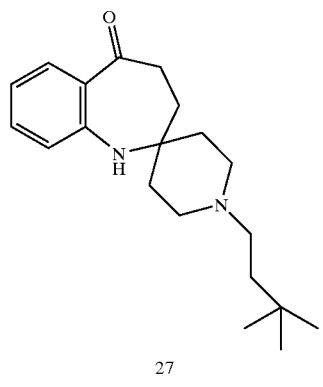

A solution of diamine 11 (5 mg, 0.022 mmol) in anhydrous THF and 1-bromo-3,3-dimethylbutane (4.3 mg, 0.026 mmol) was agitated at room temperature for 16 h, and piperidinomethyl polystyrene N-2-(mercaptoethyl) aminoethyl polystyrene (26 mg, 0.033 mmol) was then added. The reaction was agitated for another 12 h and then filtered. The filtrate was concentrated to yield 27 (5 mg, 0.016 mmol, 72%) as an oil. LRMS: M+=314.

Example 18

Synthesis of 1'-(epoxymethyl)-3,4-dihydrospiro[5H-1-benzazepine-2(1H)-4'-piperidin]-5-one (28)

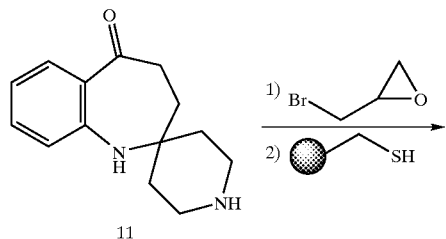

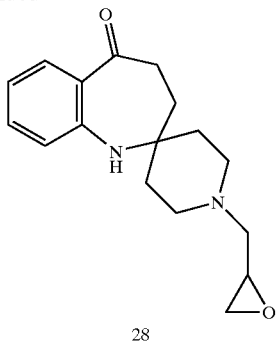

A solution of diamine 11 (5 mg, 0.022 mmol) in anhydrous THF and epibromohydrin (3.5 mg, 0.026 mmol) was agitated at RT for 16 h, and piperidinomethyl polystyrene N-2-(mercaptoethyl)aminoethyl polystyrene (26 mg, 0.033 mmol) was then added. The reaction was agitated for another 12 h and then filtered. The filtrate was concentrated to yield 28 (4 mg, 0.014 mmol, 64%) as an oil. LRMS: M+=286.

Example 19

Synthesis of 1'-(3-methylbutane)-3,4-dihydrospiro[5H-1-benzazepine-2(1H)-4'-piperidin]-5-one (29)

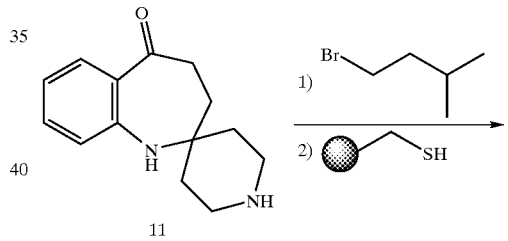

A solution of diamine 11 (5 mg, 0.022 mmol) in anhydrous THF and 1-bromo-3-methylbutane (3.90 mg, 0.026 mmol) was agitated at RT for 16 h, and piperidinomethyl polystyrene N-2-(mercaptoethyl)aminoethyl polystyrene (26 mg, 0.033 mmol) was then added. The reaction was agitated for another 12 h and then filtered. The filtrate was concentrated to yield 29 (5 mg, 0.017 mmol, 76%) as an oil. LRMS: M+=286.

Example 20
Synthesis of 1'-(2-methyl-imidazole)-3,4-dihydrospiro[5H-1-benzazepine-2(1H)-4'-piperidin]-5-one (30)

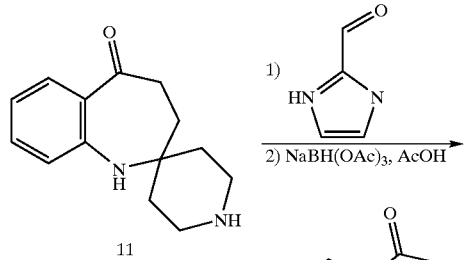

A solution of amine 11 (20 mg, 0.87 mmol) and 2-imidazole carboxaldehyde (10 mg, 0.10 mmol) in anhydrous DMF (0.9 mL) was agitated at RT. After 20 h, NaBH(OAc)$_3$ (14 mg, 0.066 mmol) and AcOH (9 μL) were added and the reaction was agitated for another 12 h. The reaction was filtered and the filtrate was purified using reverse phase chromatography (60:40 CH$_3$CN:H$_2$O) to yield 30 (16 mg, 0.052 mmol, 60%) as an oil. LRMS: M+=310.

Example 21
Synthesis of 1'-(4-fluorobenzyl)-3,4-dihydrospiro[5H-1-benzazepine-2(1H)-4'-piperidin]-5-one (31)

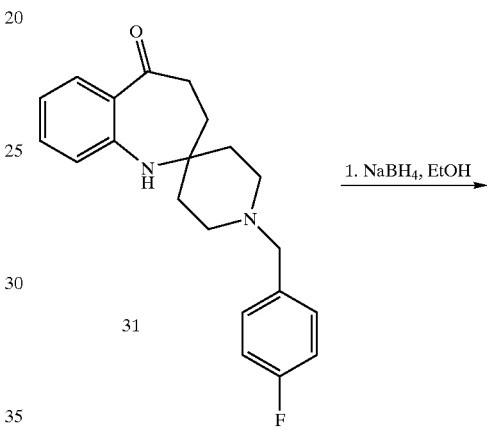

A solution of amine 11 (306 mg, 1.3 mmol) and 4-fluorobenzaldehyde (198 mg, 1.6 mmol) in anhydrous DMF (5 mL) was agitated at RT. After 20 h, NaBH(OAc)$_3$ (413 mg, 1.95 mmol) and AcOH (50 μL) were added and the reaction was agitated for another 12 h. The reaction was filtered and the filtrate was purified using reverse phase chromatography (60:40 CH$_3$CN:H$_2$O) to yield 31 (188 mg, 0.56 mmol, 43%) as a yellow oil. $^1$H NMR (CDCl$_3$) δ 7.84 (1H, d, J=7.2 Hz), 7.73 (1H, d, J=7.3 Hz), 7.32 (1H, m), 7.10 (1H, m), 6.93 (2H, m), 4.41 (1H, s), 4.16 (2H, s), 3.51–3.32 (2H, m), 2.97 (2H, m), 2.74 (6H, m), 2.20–1.90 (4H, m), IR (NaCl, thin film) 3426, 1675, 1508, 1467, 1436, 1214, 1133 cm$^{-1}$; LRMS: M+=338.

Example 22

Synthesis of 1'-(4-fluorobenzyl)-3,4-dihydrospiro[5H-1-benzazepine-2(1H)-4'-piperidin]-5-ol (32)

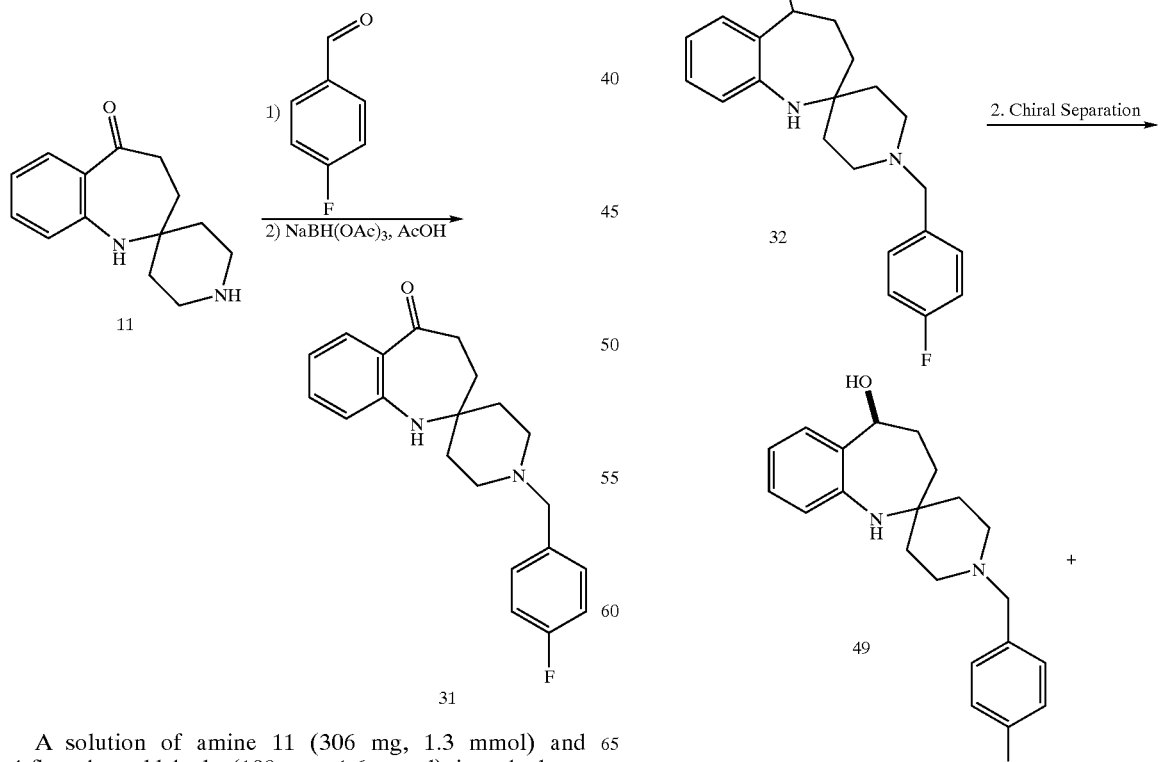

-continued

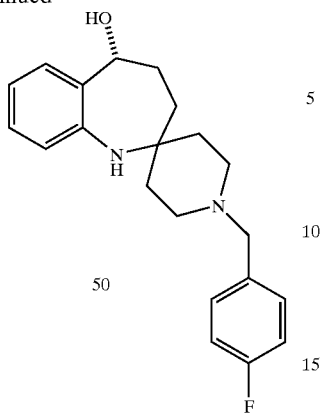

50

A solution of ketone 31 (40 mg, 0.174 mmol) and NaBH$_4$ (9.9 mg, 0.261 mmol) in anhydrous EtOH (0.5 mL) was stirred at RT for 8 h. The reaction was concentrated and the crude material was purified by reverse phase chromatography (60:40 CH$_3$CN:H$_2$O) to yield 32 as an oil (32 mg, 0.095 mmol, 55%). LRMS: M+=336. Racemic 32 was separated into enantiomers 49 and 50, using a chiral AD column (80:20:0.1 hexane:EtOH:diethylamine). $^1$H (CDCl$_3$) δ 7.29–6.76 (8H, m), 4.75 (1H, s), 4.08 (1H, m), 3.50 (2H, s), 2.63–0.96 (12H, m).

Example 23

Synthesis of 1'-(4-Fluorobenzyl)-spiro[5-1-benzazepine-2(1H),4'-piperidin]-5-ol (35)

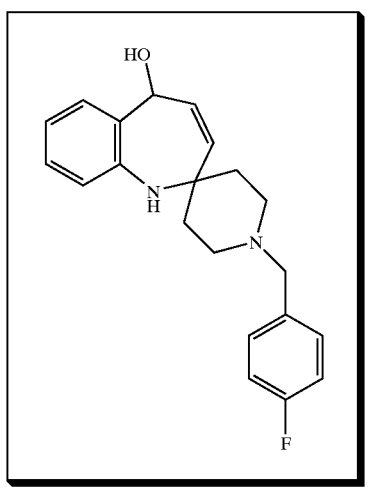

1. Synthesis of 1'-Spiro[5-1-benzazepine-2(1H)-4'-piperidin]-5-one (33).

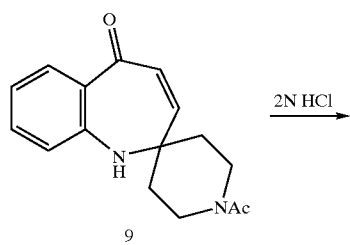

9

-continued

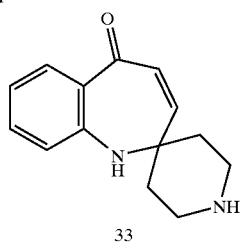

33

A solution of acetate 9 (55 mg, 0.20 mmol) in 2 N HCl (0.8 mL) was heated at 80° C. After 8 h, the reaction was cooled to RT and diluted with 5 N NaOH to a pH~11. The aqueous layer was extracted with EtOAc (3×10 mL). The combined organic layer was dried over Na$_2$SO$_4$ and concentrated to yield 33 as an oil (34.6 mg, 0.11 mmol, 76%). LRMS: M+=228.

2. Synthesis of 1'-(4-Fluorobenzyl)-spiro[5-1-benzazepine-2(1H)-4'-piperidin]-5-one (34).

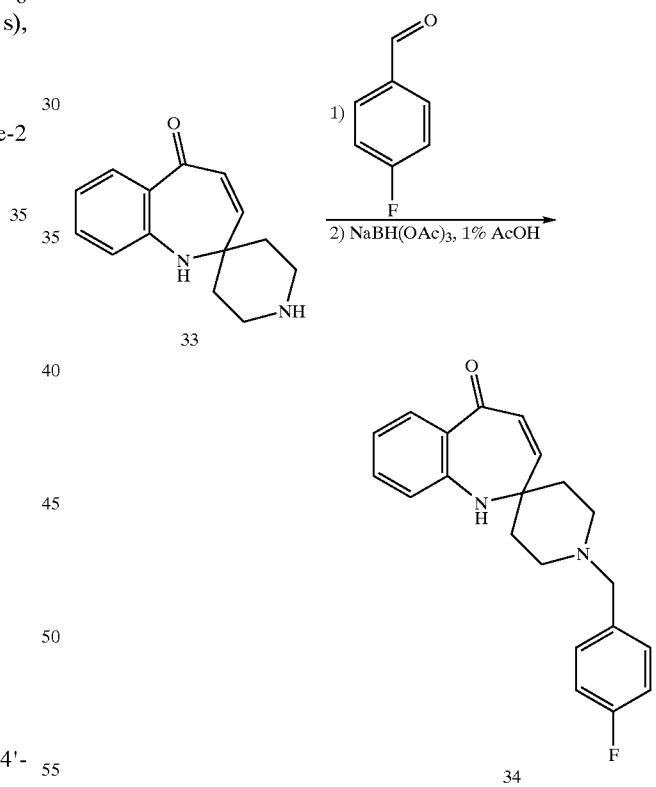

A solution of amine 33 (36.4 mg, 0.11 mmol) and 4-fluorobenzaldehyde (16.1 mg, 0.13 mmol) in anhydrous DMF (0.5 mL) was agitated at RT. After 20 h, NaBH(OAc)$_3$ (27.3 mg, 0.13 mmol) and AcOH (50 μL) were added and the reaction was agitated for another 12 h. The reaction was filtered and the filtrate was purified using reverse phase chromatography (60:40 CH$_3$CN:H$_2$O) to yield 34 (33 mg, 0.097 mmol, 89%) as an oil. LRMS: M+=338.

3. Synthesis of 1'-(4-Fluorobenzyl)-spiro[5-1-benzazepine-2(1H)-4'-piperidin]-5-ol (35).

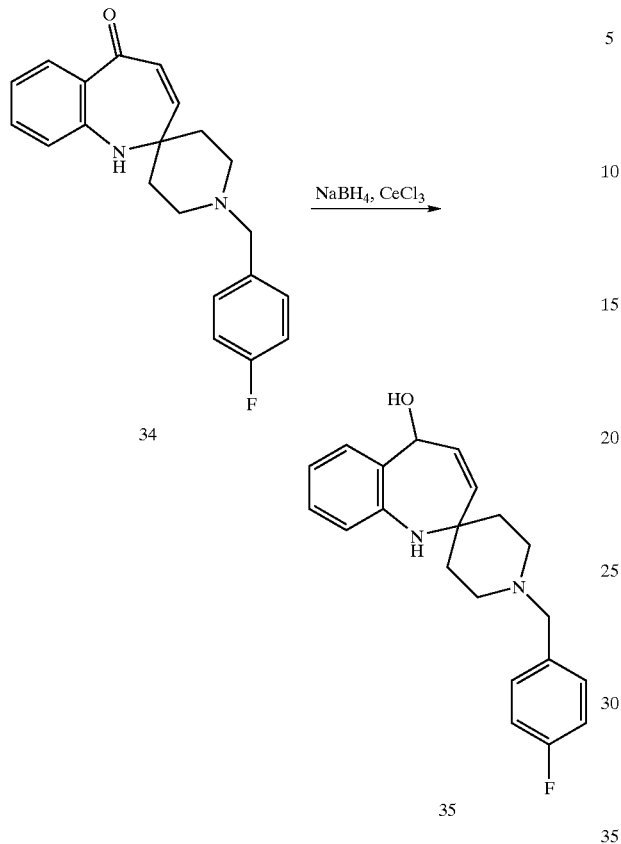

A solution of ketone 34 (20 mg, 0.059 mmol), NaBH$_4$ (4.4 mg, 0.20 mmol) and CeCl$_3$ (14.5 mg, 0.059 mmol) in anhydrous EtOH (0.5 mL) was stirred at room temperature for 48 h. The reaction was concentrated and the crude material was purified by reverse phase chromatography (70:30 CH$_3$CN:H$_2$O) to yield 35 as an oil (15 mg, 0.044 mmol, 75%). LRMS: M+=336.

Example 24

Synthesis of (R)-1'-(4-fluorobenzyl)-3,4-dihydrospiro[5H-1-benzazepine-2(1H)-4'-piperidin]-5-amine and (S)-1'-(4-fluorobenzyl)-3,4-dihydrospiro[5H-1-benzazepine-2(1H)-4'-piperidin]-5-amine

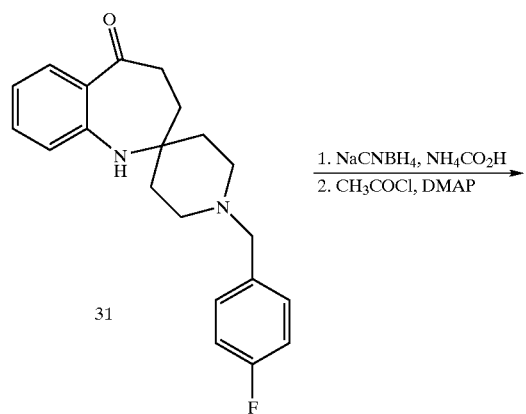

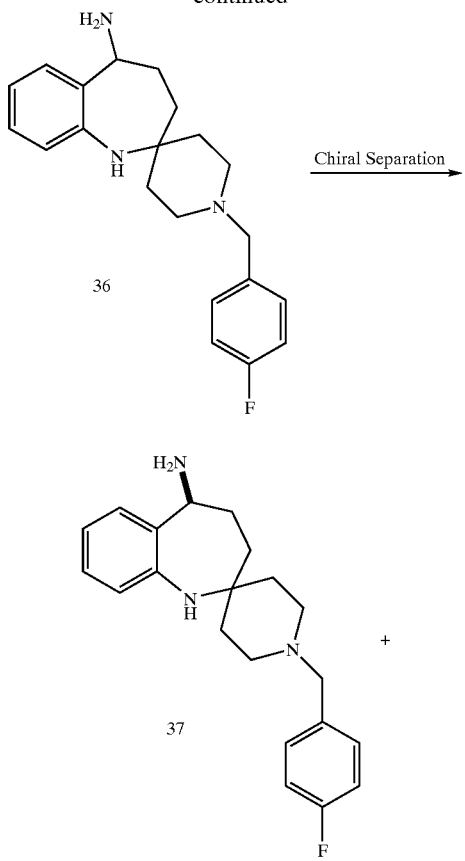

A solution of 31 (200 mg, 0.59 mmol), NaBH$_3$CN (258 mg, 4.11 mmole), and ammonium acetate (1.37 g, 17.17 mmol) in anhydrous i-PrOH (4.3 mL) was stirred at 50° C. After 2 h, the reaction mixture was cooled down to RT. i-PrOH was removed in vacuo to yield a crude oil (282.6 mg), which was dissolved in anhydrous dichloromethane (3 mL). Acetyl chloride (78.3 mg, 0.97 mmol) and DMAP (152 mg, 1.24 mmol) were added. The reaction proceeded at RT overnight. The reaction mixture was concentrated to yield crude 36, which was dissolved in i-PrOH (1 mg/mL). The enantiomers 37 and 38 were separated using a chiral AD coloum (80:20:0.1 hexane:EtOH:diethylamine). LRMS: M+382.

Example 25

Synthesis of (R)-1'-(4-fluorobenzyl)-3,4-dihydrospiro[5H-1-benzazepine-2(1H)-4'-piperidin]-5-amine and (S)-1'-(4-fluorobenzyl)-3,4-dihydrospiro[5H-1-benzazepine-2(1H)-4'-piperidin]-5-formamide

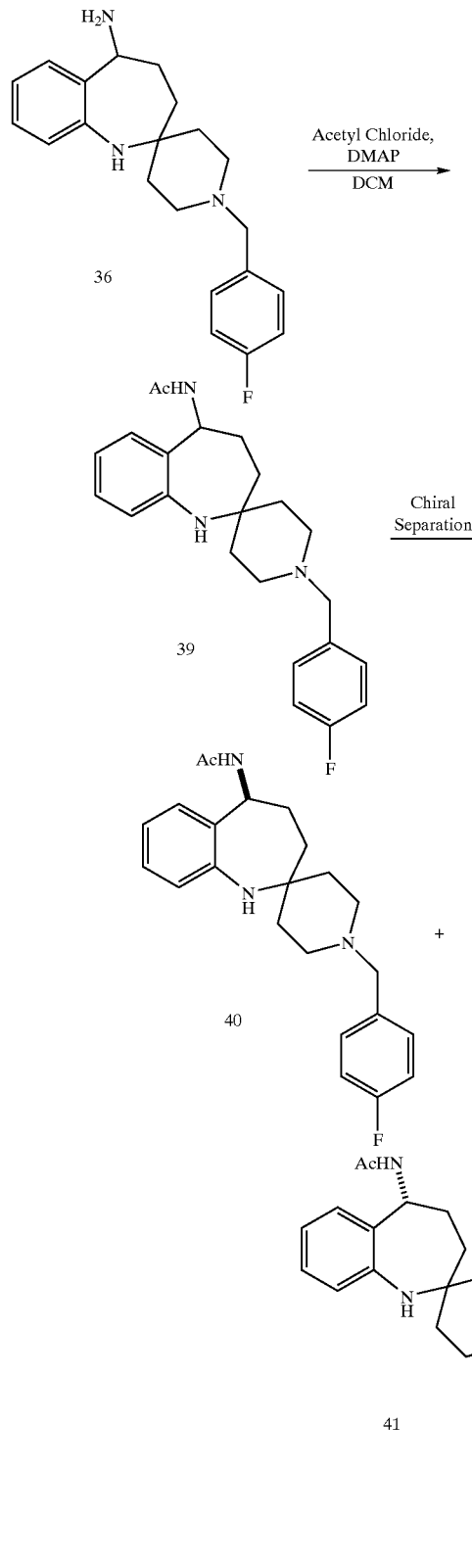

A solution of amine 36 (282.6 mg, 0.74 mmol), acetyl chloride (78.3 mg, 0.10 mmol), and DMAP (152 mg, 1.24 mmol) in dichloromethane (15 mL) was stirred at RT. After 12 h, the reaction mixture was concentrated and the crude material was taken up in dichloromethane (30 mL). This solution was filtered and the filtrate was concentrated again to yield an oil. This oil was purified using a chiral AD coloum (80:20:0.1 hexane:EtOH:diethylamine) to yield racemate 39, as well as enantiomers 40 and 41. LRMS 322 (381-NHAc).

Example 26

Synthesis of 3,4-Dihydrospiro[5H-1-benzazepine-2(1H)-4'-piperidin]-5-one-1'-carboxylic Acid (2,6-dimethyl-phenyl)-amide

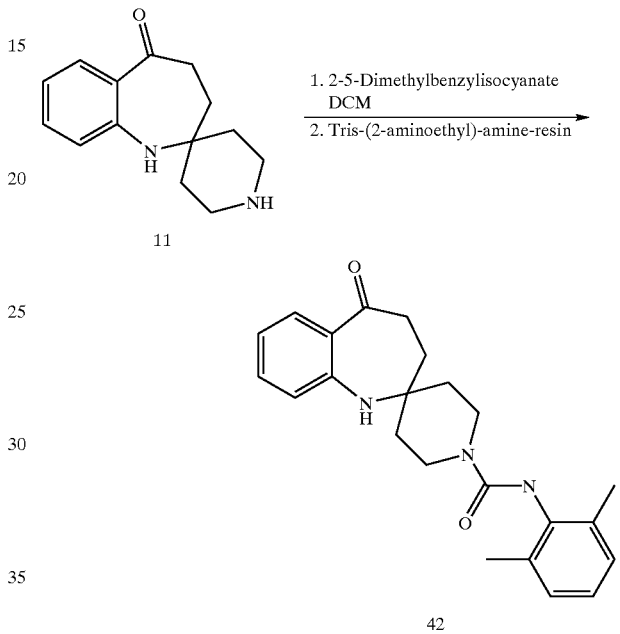

A solution of amine 11 (10 mg, 0.043 mmol) and isocyanate (7.7 mg, 0.52 mmol) in dichloromethane (0.5 mL) was shaken at RT. After 12 h, tris-(2-aminoethyl)-amine resin (5 mg; loading>2.0 mmol/g resin) was added to the reaction mixture and stirring continued for an additional 4 h. The reaction mixture was filtered and the filtrate was concentrated to yield 42 as an oil (8.9 mg,). LRMS: M+377

Example 27

Synthesis of 1'-(4-fluorobenzyl)-3,4-dihydrospiro[benzazepine-2(1H)-4'-piperidine (43)

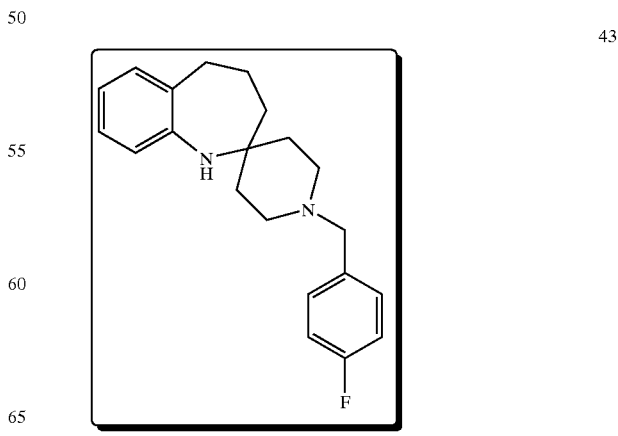

Synthesis of 1'-(4-fluorobenzyl)-3,4-dihydrospiro[5H-1-benzazepine-2(1H)-4'-piperidin]-5-tosylate (44)

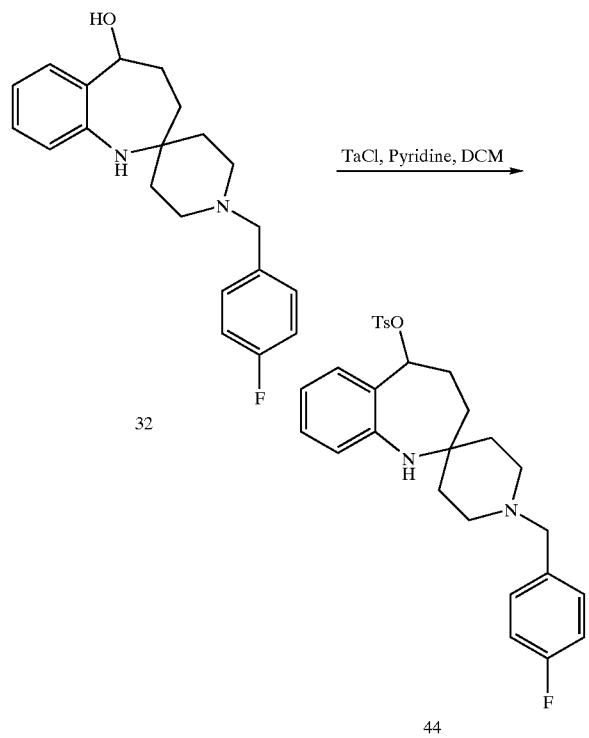

A solution of 32 (56 mg, 0.165 mmol) and pyridine (40 mL, 0.495 mmol) in anydrous dichloromethane (2.0 mL) was cooled in an ice bath. TsCl (37.8 mg, 0.198 mmol) dissolved in dichloromethane (0.5 mL) was added dropwise to the cooled stirring reaction mixture. After completion of the addition, the reaction continued stirring at RT. After 48 h, the reaction was quenched with water. The aqueous layer was extracted with EtOAc (3×10 mL). The combined organics were dried over Na$_2$SO$_4$ and concentrated to yield an oil. The crude material was purified using a basic alumina prep-plate (4:1 hexanes:EtOAc) to yield 44. $^1$H (CDCl$_3$) δ 7.81 (2H, s), 7.24 (2H, s), 7.34–6.94 (8H, m), 6.40 (1H, m), 5.77 (1H, m), 4.26 (1H, s), 4.18 (4H, m), 2.38 (3H, s), 2.0–1.27 (8H, m). LRMS:322 (494.2-tosyl group).

Synthesis of 1'-(4-fluorobenzyl)-3,4-dihydrospiro[benzazepine-2(1H)-4'-piperidine] (43)

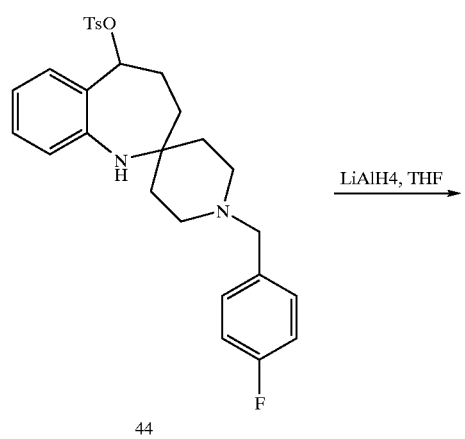

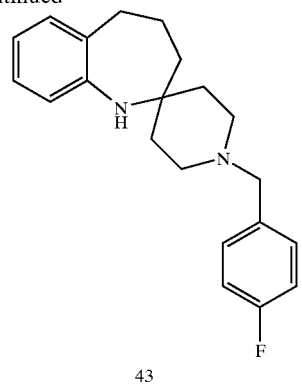

Tosylate 44 (25.4 mg, 0.051 mmol) in anhydrous THF (0.7 mL) was added to a slurry of lithium aluminum hydride (9.3 mg, 0.244 mmol) in THF (0.1 mL). After completion of the addition, the reaction mixture was heated to reflux (60° C.). After 1 h, the reaction mixture was cooled to RT and quenched with water. The aqueous layer was extracted with EtOAc (3×2 mL). The combined organics were dried over Na$_2$SO$_4$ and concentrated to yield an oil. The crude material was purified using a basic alumina prep plate (100% EtOAc) to yield 43. $^1$H (CDCl$_3$) δ 7.24–6.94 (8H, m), 3.77 (2H, m), 3.51 (1H, s), 2.6–1.15 (12H, m). LRMS: M+322.

Example 28

Synthesis of 1'-(2-hydroxy-phenethyl)-3,4-dihydrospiro[5H-1-benzazepine-2(1H)-4'-piperidin]-5-one

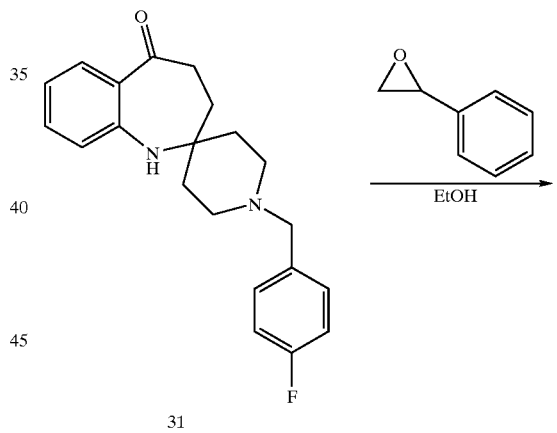

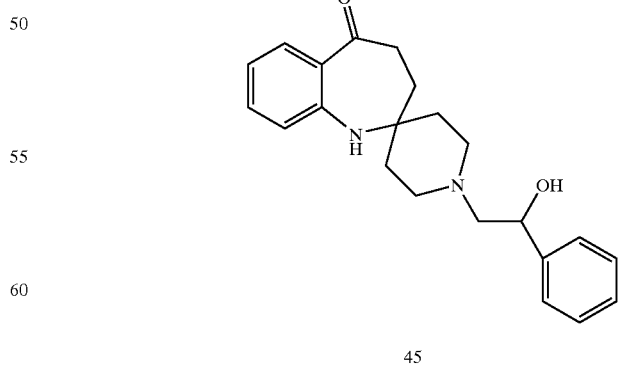

A solution of 31 (1.0 g, 2.96 mmol) and styrene oxide (742 μL, 6.51 mmol) dissolved in EtOH (10 mL) was heated to 50° C. After 4 h, the reaction mixture was cooled to RT.

The crude material was concentrated in vacuo to remove excess styrene oxide. No further purification was necessary and 45 was obtained as a yellow oil (1.0 g, 2.86 mmol, 94%). $^1$H (CDCl$_3$) δ 7.86 (1H, m), 7.38 (6H, m), 6.86 (1H, t, J=6 Hz), 6.80 (1H, d, J=8 Hz), 6.74 (2H, m), 5.34 (2H, s), 4.77 (1H, m), 3.96 (1H, s), 2.84–1.30 (12H, m) LRMS: 351.

Example 29
Synthesis of 1'-(1-Methyl-4-fluorobenzyl)-3,4-dihydrospiro[5H-1-benzazepine-2(1H)-4'-piperidin]-5-one

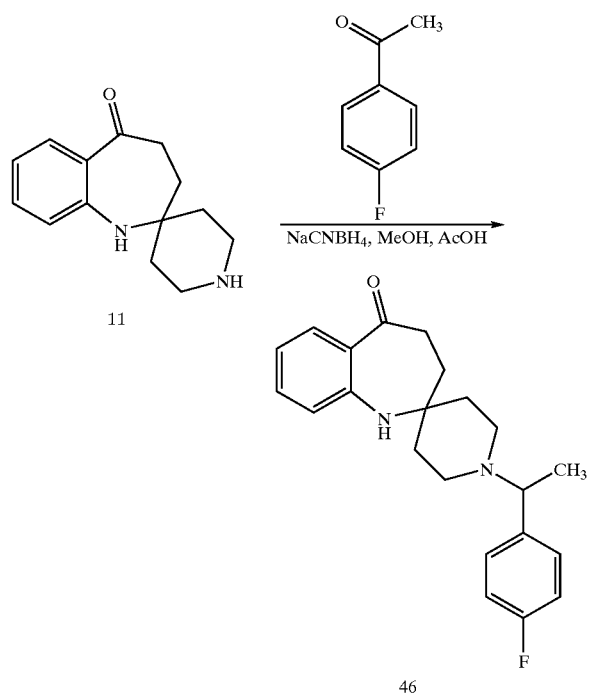

A solution of 11 (250 mg, 0.001 mole) and 4-fluoroacetophenone (792 mL, 0.007 mole) was dissolved in acidified MeOH and then heated at reflux. After 48 h, the reaction was cooled to RT and concentrated in vacuo. The crude material was purified using silica gel chromatography (50:50 hexanes: EtOAc) to yield 46 (200 mg, 70.4 mol, 57%) as an oil. LRMS: M+352.

Example 30
Synthesis of 1-(4-fluorobenzyl)-4'methylidene-3',4'-dihydrospiro[piperidine-4,2'(1'H)-quinoline

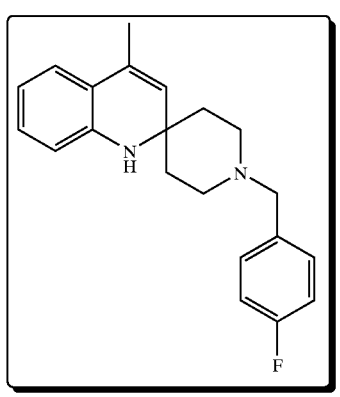

Synthesis of 4 methylidene-3',4'-dihydrospiro[piperidine-4,2'(1'H)-quinoline

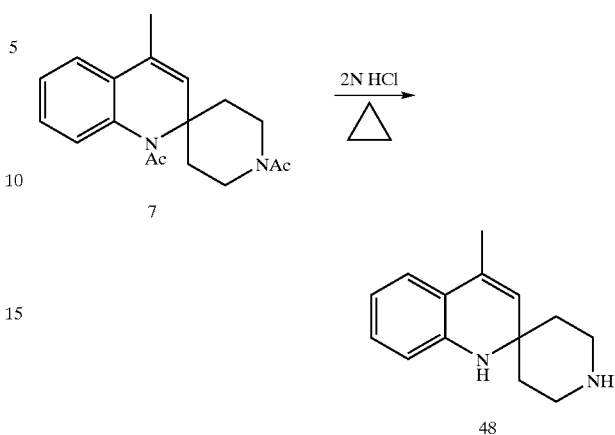

The diacetate 7 (50 mg, 0.123 mmol) was dissolved in 2N HCl in EtOH (0.15 mL). The reaction mixture was heated to 60° C. and monitored by TLC. Once all the starting material was consumed, the reaction was cooled down to RT and basified with 5N NaOH. The aqueous layer was extracted with dichloromethane (3×3 mL). The combined organic layers were dried over Na$_2$SO$_4$ and concentrated to yield 48 (18.2 mg, 0.071 mmol, 58%). No purification was necessary. LRMS: M+256.

Synthesis of 1-(4-fluorobenzyl)-4'methylidene-3',4'-dihydrospiro[piperidine-4,2'(1'H)-quinoline

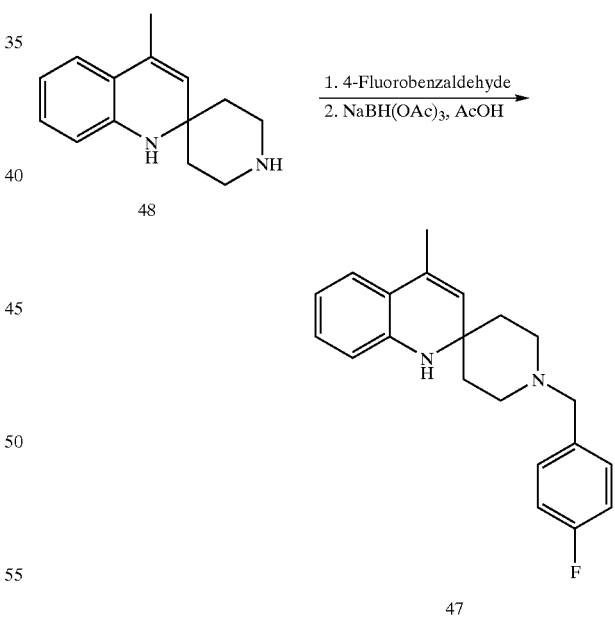

A solution of 48 (18.2 mg, 0.071 mmol) and 4-flourobenzaldehyde (9.14 μL, 0.085 mmol) in DMF (0.4 mL) was shaken at RT. After 12 h, NaBH(OAc)$_3$ (22.5 mg, 0.107 mmol) and acetic acid (4 μL) were added to the reaction mixture. The reaction mixture was shaken at RT for another 12 h before it was filtered. The filtrate was concentrated to yield a crude material. The crude oil was purified using a silica gel prep plate (70:30 hexanes: EtOAc) to yield 47 (22 mg, 0.079 mmol, 96%). LRMS:322.

Example 31
Synthesis of 4-(2-Bromo-phenylamino)-4-trimethylsilanyl-ethynyl-piperidine-1-carboxylic Acid tert-butyl Ester

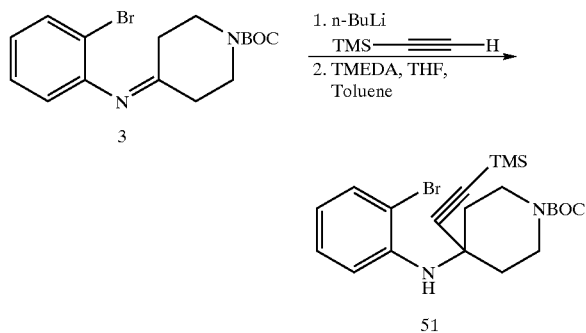

A solution of TMSpropyne (21.65 g, 0.221 moles) in anhydrous THF (60 mL) was cooled to −78° C. n-BuLi (1 M in hexanes 138.12 mL, 0.221 moles) solution was added dropwise to the cooled stirring reaction mixture. After completion of the addition, the reaction continued stirring at −78° C. After 1 h, the in situ prepared Li-acetylene was added via cannula to a solution of imine 3 (51.82 g, 0.147 moles) in toluene (251 mL) and TMEDA (33.32 mL). After completion of addition the reaction continued stirring at RT for 3 days. The reaction mixture was quenched with water and aqueous layer was extracted with ether (3×200 mL). Combined organic layers were dried over $Na_2SO_4$ and concentrated to yield 51 as an oil (34.21 g, 0.76 moles, 52%). No purification was required. $^1H$ ($CDCl_3$) δ 7.40 (1H, s), 7.26 (1H, m), 6.89 (1H, m), 6.77 (1H, m), 4.50 (1H, s), 3.40 (4H, m), 2.33 (1H, s), 1.88–1.76 (2H, m),1.60 (9H, s), 0.30 (9H, s).

Example 32
Synthesis of Spiro[(3-methylene)-indole-2,4'-piperidine]-1-carboxylic Acid tert-butyl Ester

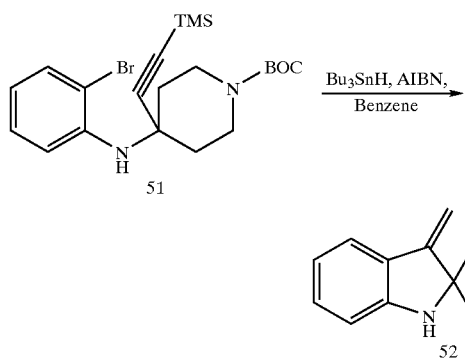

A solution of alkyne 51 (89.3 mg, 0.198 mmol) in anhydrous benzene (4.5 mL) and AIBN (5 mg, 0.030 mmol) was heated to 70° C. Tributyltin hydride (0.106 mL, 0.397 mmol) was added dropwise to the stirring reaction mixture. After completion of addition, the reaction mixture was heated to 80° C. After 4 h the reaction was cooled down to RT and concentrated in vacuo to yield an oil. The crude material was purified using silica gel chromatography (100% hexanes-70:30 hexanes:EtOAc) to yield the spirocycle 52 (47 mg, 0.167 mmol, 79%). $^1H$ ($CDCl_3$) δ 7.39 (1H, m), 7.16 (1H, m), 6.81–6.71 (2H, m), 5.44 (1H, s), 4.84 (1H, s), 4.14 (1H, s), 4.20 (1H, m), 2.98 (2H, m), 1.71–1.64 (2H, m), 1.52 (9H, s), 1.39–1.34 (2H, m).

Example 33
Synthesis of 1-Fluorobenzyl-spiro[(3-methylene)-indole-2,4'-piperidine]

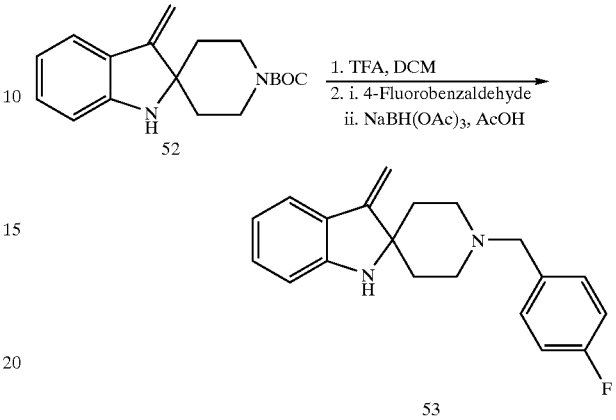

A solution of the BOC-protected amine 52 (22 mg, 0.073 mmol) in a 2N HCl/EtOH (0.8 mL/0.4 mL) solution was heated at reflux. After 2 h, the reaction mixture was cooled down to RT and basified. The aqueous layer was extracted with dichloromethane (3×5 mL) and the combined organic layers were dried over $Na_2SO_4$. The filtrate was concentrated and taken up in 0.4 mL of DMF. 4-Fluorobenzaldehyde (1.2 eq.) was added and the reaction mixture was shaken at RT. After 12 h $NaBH(OAc)_3$ (44 mg, 0.21 mmol) and AcOH (4 μL) were added. After 4 h, the reaction mixture was filtered. The filtrate was concentrated to yield 53 as an oil. No purification was necessary. LRMS: M+308.

Example 34
Synthesis of a Combinatorial Library of Compounds of the Present Invention

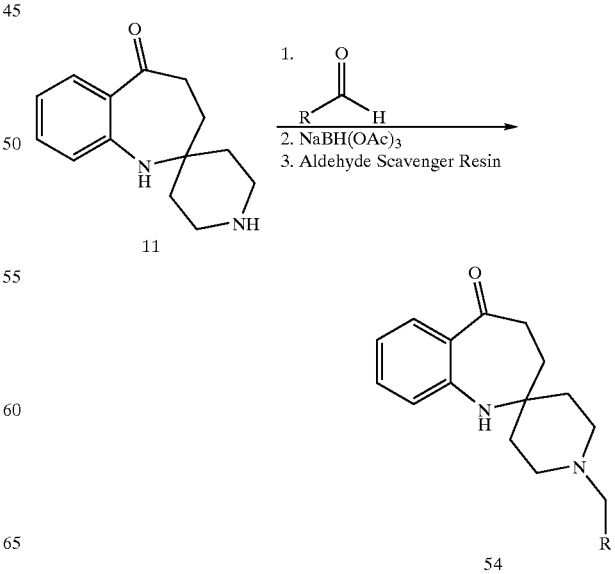

Other Scaffolds used

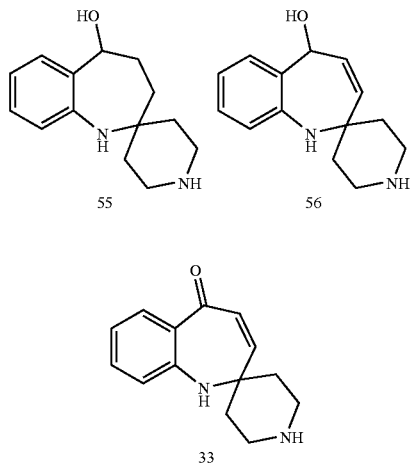

The four amine scaffolds were distributed into a 96-well reaction block (24 wells/amine scaffold). Each well contained a single amine scaffold (10 mg/200 μL DMF). 96 aldehydes dissolved in DMF were dispensed (1 aldehyde/well) (1.5 eq./100 μL). The reaction block was shaken at RT for 12 and NaBH(OAc)$_3$/AcOH (1.5 eq./1%) in 100 μL of DMF was added to each well. The reaction block was shaken at RT again for 4 h upon which the aldehyde scavenger resin N-(2-aminoethyl)aminomethyl polystyrene (5 mg, loading>1.2 mmol/g resin) was added. After 4 h of shaking the reaction block was filtered into a 96 well plate. HPLC and MS analysis confirmed presence of desired product and purity.

Example 35
Antagonism of Haloperidol Binding to Guinea Pig Sigma-1 Receptors

The compounds of the present invention exhibited biological activities, likely to be beneficial in the treatment of behavioral and neurodegenerative diseases. For example, the ability of the test compounds to displace sigma ligands in vitro was determined by the methods of de Costa et al. (*FEBS Lett.* 251:53 (1989)) and DeHaven-Hudkine et al. (*Eur. J. Pharmacol.* 227:371 (1992)) with haloperidol as the reference compound (IC$_{50}$=2.2 nM). Various candidates were identified exhibiting potent binding affinity against the sigma-1 receptor (guinea pig brain). Additionally, the compounds were screened against NK$_{1-3}$ (human), dopamine D$_{2L}$ (human), D$_{4.4}$ (human), serotonin 5-HT$_1$ (rat), and 5-HT$_2$ (rat) receptors, showing no significant affinity for them.

| Compound | % Inhibition | IC$_{50}$ (nM) |
|---|---|---|
| 10 | >50 | |
| 11 | <50 | >1000 |
| 12 | <50 | >1000 |
| 13 | <50 | >1000 |
| 14 | <50 | >1000 |
| 15 | <50 | >1000 |
| 16 | <50 | >1000 |
| 17 | <50 | >1000 |
| 18 | >50 | |
| 19 | >50 | |
| 20 | <50 | >1000 |

-continued

| Compound | % Inhibition | IC$_{50}$ (nM) |
|---|---|---|
| 21 | >50 | <1000 |
| 22 | >50 | <10 |
| 23 | >50 | |
| 24 | >50 | |
| 25 | >50 | |
| 26 | >50 | |
| 27 | >50 | |
| 28 | >50 | |
| 29 | >50 | <100 |
| 30 | >50 | <1000 |
| 31 | >50 | <10 |
| 32 | >50 | <10 |
| 34 | >50 | <100 |

Example 36
Results of Behavioral Receptor Assays for Certain Compounds of the Present Invention Various compounds of the present invention (19, 31, and 32) were evaluated in a group of assays based on mammalian cellular receptors associated with behavior. The group consisted of assays based on human dopamine D$_1$, D$_{2L}$, D$_3$, D$_{4.2}$, D$_{4.4}$, D$_{4.7}$, and D$_5$ receptors, and the human dopamine transporter; human serotonin 5-HT$_{1A}$, 5-HT$_{1B}$, 5-HT$_{1D}$, 5-HT$_{2A}$, 5-HT$_{2B}$, 5-HT$_{2C}$, 5-HT$_3$, 5-HT$_{5A}$, 5-HT$_6$, and 5-HT$_7$ receptors, and the human serotonin transporter; guinea pig 5-HT$_4$ and sigma-1 receptors; rat sigma-2 and muscarinic receptors; and human NK$_{1-3}$ receptors. The following table presents a subset of the results of these assays.

| Compound | Receptors (IC$_{50}$)* |
|---|---|
| 19 | sigma-1 (<100 nM) |
| | 5-HT$_{2A}$ (<1000 nM) |
| 31 | sigma-1 (<10 nM) |
| | sigma-2 (<1000 nM) |
| 32 | sigma-1 (<10 nM) |
| | sigma-2 (<1000 nM) |
| | 5-HT$_{2A}$ (>1000 nM) |
| | 5-HT$_{2B}$ (<1000 nM) |

*Only receptors for which the compounds displayed an IC$_{50}$ < 5 μM are tabulated.

Example 37
Absorption, Distribution, Metabolism, and Excretion (ADME) Characteristics of Certain Compounds of the Present Invention

| | Compound | | | | | |
|---|---|---|---|---|---|---|
| | 11 | 21 | 31 | 32 | 49 | 50 |
| Solution Properties | | | | | | |
| Solubility (μM) | 201.8 | 209.8 | 192.2 | 83 | 181 | 205 |
| Log D$_{7.5}$ | 0.48 | 1.22 | 2.19 | 3.7 | 1.59 | 1.62 |
| Protein Binding (% bound) | 70 | 99 | 96 | >99 | 63 | 62 |

-continued

| | Compound | | | | | |
|---|---|---|---|---|---|---|
| | 11 | 21 | 31 | 32 | 49 | 50 |
| Permeability $P_{upper} \times 10^{-6}$ cm/s | 4.7 | 1.95 | 22.94 | 22.4 | 27.5 | 25.8 |
| Metabolic Stability (% parent remaining) | 79 | 17 | 44 | 1 | 69 | 87 |
| In Vitro Metabolism (isozymes of P450) | | | | | | |
| CYP1A2* | <10 | 20 | <10 | 20 | 13 | 14 |
| CYP2C9* | <10 | 19 | <10 | 11 | 18 | 19 |
| CYP2D6* | 15 | 100 | 44 | 102 | 44 | 31 |
| CYP2C19* | <10 | 20 | 28 | 42 | 19 | 19 |
| CYP3A4* | <10 | 69 | 22 | 67 | 17 | 19 |
| Safety Assessment | | | | | | |
| GSH Level (% Control) | <10 | <10 | <10 | <10 | <10 | <10 |
| Protein Synthesis* | 42 | 14 | 65 | <10 | <10 | <10 |
| Cell Viability* | <10 | <10 | <10 | <10 | <10 | <10 |
| Caspase-3 Induction (% Induction) | <10 | <10 | <10 | <10 | <10 | <10 |
| DNA Synthesis* | <10 | 29 | <10 | <10 | <10 | <10 |
| Membrane Integrity* | <10 | <10 | <10 | <10 | <10 | <10 |
| RedOx State* | <10 | 33 | 28 | 17 | 15 | 12 |

*Reported as % inhibition.

Example 38

Results of Additional Receptor Assays Performed on Compound 31 at a Concentration of 10 $\mu$M

| Receptor | % Inhibition |
|---|---|
| Rat Adrenergic $\alpha_1$ | 21 |
| Human Adrenergic $\alpha_{2A}$ | 34 |
| Human Adrenergic $\alpha_{2C}$ | 2 |
| Human Adrenergic $\beta_1$ | 3 |
| Human Adrenergic $\beta_2$ | 15 |
| Human Adrenergic $\beta_3$ | 19 |
| Rat GABA Transporter | No Inhibition |
| Rat GABA$_A$ Agonist Site | 13 |
| Rat GABA$_A$ Benzodiazepine (Central) | 6 |
| Rat GABA$_A$ Benzodiazepine (Peripheral) | 16 |
| Rat GABA$_A$ Chloride Channel | No Inhibition |
| Rat GABA$_B$ | No Inhibition |
| Rat Glutamate, NMDA (Agonist) | No Inhibition |
| Rat Glutamate, NMDA (Glycine) | 2 |
| Rat Glutamate, NMDA (Phencyclidine) | No Inhibition |
| Rat Glutamate, NMDA (Polyamine) | 12 |
| Human Orphanin (ORL$_1$) | 12 |

Example 39
MK-801-Induced Psychosis Model
Background

The non-competitive NMDA receptor antagonist MK-801 induces stereotypies and hyperactivity in rodents (1) by interacting with the NMDA receptor-associated ion channel. Phencyclidine, which also interferes with the NMDA receptor, produces psychotic effects in humans similar in many respects to schizophrenia. These findings suggest that a deficiency in glutamate transmission may be responsible in the pathology of schizophrenia (2). The neuroleptics haloperidol, clozapine and raclopride are able to reverse the behavioral changes induced by MK-801 in rats (3). Therefore the MK-801-induced activity and stereotypies in rats may represent an appropriate animal model to test the potential efficacy of antipsychotic drugs.

Experimental Procedures

Male Wistar rats (Iffa Crédo, St Germain/l'Arbresle, France), weight 250–300 g were housed 2 per cage on a 12 h/12 h light dark cycle (lights on at 7.00 a.m.) at a room temperature of 21±2° C. for a minimum of 5 days before testing. All animals had access to commercial food and tap water ad libitum.

On the day of the experiment, rats were treated with either reference drug vehicle, the reference drugs haloperidol or clozapine the test compound vehicle or test compounds. After administration, the rats were returned to their home cages for 15 minutes. The haloperidol, clozapine, test compound and vehicle treated animals received then an i.p. injection of 0.3 mg/kg MK-801. The remaining rats treated with placebo received a second injection of vehicle. The standard injection volume was 2.0 ml/kg. After 10 minutes in the home cages, rats were transferred to the test box (Plexiglas, 29×12×12 cm), 5 minutes before the assessment for accomodation. The test box was cleaned with 70% ethanol before each assessment. Stereotypies, defined as wall-contacts with the snout, and locomotion, defined as turn-rounds of 180°, were assessed during 5 minute periods.

Results

We compared the effects of three test compounds (32, 49, and 50) to haloperidol and clozapine on locomotion and stereotypies induced in rats by the N-methyl-D-aspartate (NMDA) antagonist MK-801. Haloperidol (0.25 mg/kg i.p.) and clozapine (5.0 mg/kg i.p.) caused a significant reduction of MK-801-induced locomotion and stereotypies.

Compound 32 caused a reduction of MK-801-induced locomotion and stereotypies at 1 mg/kg i.p.

Compound 49 did not reduce MK-801-induced locomotion and stereotypies at 0.5, 1.0 or 5.0 mg/kg i.p.

Compound 50 caused a reduction of MK-801-induced locomotion and stereotypies at 0.5, 1.0 and 5.0 mg/kg i.p.

Example 40
Assay for Anxiolytic Effects

In the present study, 32 was investigated on measures of anxiety in an elevated plus-maze test in the rat. In this test, an anxiolytic effect is defined as an increase in the percentage of total entries made onto the open arms and an increase in the percentage of time spent on the open arms of the elevated plus-maze. Anxiogenic drugs reduce both of these measures.

Experimental Protocols

Male rats (Iffa Crédo, St Germain/l'Arbresle, France), weight 220–320 g ate the beginning of the experiment were housed 2 per cage on a 12 h/12 h light dark cycle (lights on at 7.00 a.m.) at a room temperature of 21±2° C. for a minimum of 5 days before testing. All animals had access to commercial food and tap water ad libitum.

Elevated Plus Maze Test

The elevated plus maze test consists of four arms connected by a central square, the arms are all horizontal and at 90° C. angle from each other making the shape of a plus sign. The maze is raised to a height of 50 cm from the ground. Two of the opposite arms have a high walls whereas the other two opposite arms do not. These arms are therefore referred to as the enclosed arms, respectively.

Each test was started by placing the rat at the intersect of the maze arms facing into one of the enclosed arms. The rat had free access to all 4 arms for the period of 5 min. The number and duration of entries into each arm during this time were scored manually.

Undruged rats typically spend 30–60 seconds on the open arms and about 3 minutes on the closed arms. An anxiolytic drug effects is defined as an increase in the percentage of time spent on the open arms, out of the total time spent on either type of arm and an increase in the percentage number of entries onto the open arms, out of the total number of entries.

Results

A tendency towards an anxiolytic effects was observed at doses 1 mg/kg and 5 mg/kg for 32. An increase in the percentage of entries onto open arms as well as the time spent on these arms was observed 30 min. after iv administration of the vehicle (10% hydroxypropyl-beta-cyclodextrin) in the tail vein when compared to saline vehicle administered per os; however, this effect was not statistically significant.

Example 41
Assays Based on Human & Guinea Pig Sigma Receptors

The ability of test compounds to displace sigma ligands in vitro was determined by the methods of de Costa et al. (FEBS Lett. 251:53 (1989)) and De Haven-Hudkine et al. (Eur. J. Pharmacol. 227:372 (1992)) having guinea pig as a receptor source. Whereas, the methods of Ganapathy et al. (J. Pharm. & Exp. 289:251 (1999)) were utilized for human sigma receptors. In both assays haloperidol served as the reference compound ($IC_{50}$s (haloperidol): guinea pig sigma receptor=2.2 nM; and human sigma receptor=13 nM).

| Compound | $IC_{50}$ Against Human Sigma Receptor (nM) | $IC_{50}$ Against Guinea Pig Sigma Receptor (nM) |
|---|---|---|
| 49 | <100 | <100 |
| 50 | <1000 | <100 |
| 32 | <100 | <10 |
| 31 | <100 | <10 |
| 34 | | <100 |
| 45 | <100 | <10 |
| 53 | >1000 | <100 |
| 47 | | <10 |
| 36 | <100 | |
| 37 | <100 | <100 |
| 38 | <100 | <1000 |
| 46 | <100 | <10 |
| 43 | <1000 | |
| 39 | <1000 | <10 |

Example 42
Pharmacokinetics

Pharmacokinetic properties of the compounds were evaluated in a single rat after dosing 4 and 5 mg/kg, respectively. The dose was well tolerated by the animal. The data below is based on a 270 g rat.

Sample Preparation & Analysis in Rat Plasma

Numerous time points were taken during a 4 hour period where a 0.1 mL volume of plasma was transferred to a 1.4 mL polypropylene vial and 0.4 mL of chilled methanol (0° C.) was added. The resulting percipitate was centrifuged at 7000 rpm at 4° C. for 5 min. The resulting supernatant was analysed by HPLC using a sample volume of 0.05 mL alongside standard solutions prepared by "spiking" known amounts of the compounds into the control plasma. Standard solution of the compounds were prepared in methanol.

| PARAMETERS | 31 | 32 |
|---|---|---|
| Dose (i.v.) | 4 mg/kg | 5 mg/kg |
| Vehicle | Peg400: Dextrose (2:3 v/v) | 10% hydroxypropyl-β-cyclodextrin |
| $AUC_{0-4h}$ | 1.48 mg.h/L | 0.7 mg.h/L |
| $T_{1/2}\alpha$ | 0.12 h | 0.21 h |
| $T_{1/2}\beta$ | 0.8 h | 2.0 h |
| Vc | 0.23 L | 1.1 L |
| Vb | 0.65 L | 4.2 L |
| Clearance | 0.61 L/h | 1.9 L/h |
| Brain Tissue Distribution (4 h post dose, ng/g tissue) | 70 | 134 |

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are encompassed by the following claims.

We claim:

1. A compound represented by structure 1:

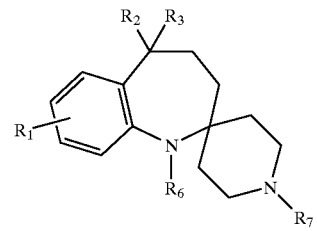

wherein

R represents independently for each occurrence hydrogen; alkyl; aryl; monocyclic or bicyclic heteroaryl with 5–12 ring atoms, of which one to three are S, O and/or N; aralkyl; or monocyclic or bicyclic heteroaralkyl with 5–12 ring atoms, of which one to three are S, O and/or N;

$R_1$ is absent, or present between 1 and 4 times;

$R_1$ represents independently for each occurrence a halide; alkyl; alkenyl; alkynyl; hydroxyl; alkoxyl; silyloxy; amino; nitro; sulfhydryl; —$R_9SR_8$; —$C(R_8)$=$NR_8$; —N=$C(R_8)_2$; —$C(O)N(R_8)_2$; —$Q_2$—$P(Q_1)(OR_8)_2$; —$Q_2$—$P(Q_1)R_8(OR_8)$; —$P(R_8)_3$; carboxyl; —$R_9C(O)OC(O)R_8$; silyl; —$SR_8$; alkylsulfonyl; arylsulfonyl; —$SeR_8$; —$R_9(O)CR_8$; —$R_9C(O)H$; —$R_9C(O)OR$; —$OC(O)R$; heteroalkyl; —$R_9CN$; —$R_9NHC$(=NH)$NH_2$; —$R_9C$(=NH)$NH_2$; —$R_9CH(OR_8)_2$; —$R_9C(OR_8)_2R_8$; —O—$N(R_8)_3$; aryl; monocyclic or bicyclic heteroaryl with 5–12 ring atoms, of which one to three ring atoms are selected independently from the group consisting of S, O, and N; aralkyl; monocyclic or bicyclic heteroaralkyl with 5–12 ring atoms, of which one to three ring atoms are selected independently from the group consisting of S, O, and N; —N$_3$; —R$_9$CH(NH)CH$_2$; —N(R$_8$)C(O)OR$_8$; —R$_9$OC(O)N(R$_8$)$_2$; —R$_9$CH(O)CH$_2$; —R$_9$C(O)N(R$_8$)OH; —ON(R$_8$)C(O)R$_8$; —R$_9$C(O)N(R$_8$)C(O)R$_8$; —N(C(O)R$_8$)$_2$; —R$_9$C(R$_8$)=NOH; —N(R$_8$)S(O)$_2$R$_8$; —C(S)N(R$_8$)$_2$; —N(R$_8$)C(S)R$_8$; —N(R$_8$)C(O)N(R$_8$)$_2$; —N(R$_8$)C(S)N(R$_8$)$_2$; or —(CH$_2$)$_m$—R$_{80}$;

R$_2$ and R$_3$ represent independently for each occurrence hydrogen; alkyl; aryl; monocyclic or bicyclic heteroaryl with 5–12 ring atoms, of which one to three are S, O and/or N; aralkyl; monocyclic or bicyclic heteroaralkyl with 5–12 ring atoms, of which one to three are S, O and/or N; OR; N(R)$_2$; CO$_2$R; C(O)N(R)$_2$; OC(O)R; or N(R)C(O)R; or the geminal instances of R$_2$ and R$_3$ taken together may represent O;

R$_6$ represents hydrogen; alkyl; aryl, monocyclic or bicyclic heteroaryl with 5–12 ring atoms, of which one to three are S, O and/or N; aralkyl; monocyclic or bicyclic heteroaralkyl with 5–12 ring atoms, of which one to three are S, O and/or N; acyl; C(O)OR; C(O)N(R)$_2$; or SO$_2$R;

R$_7$ represents hydrogen; alkyl; alkenyl; aryl; monocyclic or bicyclic heteroaryl with 5–12 ring atoms, of which one to three are S, O and/or N; aralkyl; monocyclic or bicyclic heteroaralkyl with 5–12 ring atoms, of which one to three are S, O and/or N; acyl; C(O)OR; C(O)N(R)$_2$; C(O)R$_{10}$; —R$_9$CH(O)CH$_2$; —R$_9$C$_6$H$_{11}$; or SO$_2$R;

R$_{80}$ represents independently for each occurrence an aryl, cycloalkyl, cycloalkenyl, heterocyclyl, or polycyclyl group comprised of 10 to 20 ring atoms, of which 0 to 6 are S, O and/or N and the remainder carbon;

R$_8$ represents independently for each occurrence hydrogen, alkyl, alkenyl, alkynyl, or aryl;

R$_9$ represents independently for each occurrence a bond or an alkyl, alkenyl, alkynyl, or aryl biradical;

R$_{10}$ represents independently for each occurrence morpholino or a mono or bicyclic aryl, optionally substituted by with or more R groups;

Q$_1$ represents independently for each occurrence S or O;

Q$_2$ represents independently for each occurrence O, S, or NR$_8$; and m is an integer in the range 0 to 8 inclusive;

provided that when the geminal instances of R$_2$ and R$_3$ taken together represent O, R$_7$ is not acetyl.

2. The compound of claim 1, wherein R$_2$ and R$_3$ represent independently for each occurrence H, OR, or N(R)$_2$.

3. The compound of claim 1, wherein the geminal instances of R$_2$ and R$_3$ taken together represent O.

4. A compound represented by structure 2:

2 wherein

R represents independently for each occurrence hydrogen; alkyl; aryl; monocyclic or bicyclic heteroaryl with 5–12 ring atoms, of which one to three are S, O and/or N; aralkyl; or monocyclic or bicyclic heteroaralkyl with 5–12 ring atoms, of which one to three are S, O and/or N;

R$_1$ is absent, or present between 1 and 4 times;

R$_1$ represents independently for each occurrence a halide; alkyl; alkenyl; alkynyl; hydroxyl; alkoxyl; silyloxy; amino; nitro; sulfhydryl; —R$_9$SR$_8$; —C(R$_8$)=NR$_8$; —N=C(R$_8$)$_2$; —C(O)N(R$_8$)$_2$; —Q$_2$—P(Q$_1$)(OR$_8$)$_2$; —Q$_2$—P(Q$_1$)R$_8$(OR$_8$); —P(R$_8$)$_3$; carboxyl; —R$_9$C(O)OC(O)R$_8$; silyl; —SR$_8$; alkylsulfonyl; arylsulfonyl; —SeR$_8$; —R$_9$(O)CR$_8$; —R$_9$C(O)H; —R$_9$C(O)OR; —OC(O)R; heteroalkyl; —R$_9$CN; —R$_9$NHC(=NH)NH$_2$; —R$_9$C(=NH)NH$_2$; R$_9$CH(OR$_8$)$_2$; —R$_9$C(OR$_8$)$_2$R$_8$; —O—N(R$_8$)$_3$; aryl; monocyclic or bicyclic heteroaryl with 5–12 ring atoms, of which one to three ring atoms are selected independently from the group consisting of S, O, and N; aralkyl; monocyclic or bicyclic heteroaralkyl with 5–12 ring atoms, of which one to three ring atoms are selected independently from the group consisting of S, O, and N; —N$_3$; —R$_9$CH(NH)CH$_2$; —N(R$_8$)C(O)OR$_8$; —R$_9$OC(O)N(R$_8$)$_2$; —R$_9$CH(O)CH$_2$; —R$_9$C(O)N(R$_8$)OH; —ON(R$_8$)C(O)R$_8$; —R$_9$C(O)N(R$_8$)C(O)R$_8$; —N(C(O)R$_8$)$_2$; —R$_9$C(R$_8$)=NOH; —N(R$_8$)S(O)$_2$R$_8$; —C(S)N(R$_8$)$_2$; —N(R$_8$)C(S)R$_8$; —N(R$_8$)C(O)N(R$_8$)$_2$; —N(R$_8$)C(S)N(R$_8$)$_2$; or —(CH$_2$)$_m$—R$_{80}$;

R$_2$ and R$_3$ represent independently for each occurrence hydrogen; alkyl; aryl; monocyclic or bicyclic heteroaryl with 5–12 ring atoms, of which one to three are S, O and/or N; aralkyl; monocyclic or bicyclic heteroaralkyl with 5–12 ring atoms, of which one to three are S, O and/or N; OR; N(R)$_2$; CO$_2$R; C(O)N(R)$_2$; OC(O)R; or N(R)C(O)R; or the geminal instances of R$_2$ and R$_3$ taken together may represent O;

R$_4$ represents independently for each occurrence H or alkyl;

R$_6$ represents hydrogen; alkyl; aryl; monocyclic or bicyclic heteroaryl with 5–12 ring atoms, of which one to three are S, O and/or N; aralkyl; monocyclic or bicyclic heteroaralkyl with 5–12 ring atoms, of which one to three are S, O and/or N; acyl; C(O)OR; C(O)N(R)$_2$; or SO$_2$R;

R$_7$ represents hydrogen; alkyl; alkenyl; aryl; monocyclic or bicyclic heteroaryl with 5–12 ring atoms, of which one to three are S, O and/or N; aralkyl; monocyclic or bicyclic heteroaralkyl with 5–12 ring atoms, of which one to three are S, O and/or N; C(O)N(R)$_2$; or SO$_2$R;

R$_{80}$ represents independently for each occurrence an aryl, cycloalkyl, cycloalkenyl, heterocyclyl, or polycyclyl group comprised of 10 to 20 ring atoms, of which 0 to 6 are S, O and/or N and the remainder carbon;

R$_8$ represents independently for each occurrence hydrogen, alkyl, alkenyl, alkynyl, or aryl;

R$_9$ represents independently for each occurrence a bond or an alkyl, alkenyl, alkynyl, or aryl biradical;

Q$_1$ represents independently for each occurrence S or O;

Q$_2$ represents independently for each occurrence O, S, or NR$_8$;

m is an integer in the range 0 to 8 inclusive; and n is 0 or 1;

provided that when the geminal instances of R$_2$ and R$_3$ taken together represent O, R$_7$ is not acetyl.

5. The compound of claim 4, wherein R$_2$ and R$_3$ represent independently for each occurrence H, OR, or N(R)$_2$.

6. The compound of claim 4, wherein the geminal instances of $R_2$ and $R_3$ taken together represent O.

7. The compound of claim 4, wherein $R_4$ represents independently for each occurrence H.

8. The compound of claim 4, wherein $R_6$ represents H, alkyl or acyl.

9. The compound of claim 4, wherein $R_7$ represents H, alkyl or aralkyl.

10. A compound represented by structure 4:

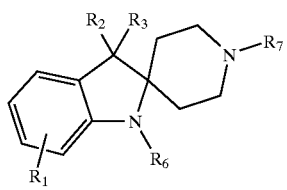

4 wherein
R represents independently for each occurrence hydrogen; alkyl; aryl; monocyclic or bicyclic heteroaryl with 5–12 ring atoms, of which one to three are S, O and/or N; aralkyl; or monocyclic or bicyclic heteroaralkyl with 5–12 ring atoms, of which one to three are S, O and/or N;

$R_1$ is absent, or present between 1 and 4 times;

$R_1$ represents independently for each occurrence a halide; alkyl; alkenyl; alkynyl; hydroxyl; alkoxyl; silyloxy; amino; nitro; sulfhydryl; —$R_9SR_8$; —$C(R_8)$=$NR_8$; —$N$=$C(R_8)_2$; —$C(O)N(R_8)_2$; —$Q_2$—$P(Q_1)(OR_8)_2$; —$Q_2$—$P(Q_1)R_8(OR_8)$; —$P(R_8)_3$; carboxyl; —$R_9C(O)OC(O)R_8$; silyl; —$SR_8$; alkylsulfonyl; arylsulfonyl; —$SeR_8$; —$R_9(O)CR_8$; —$R_9C(O)H$; —$R_9C(O)OR$; —$OC(O)R$; heteroalkyl; —$R_9CN$; —$R_9NHC$(=$NH$)$NH_2$; —$R_9C$(=$NH$)$NH_2$; —$R_9CH(OR_8)_2$; —$R_9C(OR_8)_2R_8$; —$O$—$N(R_8)_3$; aryl; monocyclic or bicyclic heteroaryl with 5–12 ring atoms, of which one to three ring atoms are selected independently from the group consisting of S, O, and N; aralkyl; monocyclic or bicyclic heteroaralkyl with 5–12 ring atoms, of which one to three ring atoms are selected independently from the group consisting of S, O, and N; —$N_3$; —$R_9CH(NH)CH_2$; —$N(R_8)C(O)OR_8$; —$R_9OC(O)N(R_8)_2$; —$R_9CH(O)CH_2$; —$R_9C(O)N(R_8)OH$; —$ON(R_8)C(O)R_8$; —$R_9C(O)N(R_8)C(O)R_8$; —$N(C(O)R_8)_2$; —$R_9C(R_8)$=$NOH$; —$N(R_8)S(O)_2R_8$; —$C(S)N(R_8)_2$; —$N(R_8)C(S)R_8$; —$N(R_8)C(O)N(R_8)_2$; —$N(R_8)C(S)N(R_8)_2$; or —$(CH_2)_m$—$R_{80}$;

$R_2$ and $R_3$ represent independently for each occurrence hydrogen; alkyl; aryl; monocyclic or bicyclic heteroaryl with 5–12 ring atoms, of which one to three are S, O and/or N; aralkyl; monocyclic or bicyclic heteroaralkyl with 5–12 ring atoms, of which one to three are S, O and/or N; OR; $N(R)_2$; $CO_2R$; $C(O)N(R)_2$; $OC(O)R$; or $N(R)C(O)R$; or the geminal instances of $R_2$ and $R_3$ taken together may represent $C(R)_2$;

$R_6$ represents hydrogen; alkyl; aryl; monocyclic or bicyclic heteroaryl with 5–12 ring atoms, of which one to three are S, O and/or N; aralkyl; monocyclic or bicyclic heteroaralkyl with 5–12 ring atoms, of which one to three are S, O and/or N; acyl; $C(O)OR$; $C(O)N(R)_2$; or $SO_2R$;

$R_7$ represents hydrogen; alkyl; alkenyl; aryl; monocyclic or bicyclic heteroaryl with 5–12 ring atoms, of which one to three are S, O and/or N; aralkyl; monocyclic or bicyclic heteroaralkyl with 5–12 ring atoms, or which one to three are S, O and/or N; acyl; $C(O)N(R)_2$; or $SO_2R$;

$R_{80}$ represents independently for each occurrence an aryl, cycloalkyl, cycloalkenyl, heterocyclyl, or polycyclyl group comprised of 10 to 20 ring atoms, of which 0 to 6 are S, O and/or N and the remainder carbon;

$R_8$ represents independently for each occurrence hydrogen, alkyl, alkenyl, alkynyl, or aryl;

$R_9$ represents independently for each occurrence a bond or an alkyl, alkenyl, alkynyl, or aryl biradical;

$Q_1$ represents independently for each occurrence S or O;

$Q_2$ represents independently for each occurrence O, S, or $NR_8$; and m is independently for each occurrence an integer in the range 0 to 8 inclusive.

11. The compound of claim 10, wherein $R_6$ represents H, alkyl or acyl.

12. The compound of claim 10, wherein $R_7$ represents H, alkyl or aralkyl.

13. The compound of claim 1, 4, or 10, wherein said compound is a single stereoisomer.

14. A formulation, comprising a compound of claim 1, 4, or 10; and a pharmaceutically acceptable excipient.

15. The compound of claim 1, wherein $R_1$ is absent; $R_2$ and $R_3$ taken together represent O, $R_6$ represents H; and $R_7$ represents H.

16. The compound of claim 1, wherein $R_1$ is absent; $R_2$ and $R_3$ taken together represent O; $R_6$ represents H; and $R_7$ represents acetyl.

17. The compound of claim 1, wherein $R_1$ is absent; $R_2$ and $R_3$ taken together represent O; $R_6$ represents H; and $R_7$ represents

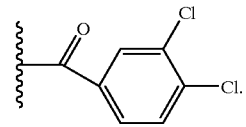

18. The compound of claim 1, wherein $R_1$ is absent; $R_2$ and $R_3$ taken together represent O; $R_6$ represents H; and $R_7$ represents

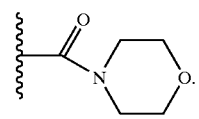

19. The compound of claim 1, wherein $R_1$ is absent; $R_2$ and $R_3$ taken together represent O; $R_6$ represents H; and $R_7$ represents —$C(O)$—$C_6H_4$-t-butyl.

20. The compound of claim 1, wherein $R_1$ is absent; $R_2$ and $R_3$ taken together represent O; $R_6$ represents H; and $R_7$ represents

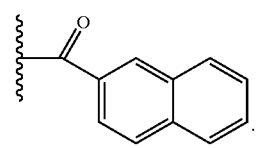

21. The compound of claim 1, wherein $R_1$ is absent; $R_2$ and $R_3$ taken together represent O; $R_6$ represents H; and $R_7$ represents —$S(O)_2C_6H_4$.

22. The compound of claim 1, wherein $R_1$ is absent; $R_2$ and $R_3$ taken together represent O; $R_6$ represents H; and $R_7$ represents —$CH_2C_6H_4OCF_3$.

23. The compound of claim 1, wherein $R_1$ is absent; $R_2$ and $R_3$ taken together represent O; $R_6$ represents H; and $R_7$ represents —$CH_2CH_2C_6H_5$.

24. The compound of claim 1, wherein $R_1$ is absent; $R_2$ and $R_3$ taken together represent O; $R_6$ represents H; and $R_7$ represents

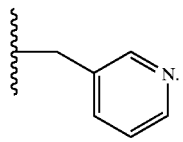

25. The compound of claim 1, wherein $R_1$ is absent; $R_2$ and $R_3$ taken together represent O; $R_6$ represents H; and $R_7$ represents

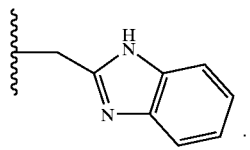

26. The compound of claim 1, wherein $R_1$ is absent; $R_2$ and $R_3$ taken together represent O; $R_6$ represents H; and $R_7$ represents —$CH_2C_6H_4CO_2Me$.

27. The compound of claim 1, wherein $R_1$ is absent; $R_2$ and $R_3$ taken together represent O; $R_6$ represents H; and $R_7$ represents —$CH_2CH$=$CMe_2$.

28. The compound of claim 1, wherein $R_1$ is absent; $R_2$ and $R_3$ taken together represent O; $R_6$ represents H; and $R_7$ represents —$CH_2C_6H_4CN$.

29. The compound of claim 1, wherein $R_1$ is absent; $R_2$ and $R_3$ taken together represent O; $R_6$ represents H; and $R_7$ represents —$CH_2CH_2C_6H_{11}$.

30. The compound of claim 1, wherein $R_1$ is absent; $R_2$ and $R_3$ taken together represent O; $R_6$ represents H; and $R_7$ represents —$CH_2CH$=$CH_2$.

31. The compound of claim 1, wherein $R_1$ is absent; $R_2$ and $R_3$ taken together represent O; $R_6$ represents H; and $R_7$ represents —$CH_2CH_2$-t-butyl.

32. The compound of claim 1, wherein $R_1$ is absent; $R_2$ and $R_3$ taken together represent O; $R_6$ represents H; and $R_7$ represents —$CH_2CH(O)CH_2$.

33. The compound of claim 1, wherein $R_1$ is absent; $R_2$ and $R_3$ taken together represent O; $R_6$ represents H; and $R_7$ represents —$CH_2CH_2CHMe_2$.

34. The compound of claim 1, wherein $R_1$ is absent; $R_2$ and $R_3$ taken together represent O; $R_4$ represents H; and $R_7$ represents

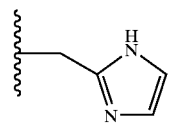

35. The compound of claim 1, wherein $R_1$ is absent; $R_2$ and $R_3$ taken together represent O; $R_4$ represents H; and $R_7$ represents —$CH_2C_6H_4F$.

36. The compound of claim 1, wherein $R_1$ is absent; $R_2$ represents OH; $R_3$ represents H; $R_6$ represents H; and $R_7$ represents —$CH_2C_6H_4F$.

37. The compound of claim 1, wherein $R_1$ is absent; $R_2$ represents $NH_2$; $R_3$ represents H; $R_6$ represents H; and $R_7$ represents —$CH_2C_6H_4F$.

38. The compound of claim 1, wherein $R_1$ is absent; $R_2$ represents NHAc; $R_3$ represents H; $R_6$ represents H; and $R_7$ represents —$CH_2C_6H_4F$.

39. The compound of claim 1, wherein $R_1$ is absent; $R_2$ and $R_3$ taken together represent O; $R_6$ represents H; and $R_7$ represents

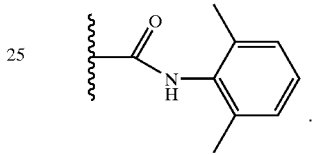

40. The compound of claim 1, wherein $R_1$ is absent; $R_2$ represents H, $R_3$ represents H; $R_6$ represents H; and $R_7$ represent; —$CH^2C_6H_4F$.

41. The compound of claim 1, wherein $R_1$ is absent; $R_2$ and $R_3$ taken together represent O; $R_6$ represents H; and $R_7$ represents —$CH_2CH(OH)C_6H_5$.

42. The compound of claim 1, wherein $R_1$ is absent; $R_2$ and $R_3$ taken together represent O; $R_6$ represents H; and $R_7$ represents —$CH(Me)C_6H_4F$.

43. The compound of claim 4, wherein n is 2; $R_1$ is absent; $R_2$ represents OH; $R_3$ represents H; $R_6$ represents H; and $R_7$ represents —$CH_2C_6H_4F$.

44. The compound of claim 4, wherein n is 2; $R_1$ is absent; $R_2$ and $R_3$ taken together represent O; $R_6$ represents H; and $R_7$ represents —$CH_2C_6H_4F$.

45. The compound of claim 4, wherein n is 2; $R_1$ is absent; $R_2$ represents H; $R_3$ represents H; $R_6$ represents H; and $R_7$ represents —$CH_2C_6H_4F$.

46. The compound of claim 4, wherein n is 2; $R_1$ is absent; $R_2$ and $R_3$ taken together represent O; $R_6$ represents H; and $R_7$ represents H.

47. The compound of claim 4, wherein n is 1; $R_1$ is absent; $R_2$ is Me; $R_3$ is H; $R_6$ represents H; and R, is —$CH_2C_6H_4F$.

48. The compound of claim 10, wherein $R_1$ is absent, $R_2$ and $R_3$ taken together represent $C(R)_2$; $R_6$ represents H; and $R_7$ represents —$CH_2C_6H_4F$.

* * * * *